US005866361A

United States Patent [19]
Dujon et al.

[11] Patent Number: 5,866,361
[45] Date of Patent: Feb. 2, 1999

[54] NUCLEOTIDE SEQUENCE ENCODING THE ENZYME I-SCEI AND THE USES THEREOF

[75] Inventors: Bernard Dujon, Gif Sur Yvette; Andre Choulika; Arnaud Perrin, both of Paris; Jean-Francois Nicolas, Noisy Le Roi, all of France

[73] Assignees: Institut Pasteur; Universite Pierre et Marie Curie, both of Paris, France

[21] Appl. No.: 465,273

[22] Filed: Jun. 5, 1995

Related U.S. Application Data

[63] Continuation of Ser. No. 336,241, Nov. 7, 1994, which is a continuation-in-part of Ser. No. 971,160, Nov. 5, 1992, Pat. No. 5,474,896, which is a continuation-in-part of Ser. No. 879,689, May 5, 1992, abandoned.

[51] Int. Cl.$^6$ .............................. C12N 1/21; C12N 9/14; C12N 15/55; C12N 15/63
[52] U.S. Cl. ..................... 435/69.1; 435/199; 435/252.3; 435/252.33; 435/172.3; 530/350; 530/824; 536/23.2
[58] Field of Search ................................ 435/172.3, 69.1, 435/199, 252.3, 252.33; 530/350; 536/23.2

[56] References Cited

PUBLICATIONS

Dujon, B., Sequence of the Intron and Flanking Exons of the Mitochondrial 21s rDNA Gene of Yeast Strains Having Different Alleles at the ω and rib–1 Loci, Cell, vol. 20: 185–197 (1980).
Michel, F. et al., Comparison of fungal mitochondrial introns reveals extensive homologies in RNA secondary structure, BIOCHIMIE, vol. 64: 867–881 (1982).
Michel, F. and Dujon, B., Conservation of RNA secondary structures in two intron families including mitochondrial –, chloroplast–and nuclear–encoded members, EMBO Journal, vol. 2 (1) : 33–38 (1983).
Jacquier, A. and Dujon, B., The Intron of the Mitochondrial 21s rRNA Gene: Distribution in Different Yeast Species and Sequence Comparison Between *Kluyveromyces thermotolerans* and *Saccharomyces cerevisiae*, Mol. Gen. Genet., 192: 487–499 (1983).
Dujon, B. and Jacquier, A., Mitochondria 1983, Walter de Gruyter & Co., pp. 389–403.
Jacquier, A. and Dujon, B., an Intron–Encoded Protein is Active in a Gene Conversion Process That Spreads an Intron into a Mitochondrial Gene, Cell, vol. 41: 383–394 (1985).
Dujon, B. et al., in Achievements and Perspectives of Mitochondrial Research, vol. II: *Biogenesis*, Elsevier Science Publishers, pp. 215–225 (1985).
Colleaux, L. et al., Universal Code Equivalent of a Yeast Mitochondrial Intron Reading Frame is Expressed into *E. Coli* as a Specific Double Strand Endonuclease, Cell, vol. 44: 521–533 (1986).
Michel, F. and Dujon, B., Genetic Exchanges between Bacteriophage T4 and Filamentous Fungi?, Cell, vol. 46: 323 (1986).
Colleaux, L. et al., Recognition and cleavage site of the intron–encoded omega transposase, Proc. Natl. Acad. Sci. USA, vol. 85: 6022–6026 (1988).
Dujon, B., Group I introns as mobile genetic elements: facts and mechanistic speculations—a review, Gene, vol. 82: 91–114 (1989).
Dujon, B. et al., Mobile introns: definition of terms and recommended nomenclature, Gene, vol. 82: 115–118 (1989).
Monteilhet, C. et al., Purification and characterization of the in vitro activity of I–SceI, a novel and highly specific endonuclease encoded by a group 1 intron, Nucleic Acids Research, vol. 18 (6), 1407–1413 (1990).
Colleaux, L. et al., The apocytochrome b gene of *Chlamydomonas smithii* contains a mobile intron related to both Saccharomyces and Neurospora introns, Mol. Gen. Genet., vol. 223 : 288–296 (1990).
Dujon, B. et al., in Extrachromosomal Elements in Lower Eukaryotes, (Plenum Publishing Corporation 1986), pp. 5–27.
Thierry, A. et al., Cleavage of yeast and bacteriophage T7 genomes at a single site using the rare cutter endonuclease I–SceI, Nucleic Acids Research, vol. 19 (1) : 189–190 (1991).
Plessis, A. et al., Site–specific recombination by I–SceI; a mitochondrial group I intron–encoded endonuclease expressed in the yeast nucleus, Genetics, vol. 130 (3) : 451–460 (1992).
Tartof et al., "New cloning vectors and techniques . . ."Gene 67:169–182 (1988).
Colleaux et al., "Rapid Physical Mapping of YAC inserts . . . ," Human Mol. Genet., 2 (3) :265–271 (1993).
Dujon, B. et al., "Mobile Introns," Abstract presented at EMBO Workshop, Roscoff, France, Jun. 24–28, 1990.

*Primary Examiner*—John L. LeGuyader
*Assistant Examiner*—Johnny F. Railey, II
*Attorney, Agent, or Firm*—Finnegan, Henderson, Farabow, Garrett & Dunner, L.L.P.

[57] ABSTRACT

An isolated DNA encoding the enzyme I-SceI is provided. The DNA sequence can be incorporated in cloning and expression vectors, transformed cell lines and transgenic animals. The vectors are useful in gene mapping and site-directed insertion of genes.

8 Claims, 46 Drawing Sheets

FIG. I

```
AAAAATAAAAATCAT ATG AAA AAT ATT AAA AAT CAA GTA ATC AAT CTC GGT CCT AAT TCT
                 M   K   N   I   K   N   Q   V   I   N   L   G   P   N   S
AAA TTA TTA AAA GAA TAT AAA CAA TTA ATT AAT ATT GAA CAA TTT GAA GCA
 K   L   L   K   E   Y   K   Q   L   I   N   I   E   Q   F   E   A
GGT ATT GGT TTA ATT TTA GGA GAT GCT TAT ATT CGT AGT GAT CGT GAA ACT TAT
 G   I   G   L   I   L   G   D   A   Y   I   R   S   D   R   E   T   Y
TGT ATG CAA TTT CAC TCC AAA AAT AAG GCA TAC ATG GAT GTA TGT GAA ACT GAT
 C   M   Q   F   H   S   K   N   K   A   Y   M   D   V   C   E   T   D
CAA TGG GTA TTA TCA CCT CAT AAA AAA GAA CAT CAT GTT TTT GAA TTA TTA GTA
 Q   W   V   L   S   P   H   K   K   E   H   H   V   F   E   L   L   V
ATT ACC GGA GCT CAA ACT CTT ATT AAT AAT CAT AAT GGT TTT TAT AAT TAT TTT
 I   T   G   A   Q   T   L   I   N   N   H   N   G   F   Y   N   Y   F
ATT GTA AAT AAA AAA TGG TTT ATG GAT GAT CAA TTA AAA GGA GTT TGG GAT ATG
 I   V   N   K   K   W   F   M   D   D   Q   L   K   G   V   W   D   M
AGT CTG GCA TAT GTA ATT AGA TTT ATG AAT TTT ACA CAA TTA TAT TAT GAA TTT
 S   L   A   Y   V   I   R   F   M   N   F   T   Q   L   Y   Y   E   F
AAT AAA ATT AGA AAT GAT AGT AGT CAA AGT AAT GGA ATT TAT AAA GAA AAT CCT
 N   K   I   R   N   D   S   S   Q   S   N   G   I   Y   K   E   N   P
AAA GGT ATT GAT TAT TCT ATG TAT AAA CTG CCT AAT ACT TCA TCC GAA ACT TTT
 K   G   I   D   Y   S   M   Y   K   L   P   N   T   S   S   E   T   F
ATT CCT CAA ATG ATG TAT AAA CTG CCT AAT ACT TTT TTA AAA TAA
 I   P   Q   M   M   Y   K   L   P   N   T   F   L   K   *
```

```
Bam HI
CCGGATCCATG CAT ATG AAA AAC ATC AAA AAA AAC CAG GTA ATG AAC CTG TCT
            M   H   M   K   N   I   K   K   N   Q   V   M   N   L   S

AAA CTG CTG AAA GAA TAC AAA TCC CAG CTG GCT TAC GGT CCG AAC TCT
    K   L   L   K   E   Y   K   S   Q   L   A   Y   G   P   N   S

1.  GGT ACT GGT ATC CTG CTG GAG ATC CGT TCT ATC CGT GAT GAA TTC GAA GCA
    G   T   G   I   L   L   E   I   R   S   I   R   D   E   F   E   A

TGT ATG CAG TTC GAG TCC AAA AAC GCA TAC GAC CAC GTA ATG GAA ACC TAC
    C   M   Q   F   E   S   K   N   A   Y   D   H   V   M   E   T   Y

CAG TGG GTA CTG TCC CCG CAC CCG AAA AAA CAC CGT GTT TTC GAT CTG TAC GAT
    Q   W   V   L   S   P   H   P   K   K   H   R   V   F   D   L   Y   D

ATC ACC TGG GCC GCC CAG AAA ACC ATC CCG AAA CAC AAC GCT GCT ACC AAC CTG AAC CTG
    I   T   W   G   A   Q   K   T   I   P   K   H   N   A   A   T   N   L   N   L

ATC GTT GAA ACC CAG CTT AAA GGT GAT TGG AAA TAC TAC CCG ATG
    I   V   E   T   Q   L   K   G   D   W   K   Y   Y   P   M

2.  TCT CTG GCA TAC TGG TTC ATG GAT GGT GGT TTC ACT TTC GAA GAA TAC TCT ACC
    S   L   A   Y   W   F   M   D   G   G   F   T   F   E   E   Y   S   T

AAC AAA TCG ATC GTA CTG AAC AAA CAG ACC CTG AAC TGT TAC CTA GAA GTA TAC CTG GTT
    N   K   S   I   V   L   N   K   Q   T   L   N   C   Y   L   E   V   Y   L   V

AAG GGT CTG CGT AAC AAA TTC CAA ATG TCT ATC TTC TAC TAC CTG AAA AAC AAA CCG
    K   G   L   R   N   K   F   Q   M   S   I   F   Y   Y   L   K   N   K   P

ATC ATC TAC ATC GAT TCT ATG TAC AAA CTG CCG AAC ACT ATC TCC TCC GAA ACT TTC CTG AAA TAA
    I   I   Y   I   D   S   M   Y   K   L   P   N   T   I   S   S   E   T   F   L   K   *

ATC CCG CAG ATG ATG TAC AAA CTG CCG
    I   P   Q   M   M   Y   K   L   P

TAAGTCGACTGCAGGATCCGGTAAGTAAGTAA
     SalI PstI BamHI 1 and 2:  THESE AMINO ACIDS ARE ABSOLUTELY NECESSARY TO PRODUCE CATALYTIC
          ACTIVITY.  OTHER SUBSTITUTIONS ARE POSSIBLE, SUCH AS DELETIONS
          OF THE 10 FIRST AMINO ACIDS.
```

FIG. 2

```
1667 GCGGACAGGTATCCGGTAAGCGGCAGGGTCGGAACAGGAGAGCGCGAGGGAGCTTCCAGGGGAAACGCCTGGTATCT 1746
1747 TTATAGTCCTGTCGGGTTTCGCCACCTCTGAGCTCGATTTTTGTG ATG CTC GTC AGG GGG GCG GAG 1818
  1                                                M   L   V   R   G   A   E    7
1819 CCT ATG GAA AAA CGC CAG CAA CGC GGC CTT TTT ACG GTT CCT GGC CTT TTG CTG GCC TTT 1878
  8   P   M   E   K   R   Q   Q   R   G   L   F   T   V   P   G   L   L   L   A   F   27
1879 TGC TCA CAT GTT CTT TCC TGC GTT ATC CCC TGA TTCTGTGGATAACCGTATTACCGCCTTGAGTGAGC 1947
 28   C   S   H   V   L   S   C   V   I   P   *                                       38
1948 TGATACCGCTCGCCGCCAGCCGAACGACCGAGCGCAGCGAGTCAGTGAGCGAGGAAGCGGAAGAGCGCCAATACGCAAAC 2027
2028 CGCCTCTCCCCGGCGTTGGCCGATTCATTA ATG CAG CTG GCA CGA CAG GTT TCC CGA CTG GAA AGC 2094
  1                                M   Q   L   A   R   Q   V   S   R   L   E   S    12
2095 GGG CAG TGA GCGCAACGCAATTA ATG TGA GTTAGCTCACTCATTAGGCACCCCAGGCTTTACACTTT ATG 2164
 13   G   Q   *                   M   *                                          M    1
2165 CTT CCG GCT CGT ATG TTG TGT GGA ATT GTG AGC GGA TAA CAATTTCACACAGGAAACAGCT ATG 2228
  2   L   P   A   R   M   L   C   G   I   V   S   G   *                          M    1
2229 ACC GTC ACC ATT ACG AAT TCT CAT GTT TGA CAGCTTATCATCGATAAGCTTTA ATG CGG TAG TTTATCAC 2295
  2   T   V   T   I   T   N   S   H   V   *                         M   R   *         3
2296 AGTTAAAATTGCTAACGCAGTCAGGCACCGTGT ATG AAA TCT AAC AAT GCG CTC ATC GTC ATC CTC GGC 2363
  1                                    M   K   S   N   N   A   L   I   V   I   L   G   12
2364 ACC GTC ACC CTG GAT GCT GTA GGC ATA GGC TTG GTT ATG CCG GTA CTG CCG GGC CTC TTG 2423
 13   T   V   T   L   D   A   V   G   I   G   L   V   M   P   V   L   P   G   L   L   32
2424 CGG GAT ATC CGC CTG ATG CGT GAA CGT GAC GGA CGT AAC CAC CGC GAC ATG TGT GTG CTG 2483
 33   R   D   I   R   L   M   R   E   R   D   G   R   N   H   R   D   M   C   V   L   52
2484 TTC CGG TGG GCA TGC CAG GAC AAC TTC TGG TCC GGT AAC GTG CTG AGC CTG CCG GCC AAG CTT 2543
 53   F   R   W   A   C   Q   D   N   F   W   S   G   N   V   L   S   L   P   A   K   L   72
```

<u>Positions that can be changed without affecting enzyme activity (demonstrated)</u>
positions -1 and -2 are not natural. The two amino acids are added due to cloning strategies positions 1 to 10: can be deleted
position 36: G is tolerated
position 40: M or V are tolerated
position 41: S or N are tolerated
position 43: A is tolerated
position 46: V or N are tolerated
position 91: A is tolerated
positions 123 and 156: L are tolerated
position 223: A and S are tolerated Changes that affect enzyme activity (demonstrated)

position 19: L to S
position 38: I to S or N
position 39: G to D or R
position 40: L to Q
position 42: L to R
position 44: D to E G or H
position 45: A to E or D
position 46: Y to D
position 47: I to R or N
position 80: L to S
position 144: D to E
position 145: D to E
position 146: G to E
position 147: G to S

FIG. 5

Group I Intron Encoded Endonucleases and Related Endonucleases

| | ENDONUCLEASE | RECOGNITION SEQUENCE / CLEAVAGE SITE (▽ INTRON SITE) |
|---|---|---|
| TWO DODECAPEPTIDE FAMILY (OR 4 BP CUTTERS) | I-Sce I (Saccharomyces mitochondria) | CGC TAGGGATAA CAGGGTAAT ATAGC<br>GCG ATCCCTATTGTCCCATTA TATCG |
| | I-Sce IV (Saccharomyces mitochondria) | TTCTCATGATT AGCTCTAATCCATGG<br>AAGAGTAC TAATCGAGATTAGGTACC |
| | I-Sce II (Saccharomyces mitochondria) | C TTTGGTCATCC AGAAGTA TATATTT<br>G AAACCAGTAGGTCTTCAT ATATAAA |
| | I-Ceu I (Chlamydomonas chloroplast) | TAACGGTCCTAA GGTAGCGAAATTCA<br>ATTGCCAGGATTCCATCGCTTTAAGT |
| | I-Ppo I (Physarum nucleus) | TG ACTCTCTTAA GGTAGCC AAATGCC<br>AC TGAGAGAATTCCATCGG TTTACGG |
| | I-Sce III (Saccharomyces mitochondria) | GGAGGTTTTGGTAACTATTTATTACC<br>CCTCCAAAACCATTGATAAATAATGG |
| | I-Cre I (Chlamydomonas chloroplast) | GGGTTCAAAACGTCGTGAGACAGTTT<br>CCCAAGTTTTGCAGCACTCTGTCAAA |
| | Endo. Sce I(RF3) (Saccharomyces mitochondria) (Non intronic) | GATGCTGTAGGC ATAGGCTTGGTTAT<br>CTACGACATCCGTATCCGAACCAATA |
| | HO (Saccharomyces nucleus) (Non intronic) | C TTTCCGCAACA GT ATAATTTTATAA<br>G AAAGGCGTTGTCA TATTAAAATATT |
| | I-Csm I (Chlamydomonas mitochondria) (Putative endonuclease) | ACCATGGGGTCAAATGTCTTTCTGGG<br>TGGTACCCCAGTTTACAGAAAGACCC |
| | I-Pan I (Podospora mitochondria) (Putative endonuclease) | GTGCCTGAATGATATTTATTACCTTT<br>CACGGACTTACTATAAATAATGGAAA |
| OTHER STRUCTURAL FAMILIES | I Tev I (Bacteriophage T4) | CAAC GCTCAGTAGATGTTTTCTTGGGTCTACCGTTTAAT<br>GT TGCGAGTCATCTACAAAAGAACCCAGATGGCAAATTA |
| | I Tev II | CAAGCTTATGAGTATGAAGTGAACACGT TATT<br>GTTCGAATACTCATACTTCACTTGTGC AATAA |
| | I Tev III | GCTATTCGTTTT TAT GTATCTTTTGCGTGTAGCTTTAA<br>CGATAAGCAAAA ATA CATAGAAAACGCACATCGAAATT |

FIG. 6

```
                                    Sau3A I
                                    Mbo I
                                    Dpn II
                              ScrF I
                              Nci I
                              Msp I
                              Hpa II
                              Dsa V
                              BstK I
                              Xma I
                              Sma I
                              ScrF I
                              Nci I
                              Dsa V
                         Rsa I    Dpn I
                         Nla IV   Nla IV
                  Sac I  Csp6 I   Alw I
                  HgiA I BstK I              Taq I
                  Ec1136 I BsaJ I            Sal I
         Sph I   Rma I    Kpn I   BstY I    Hinc II
         NspC I  Bsp1286 I Bcn I  Sfe I
    EcoR I    Xba I      Ban I    BamH I   Acc I    I-Sce I
    Apo I   Nla III  Ban II    Bcn I    Sfc I     Rma I
  Taq I   Nsp7524 I  Alu I   Ava I    Pst I    Hga I
  Alu I     Nsp I   Bfa I   Asp718   Alw I   BspW I     Bfa I             EcoR V
   | |      |  |    |  |     |  |    |  |    |  |  |    |  |               |
CCAAGCTCGAATTCGCATGCTCTAGAGCTCGGTACCCGGGATCCTGCAGTCGACGCTAGGGATAACAGGGTAATACAGAT   2320
GGTTCGAGCTTAAGCGTACGAGATCTCGAGCCATGGGCCCTAGGACGTCAGCTGCGATCCCTATTGTCCCATTATGTCTA
  | | |•    | |  •| |   | |   •| |   | |    | | | |   |T •         •       | •
  2244     2255    2262    2271    2279   2286     2296                   2318
    2247   2255      2266    2275    2284    2292
      2249    2256    2265    2275    2284      2296
      2249         2261   2271    2279         2289    2297
         2255      2265   2271    2276    2284
         2255    2262    2271    2279        2289
                 2265        2275            2289
                 2265        2275            2290
                 2265    2272    2280
                       2271    2279
                       2272    2280
                            2275
                            2275
                            2275
                            2275
                            2275
                            2275
                            2276
                            2276
                            2276
                            2276
                            2276
                            2276
                                2280
                                2280
                                2280
```

Construction: pGP 704 from De Lorenzo, with transposase gene and insertion of the linker[I-SceI] in NotI unique site

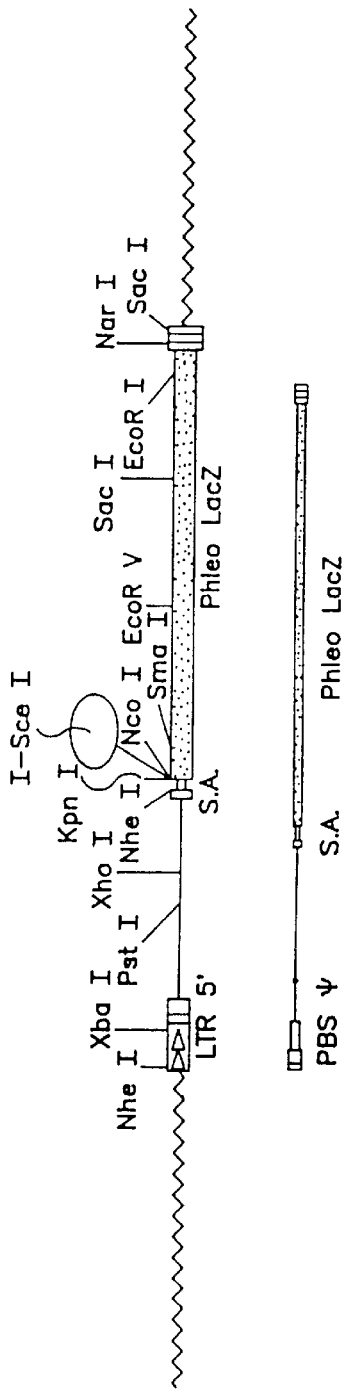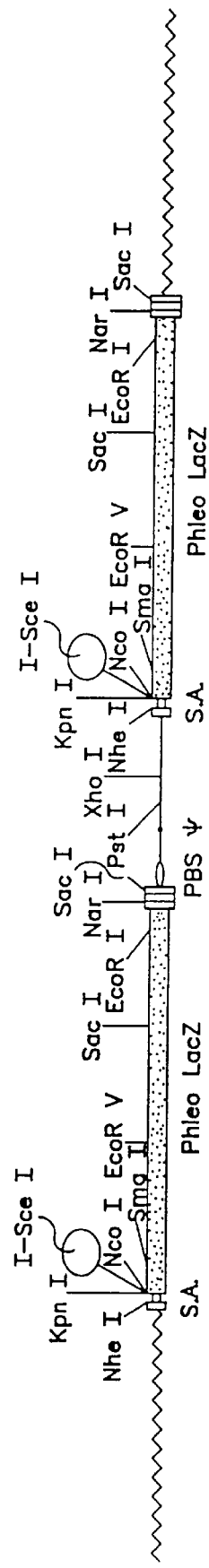
FIG. 13B
FIG. 13C

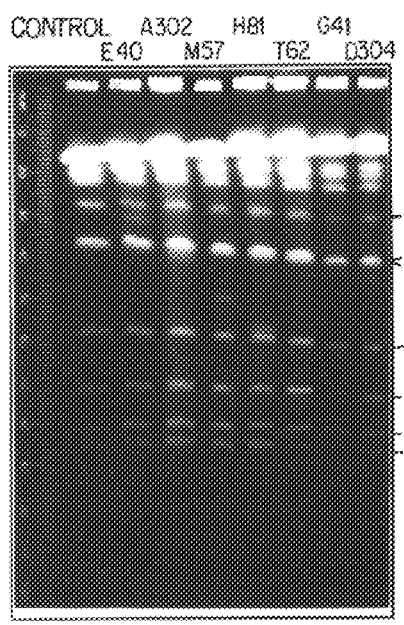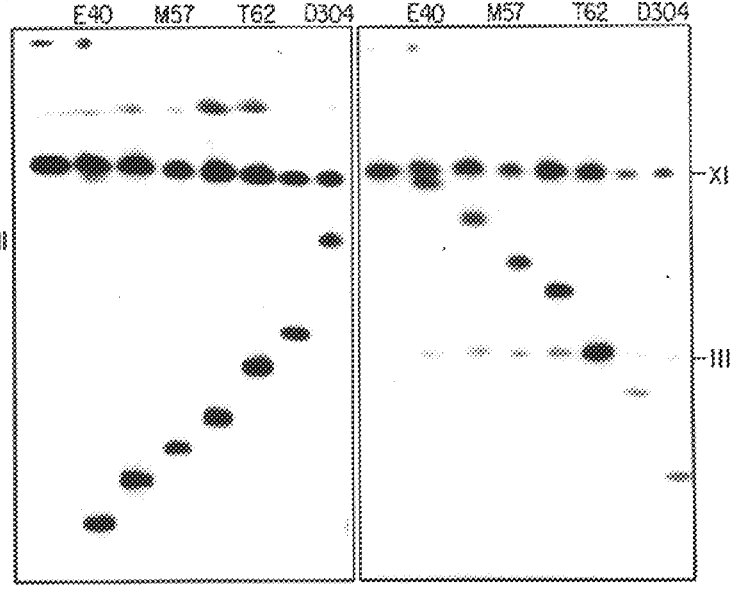
FIG. 16A  FIG. 16B  FIG. 16C

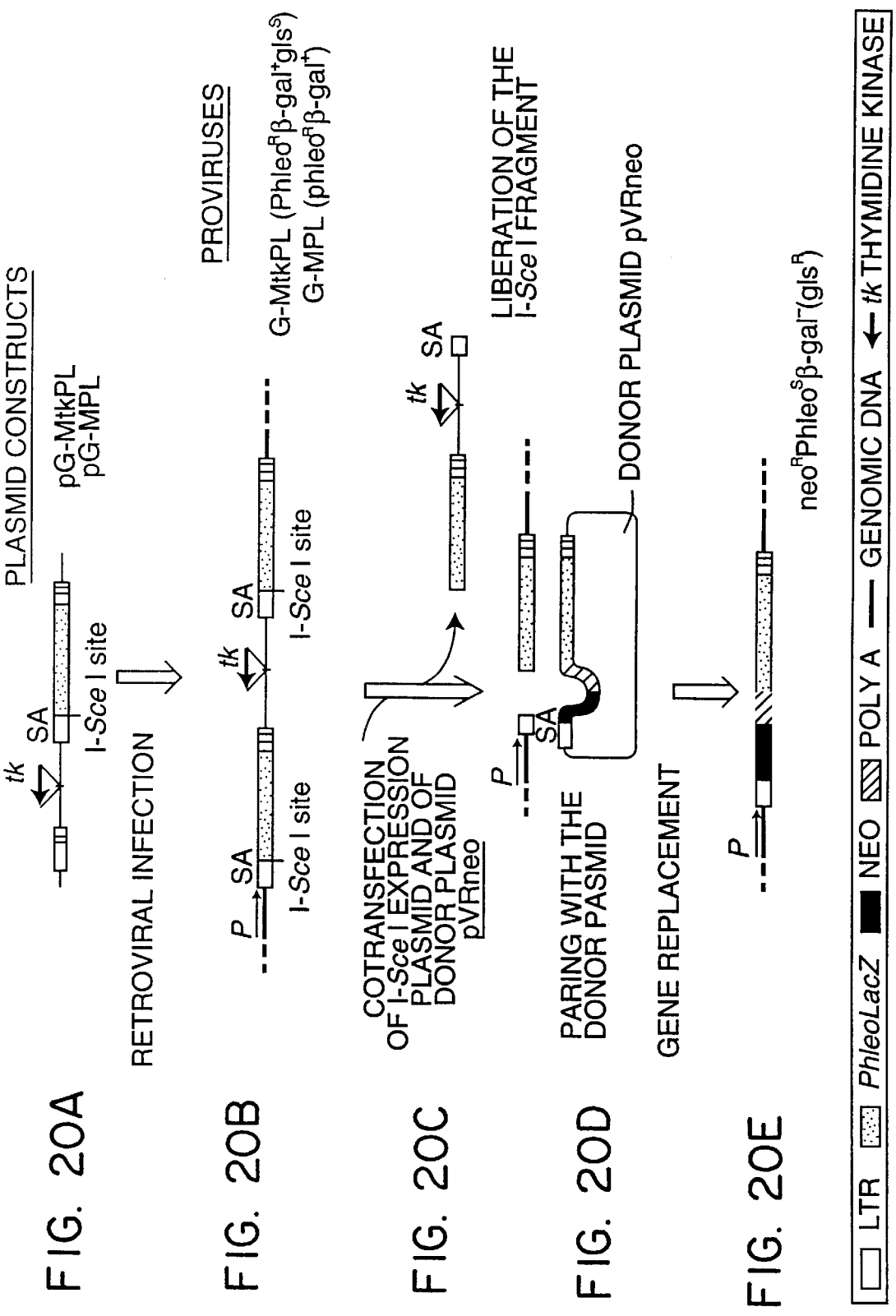

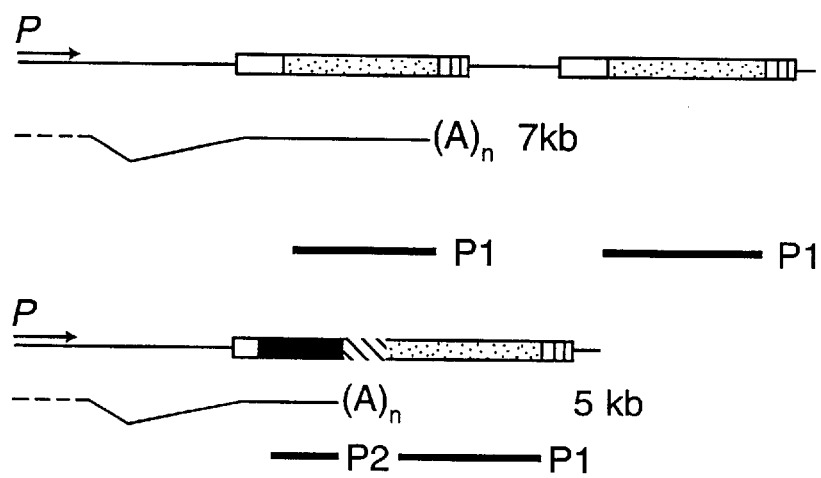
PCC7-S / G-MPL, CLONE 3
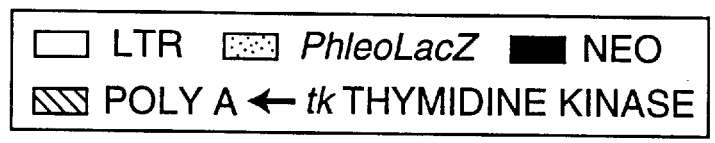
FIG. 24A

A. CHROMOSOMAL DNA
CONTAINING PROVIRUS
PHENOTYPES

[Phleo$^R$, Gls$^S$, β-Gal$^+$]

TRANSFECTION BY
I-Sce I ENDONUCLEASE
EXPRESSION VECTOR

B. INTRA-CHROMOSOMAL
RECOMBINATIONS EVENTS

1. THE LEFT I-Sce I IS CUT.
PAIRING AND RECOMBINATION

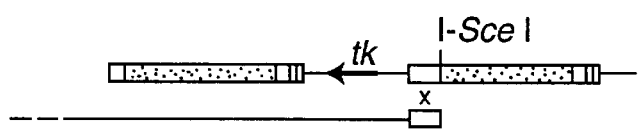

2. THE RIGHT I-Sce I IS CUT.
PAIRING AND RECOMBINATION

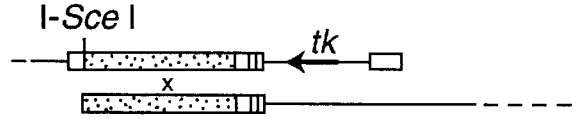

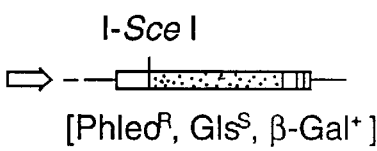
[Phleo$^R$, Gls$^S$, β-Gal$^+$]

3. BOTH I-Sce I SITES ARE CUT.
RELIGATION BY END-JOINING

C. INTER-CHROMOSOMAL RECOMBINATION EVENT
BOTH I-Sce I SITES ARE CUT. GAP REPAIR USING INTACT
CHROMOSOME SEQUENCES

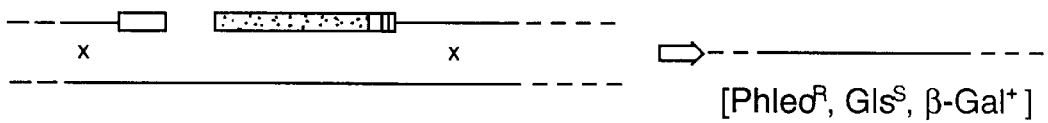
[Phleo$^R$, Gls$^S$, β-Gal$^+$]

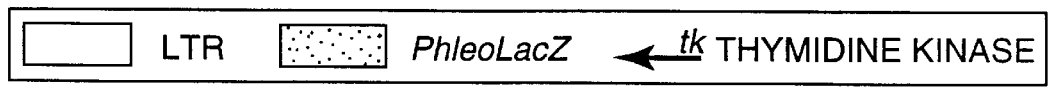

FIG. 25

1. PARENTAL DNA, G-MtkPL
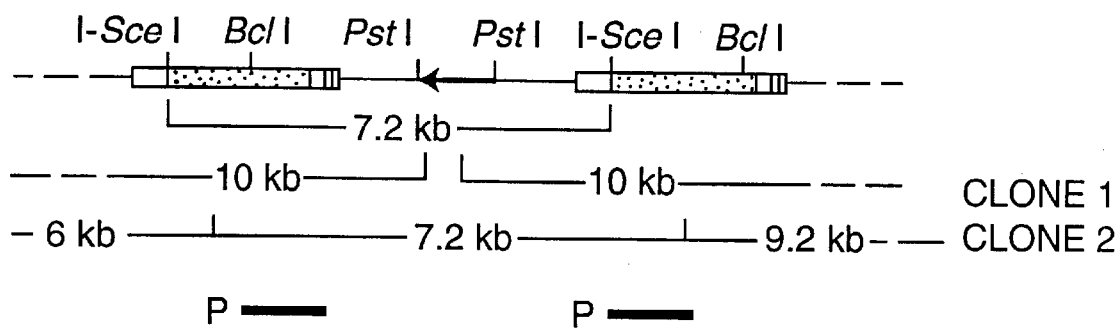
2. INTRA-MOLECULAR RECOMBINATION EVENT
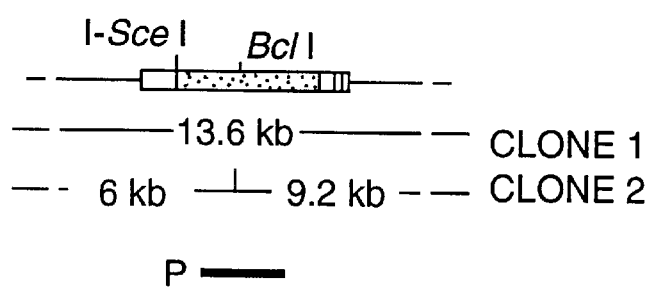
FIG. 27A

LOSS OF HETEROZYGOSITY
INTEGRATION OF ARTIFICIAL SITE OR
PRESENCE OF SPECIFIC SITE
I-*Sce* I
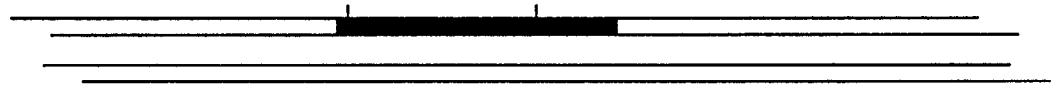
EXPRESSION OF I-*Sce* I AND SPECIFIC CLEVAGE
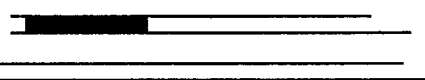
REPAIR OF THE DSB WITH THE OTHER CHROMATID
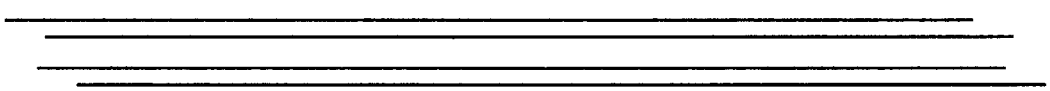
FIG. 28

ONE STEP REARRANGEMENT
INTEGRATION OF ARTIFICIAL SITE OR
PRESENCE OF SPECIFIC SITE
INACTIVE GENE
CHROMOSOME
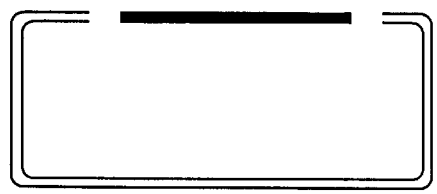
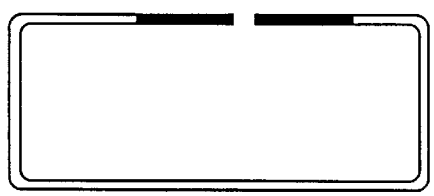
EXPRESSION OF I-Sce I ENZYME
AND
SPECIFIC CLEAVAGE OF THE DONOR PLASMID
INACTIVE GENE
CHROMOSOME
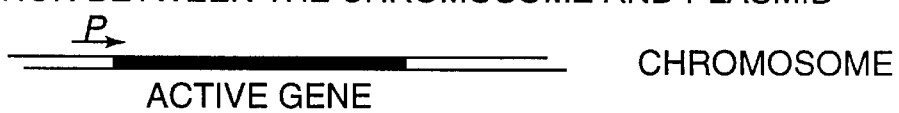
RECOMBINATION BETWEEN THE CHROMOSOME AND PLASMID
CHROMOSOME
ACTIVE GENE
FIG. 30

DUPLICATION OF A LOCUS
1. INSERTION OF I-Sce I SITE BY CLASSICAL GENE REPLACEMENT
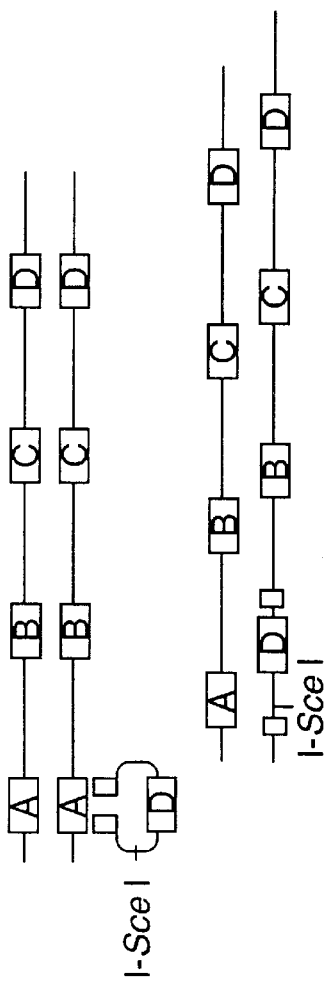
2. SPECIFIC CLEAVAGE BY I-Sce I ENZYME AND REPAIR OF THE BREAK BY HOMOLOGOUS SEQUENCES
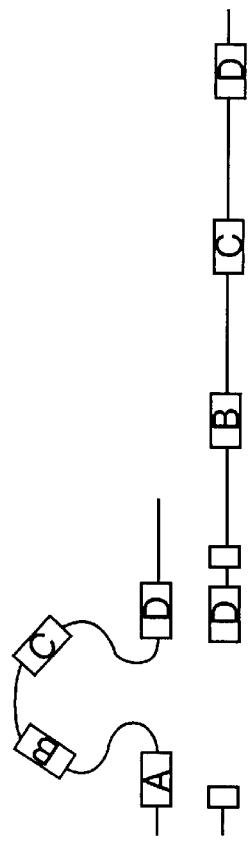
3. DUPLICATION OF THE TOTALITY OF THE LOCUS
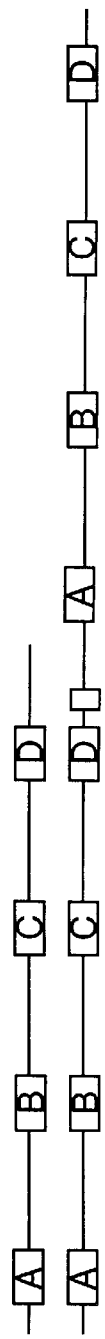
FIG. 31

DELETON OF A LOCUS
1 INSERTION OF TWO I-*Sce* I SITES FLANKING THE LOCUS
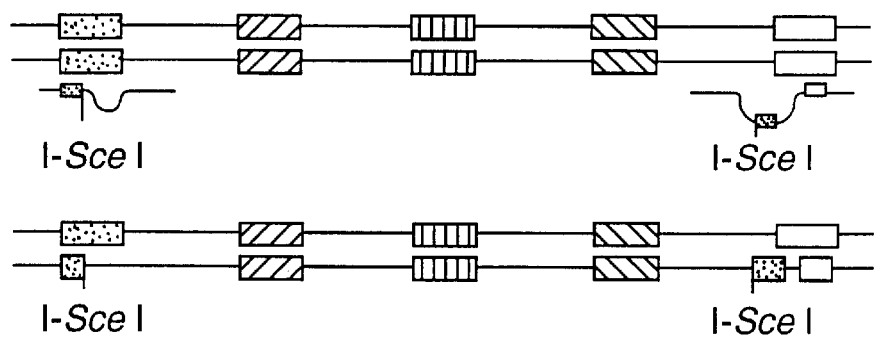
2 EXPRESSION OF THE ENZYME AND CLEAVAGE
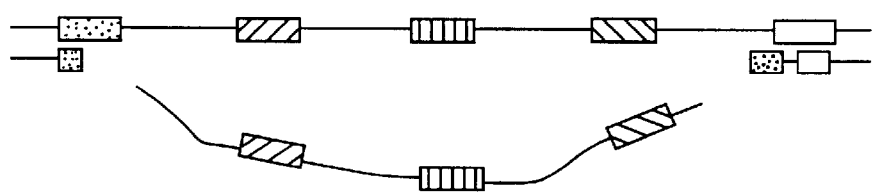
3 RECOMBINATION BETWEEN THE TWO ENDS
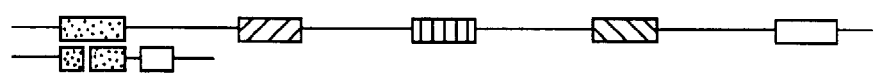
4 DELETION OF THE LOCUS
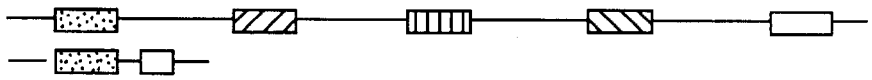
FIG. 32

NUCLEOTIDE SEQUENCE ENCODING THE ENZYME I-SCEI AND THE USES THEREOF

CROSS-REFERENCE TO RELATED APPLICATION

This is a continuation of application Ser. No. 08/336,241, filed Nov. 7, 1994 which is a continuation-in-part application of Ser. No. 07/971,160, filed Nov. 5, 1992, now U.S. Pat. No. 5,474,896 which is a continuation-in-part application of Ser. No. 07/879,689, filed May 5, 1992, now abandoned.

BACKGROUND OF THE INVENTION

This invention relates to a nucleotide sequence that encodes the restriction endonuclease I-SceI. This invention also relates to vectors containing the nucleotide sequence, cells transformed with the vectors, transgenic animals based on the vectors, and cell lines derived from cells in the animals. This invention also relates to the use of I-SceI for mapping eukaryotic genomes and for in vivo site directed genetic recombination.

The ability to introduce genes into the germ line of mammals is of great interest in biology. The propensity of mammalian cells to take up exogenously added DNA and to express genes included in the DNA has been known for many years. The results of gene manipulation are inherited by the offspring of these animals. All cells of these offspring inherit the introduced gene as part of their genetic make-up. Such animals are said to be transgenic.

Transgenic mammals have provided a means for studying gene regulation during embryogenesis and in differentiation, for studying the action of genes, and for studying the intricate interaction of cells in the immune system. The whole animal is the ultimate assay system for manipulated genes, which direct complex biological processes.

Transgenic animals can provide a general assay for functionally dissecting DNA sequences responsible for tissue specific or developmental regulation of a variety of genes. In addition, transgenic animals provide useful vehicles for expressing recombinant proteins and for generating precise animal models of human genetic disorders.

For a general discussion of gene cloning and expression in animals and animal cells, see Old and Primrose, "Principles of Gene Manipulation," Blackwell Scientific Publications, London (1989), page 255 et seq.

Transgenic lines, which have a predisposition to specific diseases and genetic disorders, are of great value in the investigation of the events leading to these states. It is well known that the efficacy of treatment of a genetic disorder may be dependent on identification of the gene defect that is the primary cause of the disorder. The discovery of effective treatments can be expedited by providing an animal model that will lead to the disease or disorder, which will enable the study of the efficacy, safety, and mode of action of treatment protocols, such as genetic recombination.

One of the key issues in understanding genetic recombination is the nature of the initiation step. Studies of homologous recombination in bacteria and fungi have led to the proposal of two types of initiation mechanisms. In the first model, a single-strand nick initiates strand assimilation and branch migration (Meselson and Radding 1975). Alternatively, a double-strand break may occur, followed by a repair mechanism that uses an uncleaved homologous sequence as a template (Resnick and Martin 1976). This latter model has gained support from the fact that integrative transformation in yeast is dramatically increased when the transforming plasmid is linearized in the region of chromosomal homology (Orr-Weaver, Szostak and Rothstein 1981) and from the direct observation of a double-strand break during mating type interconversion of yeast (Strathern et al. 1982). Recently, double-strand breaks have also been characterized during normal yeast meiotic recombination (Sun et al. 1989; Alani, Padmore and Kleckner 1990).

Several double-strand endonuclease activities have been characterized in yeast: HO and intron encoded endonucleases are associated with homologous recombination functions, while others still have unknown genetic functions (Endo-SceI, Endo-SceII) (Shibata et al. 1984; Morishima et al. 1990). The HO site-specific endonuclease initiates mating-type interconversion by making a double-strand break near the YZ junction of MAT (Kostriken et al. 1983). The break is subsequently repaired using the intact HML or HMR sequences and resulting in ectopic gene conversion. The HO recognition site is a degenerate 24 bp non-symmetrical sequence (Nickoloff, Chen, and Heffron 1986; Nickoloff, Singer and Heffron 1990). This sequence has been used as a "recombinator" in artificial constructs to promote intra- and intermolecular mitotic and meiotic recombination (Nickoloff, Chen and Heffron, 1986; Kolodkin, Klar and Stahl 1986; Ray et al. 1988, Rudin and Haber, 1988; Rudin, Sugarman, and Haber 1989).

The two-site specific endonucleases, I-SceI (Jacquier and Dujon 1985) and I-SceII (Delahodde et al. 1989; Wenzlau et al. 1989), that are responsible for intron mobility in mitochondria, initiate a gene conversion that resembles the HO-induced conversion (see Dujon 1989 for review). I-SceI, which is encoded by the optional intron Sc LSU.1 of the 21S rRNA gene, initiates a double-strand break at the intron insertion site (Macreadie et al. 1985; Dujon et al. 1985(ref. 7 and ref. A4); Colleaux et al. 1986(ref. 8)). The recognition site of I-SceI extends over an 18 bp non-symmetrical sequence (Colleaux et al. 1988). Although the two proteins are not obviously related by their structure (HO is 586 amino acids long while I-SceI is 235 amino acids long), they both generate 4 bp staggered cuts with 3'OH overhangs within their respective recognition sites. It has been found that a mitochondrial intron-encoded endonuclease, transcribed in the nucleus and translated in the cytoplasm, generates a double-strand break at a nuclear site. The repair events induced by I-SceI are identical to those initiated by HO.

In summary, there exists a need in the art for reagents and methods for providing transgenic animal models of human diseases and genetic disorders. The reagents can be based on the restriction enzyme I-SceI and the gene encoding this enzyme. In particular, there exists a need for reagents and methods for replacing a natural gene with another gene that is capable of alleviating the disease or genetic disorder.

SUMMARY OF THE INVENTION

Accordingly, this invention aids in fulfilling these needs in the art. Specifically, this invention relates to an isolated DNA encoding the enzyme I-SceI. The DNA has the following nucleotide sequence:

```
(SEQ ID NO: 1)  ATG CAT ATG AAA AAC ATC AAA AAA AAC CAG GTA ATG 2670
(SEQ ID NO: 2)   M   H   M   K   N   I   K   K   N   Q   V   M   12

2671 AAC CTC GGT CCG AAC TCT AAA CTG CTG AAA GAA TAC AAA TCC CAG CTG ATC GAA CTG AAC 2730
  13 N   L   G   P   N   S   K   L   L   K   E   Y   K   S   Q   L   I   E   L   N   32

2731 ATC GAA CAG TTC GAA GCA GGT ATC GGT CTG ATC CTG GGT GAT GCT TAC ATC CGT TCT CGT 2790
  33 I   E   Q   F   E   A   G   I   G   L   I   L   G   D   A   Y   I   R   S   R   52

2791 GAT GAA GGT AAA ACC TAC TGT ATG CAG TTC GAG TGG AAA AAC AAA GCA TAC ATG GAC CAC 2850
  53 D   E   G   K   T   Y   C   M   Q   F   E   W   K   N   K   A   Y   M   D   H   72

2851 GTA TGT CTG CTG TAC GAT CAG TGG GTA CTG TCC CCG CCG CAC AAA AAA GAA CGT GTT AAC 2910
  73 V   C   L   L   Y   D   Q   W   V   L   S   P   P   H   K   K   E   R   V   N   92

2911 CAC CTG GGT AAC CTG GTA ATC ACC TGG GGC GCC CAG ACT TTC AAA CAC CAA GCT TTC AAC 2970
  93 H   L   G   N   L   V   I   T   W   G   A   Q   T   F   K   H   Q   A   F   N   112

2971 AAA CTG GCT AAC CTG TTC ATC GTT AAC AAC AAA AAA ACC ATC CCG AAC AAC CTG GTT GAA 3030
 113 K   L   A   N   L   F   I   V   N   N   K   K   T   I   P   N   N   L   V   E   132

3031 AAC TAC CTG ACC CCG ATG TCT CTG GCA TAC TGG TTC ATG GAT GAT GGT GGT AAA TGG GAT 3090
 133 N   Y   L   T   P   M   S   L   A   Y   W   F   M   D   D   G   G   K   W   D   152

3091 TAC AAC AAA AAC TCT ACC AAC AAA TCG ATC GTA CTG AAC ACC CAG TCT TTC ACT TTC GAA 3150
 153 Y   N   K   N   S   T   N   K   S   I   V   L   N   T   Q   S   F   T   F   E   172

3151 GAA GGA GAA TAC CTG GTT AAG GGT CTG CGT AAC AAA TTC CAA CTG AAC TGT TAC GTA AAA 3210
 173 E   V   E   Y   L   V   K   G   L   R   N   K   F   Q   L   N   C   Y   V   K   192

3211 ATC AAC AAA AAC AAA CCG ATC ATC TAC ATC GAT TCT ATG TCT TAC CTG ATC TTC TAC AAC 3270
 193 I   N   K   N   K   P   I   I   Y   I   D   S   M   S   Y   L   I   F   Y   N   212

3271 CTG ATC AAA CCG TAC CTG ATC CCG CAG ATG ATG TAC AAA CTG CCG AAC ACT ATC TCC TCC 3330
 213 L   I   K   P   Y   L   I   P   Q   M   M   Y   K   L   P   N   T   I   S   S   232

3331 GAA ACT TTC CTG AAA TAA
 233 E   T   F   L   K   *
```

This invention also relates to a DNA sequence comprising a promoter operatively linked to the DNA sequence of the invention encoding the enzyme I-SceI.

This invention further relates to an isolated RNA complementary to the DNA sequence of the invention encoding the enzyme I-SceI and to the other DNA sequences described herein.

In another embodiment of the invention, a vector is provided. The vector comprises a plasmid, bacteriophage, or cosmid vector containing the DNA sequence of the invention encoding the enzyme I-SceI.

In addition, this invention relates to E. coli or eukaryotic cells transformed with a vector of the invention.

Also, this invention relates to transgenic animals containing the DNA sequence encoding the enzyme I-SceI and cell lines cultured from cells of the transgenic animals.

In addition, this invention relates to a transgenic organism in which at least one restriction site for the enzyme I-SceI has been inserted in a chromosome of the organism.

Further, this invention relates to a method of genetically mapping a eukaryotic genome using the enzyme I-SceI.

This invention also relates to a method for in vivo site directed recombination in an organism using the enzyme I-SceI.

BRIEF DESCRIPTION OF THE DRAWINGS

This invention will be more fully described with reference to the drawings in which:

FIG. 1 depicts the universal code equivalent of the mitochondrial I-SceI gene (SEQ ID NOS 3 and 4).

FIG. 2 depicts the nucleotide sequence of the invention encoding the enzyme I-SceI and the amino acid sequence of the natural I-SceI enzyme (SEQ ID NOS 5 and 2).

FIG. 4 is the nucleotide sequence and deduced amino acid sequence of a region of plasmid pSCM525. The nucleotide sequence of the invention encoding the enzyme I-SceI is enclosed in the box (SEQ ID NOS:9 through 16).

FIG. 5 depicts variations around the amino acid sequence of the enzyme I-SceI (SEQ ID NO:2).

FIG. 6 shows Group I intron encoding endonucleases and related endonucleases (SEQ ID NOS:17 through 44).

FIGS. 10A and 10B show the nucleotide sequence and restriction sites of regions of the plasmid pAF100 (SEQ ID NOS:45 through 50)

FIG. 16 depicts mapping of the I-SceI sites of transgenic yeast strains by hybridization with left end and right end probes of chromosome XI. Chromosomes from FY1679 (control) and the seven transgenic yeast strains were digested with I-SceI. Transgenic strains were placed in order as explained in FIG. 15. Electrophoresis conditions were as in FIG. 14. $^{32}$P labelled cosmids pUKG040 and pUKG066 were used as left end and right end probes, respectively.

FIG. 20 (parts a–e). Experimental design for the detection of HR induced by I-SceI. a) Maps of the 7.5 kb tk–PhleoLacZ retrovirus (G-MtkPL) and of the 6.0 kb PhleoLacZ retrovirus (G-MPL), SA is splice acceptor site. G-MtkPL sequences (from G-MtkPL virus) contains PhleoLacZ fusion gene for positive selection of infected cells (in phleomycin-containing medium) and tk gene for negative selection (in gancyclovir-containing medium). G-MPL sequences (from G-MPL virus) contains only PhleoLacZ sequences. b) Maps of proviral structures following retroviral integration of G-MtkPL and G-MPL. I-Sce I PhleoLacZ LTR duplicates, placing I-Sce I PhleoLacZ sequences in the 5' LTR. The virus vector (which functions as a promoter trap) is transcribed (arrow) by a flanking cellular promoter, P. c) I-Sce I creates two double strand breaks (DSBs) in host DNA liberating the central segment and leaving broken chromosome ends that can pair with the donor plasmid, pVRneo (d). e) Expected recombinant locus following HR.

FIG. 25 (parts a–c). Types of recombination events induced by I-Sce I DSBs, a) Schematic drawing of the structure of the recombination substrate. The G-MtkPL has provirus two LTRs, each containing an I-Sce I recognition site and a PhleoLacZ gene. The LTRs are separated by viral sequences containing the tk gene. The phenotype of G-MtkPL containing cells is Phleo$^R$, GIs$^s$, β-Gal±b) Possible modes of intra-chromosomal recombination. 1) The I-Sce I endonuclease cuts the I-Sce I site in the 5'LTR. The 5' part of U3 of the 5'LTR can pair and recombine with it homologous sequence in the 3'LTR (by SSA). 2) The I-Sce I endonuclease cuts the I-Sce I site in the 3'LTR. The 3' part of U3 of the 3'LTR can pair and recombine with its homologous sequence in the 5'LTR (by SSA). 3) The I-Sce I endonuclease cuts I-Sce I sites in the two LTRs. The two free ends can relegate (by an end-joining mechanism). The resulting recombination product in each of the three models is a solitary LTR (see right side). No modification would occur in the cellular sequences flanking the integration site. c) The I-Sce I endonuclease cuts the I-Sce I sites in the two LTRs. The two free ends can be repaired (by a gap repair mechanism) using the homologous chromosome. On the right, the resulting recombination product is the deletion of the proviral integration locus.

Heavy bar is $^{32}$P radiolabelled LacZ probe (P)

FIG. 28. FIG. 28 is a diagram illustrating the loss of heterozygosity by the insertion or presence of an I-Sce I site, expression of the enzyme I-Sce I, cleavage at the site, and repair of the double strand break at the site with the corresponding chromatid.

Figure 29:
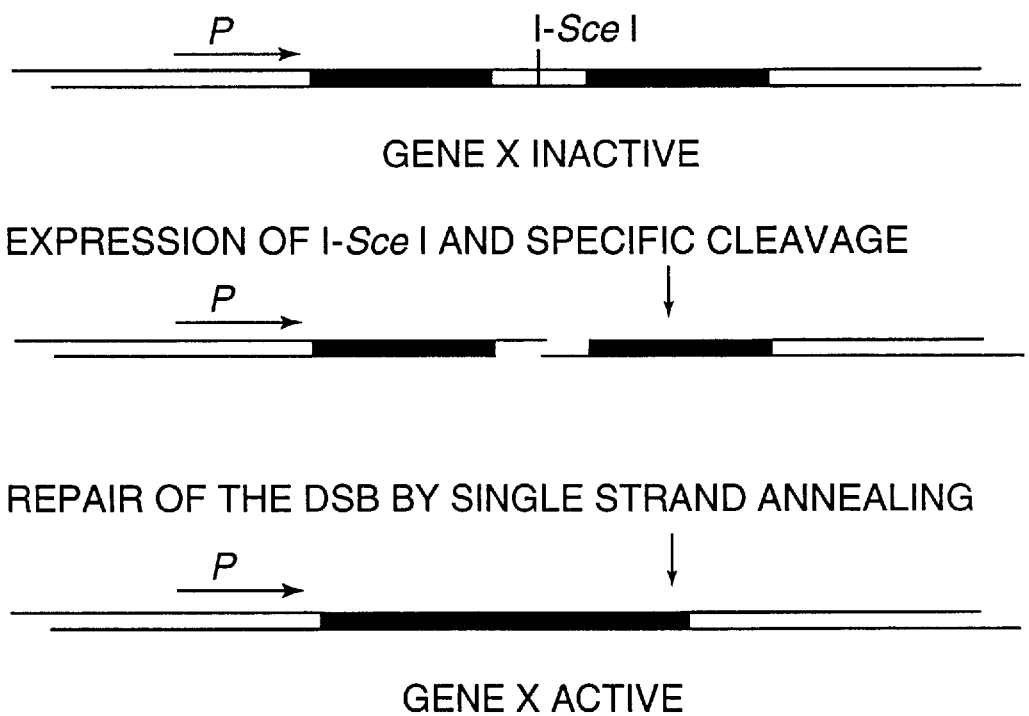

FIG. 29. FIG. 29 is a diagram illustrating conditional activation of a gene. An I-Sce I site is integrated between tandem repeats, and the enzyme I-Sce I is expressed. The enzyme cleaves the double stranded DNA at the I-Sce I site. The double strand break is repaired by single stand annealing, yielding an active gene.

FIG. 30. FIG. 30 is a diagram illustrating one step rearrangement of a gene by integration of an I-Sce I site or by use of an I-Sce I site present in the gene. A plasmid having either one I-Sce I site within an inactive gene, or two I-Sce I sites at either end of an active gene without a promoter, is introduced into the cell. The cell contains an inactive form of the corresponding gene. The enzyme I-Sce I cuts the plasmid at the I-Sce I sites, and recombination between the chromosome and the plasmid yields an active gene replacing the inactive gene.

FIG. 31. FIG. 31 is a diagram illustrating the duplication of a locus. An I-Sce I site and a distal part of the locus are inserted into the gene by classical gene replacement. The I-Sce I site is cleaved by I-Sce I enzyme, and the break is repaired by homologous sequences. This results in duplication of the entire locus.

FIG. 32. FIG. 30 is a diagram illustrating the deletion of a locus. Two I-Sce I sites are added to flank the locus to be deleted. The I-Sce I enzyme is expressed, and the sites are cleaved. The two remaining ends recombine, deleting the locus between the two I-Sce I sites.

Figure 33:
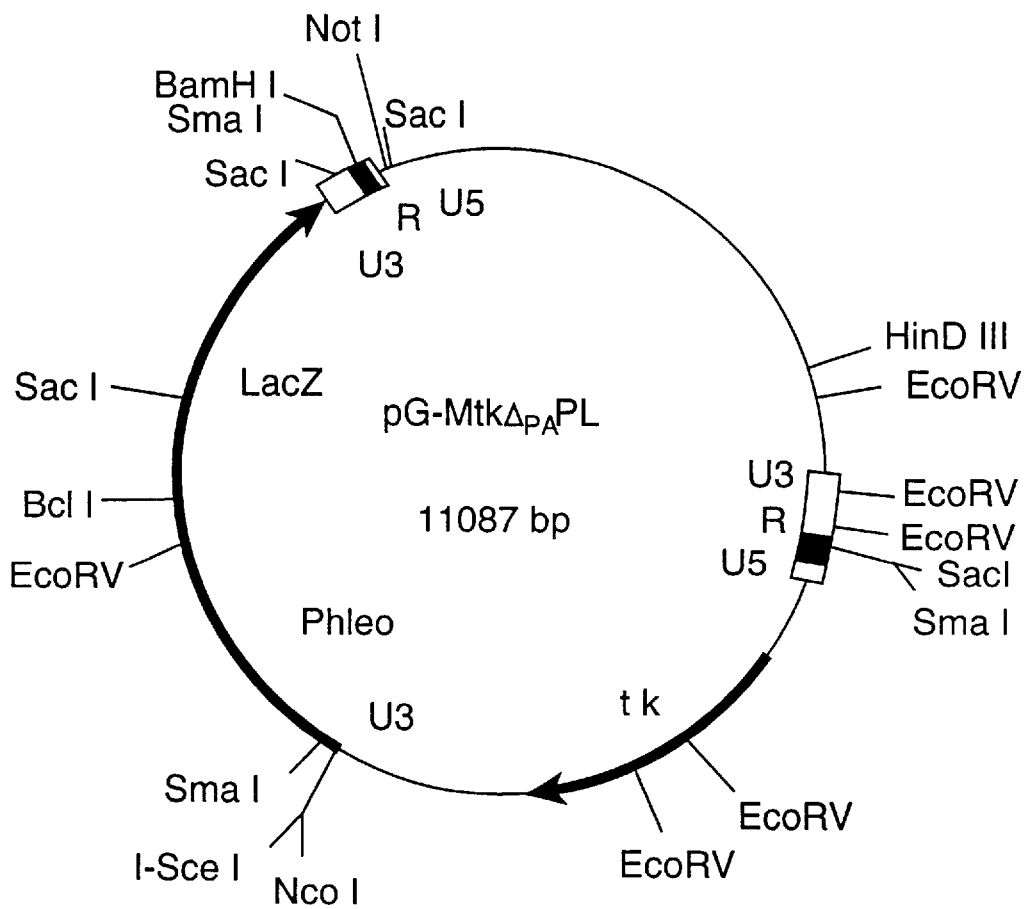

FIG. 33. FIG. 33 is a diagram of plasmid pG-MtkΔPAPL showing the restriction sites. The plasmid is constructed by deletion of the polyadenylation region of the tk gene from the pGMtkPL plasmid.

DETAILED DESCRIPTION OF THE PREFERRED EMBODIMENTS

The genuine mitochondrial gene (ref. 8) cannot be expressed in *E. coli*, yeast or other organisms due to the peculiarities of the mitochondrial genetic code. A "universal code equivalent" has been constructed by in vitro site-directed mutagenesis. Its sequence is given in FIG. 1. Note that all non-universal codons (except two CTN) have been replaced together with some codons extremely rare in *E. coli*.

The universal code equivalent has been successfully expressed in *E. coli* and determines the synthesis of an active enzyme. However, expression levels remained low due to the large number of codons that are extremely rare in *E. coli*. Expression of the "universal code equivalent" has been detected in yeast.

To optimize gene expression in heterologous systems, a synthetic gene has been designed to encode a protein with the genuine amino acid sequence of I-SceI using, for each codon, that most frequently used in *E. coli*. The sequence of the synthetic gene is given in FIG. 2. The synthetic gene was constructed in vitro from eight synthetic oligonucleotides with partial overlaps. Oligonucleotides were designed to allow mutual priming for second strand synthesis by Klenow polymerase when annealed by pairs. The elongated pairs were then ligated into plasmids. Appropriately placed restriction sites within the designed sequence allowed final assembly of the synthetic gene by in vitro ligation. The synthetic gene has been successfully expressed in both *E. coli* and yeast.

1. I-SceI Gene Sequence

This invention relates to an isolated DNA sequence encoding the enzyme I-SceI. The enzyme I-SceI is an endonuclease. The properties of the enzyme (ref. 14) are as follows:

I-SceI is a double-stranded endonuclease that cleaves DNA within its recognition site. I-SceI generates a 4 bp staggered cut with 3'OH overhangs.

Substrate: Acts only on double-stranded DNA. Substrate DNA can be relaxed or negatively supercoiled.

Cations: Enzymatic activity requires $Mg^{++}$ (8 mM is optimum). $Mn^{++}$ can replace $Mg^{++}$, but this reduces the stringency of recognition.

Optimum conditions for activity: high pH (9 to 10), temperature 20°–40° C., no monovalent cations.

Enzyme stability: I-SceI is unstable at room temperature. The enzyme-substrate complex is more stable than the enzyme alone (presence of recognition sites stabilizes the enzyme.)

The enzyme I-SceI has a known recognition site. (ref. 14.) The recognition site of I-SceI is a non-symmetrical sequence that extends over 18 bp as determined by systematic mutational analysis. The sequence reads: (arrows indicate cuts)

5' TAGGGATAA↓CAGGGTAAT 3' (SEQ ID NO:51)

3' ATCCC↑TATTGTCCCATTA 5' (SEQ ID NO:52) The recognition site corresponds, in part, to the upstream exon and, in part, to the downstream exon of the intron plus form of the gene.

The recognition site is partially degenerate: single base substitutions within the 18 bp long sequence result in either complete insensitivity or reduced sensitivity to the enzyme, depending upon position and nature of the substitution.

The stringency of recognition has been measured on:

1- mutants of the site.

2- the total yeast genome (*Saccharomyces cerevisiae*, genome complexity is $1.4 \times 10^7$ bp). Data are unpublished.

Results are

Figure 3:
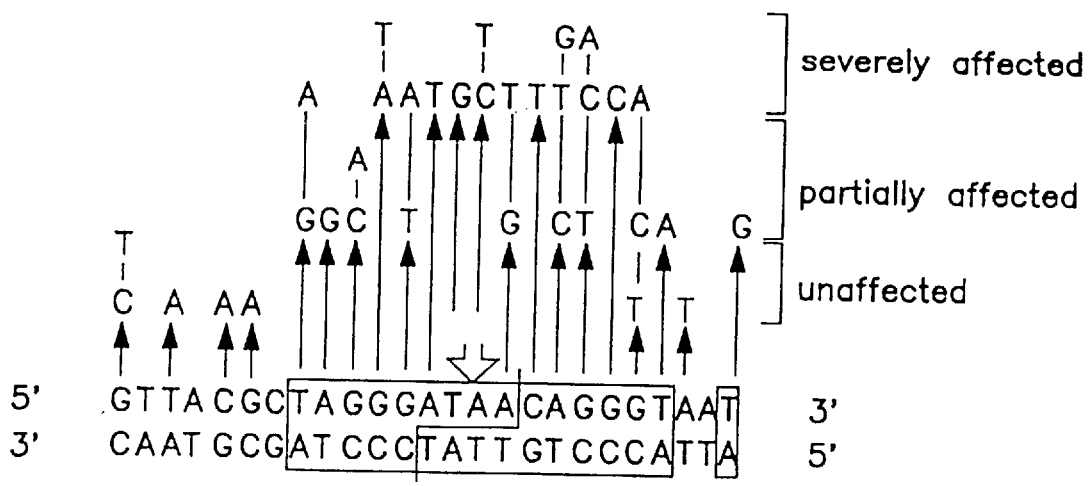
FIG. 3 depicts the I-SceI recognition sequence and indicates possible base mutations in the recognition site and the effect of such mutations on stringency of recognition (SEQ ID NOS. 6, 7, and 8).

1- Mutants of the site: As shown in FIG. 3, there is a general shifting of stringency, i.e., mutants severely affected in $Mg^{++}$ become partially affected in $Mn^{30+}$, mutants partially affected in $Mg^{++}$ become unaffected in $Mn^{++}$.

2- Yeast: In magnesium conditions, no cleavage is observed in normal yeast. In the same condition, DNA from transgenic yeasts is cleaved to completion at the artificially inserted I-SceI site and no other cleavage site can be detected. If magnesium is replaced by manganese, five additional cleavage sites are revealed in the entire yeast genome, none of which is cleaved to completion. Therefore, in manganese the enzyme reveals an average of 1 site for ca. 3 millions based pairs ($5/1.4 \times 10^7$ bp).

Definition of the recognition site: important bases are indicated in FIG. 3. They correspond to bases for which severely affected mutants exist. Notice however that:

1- All possible mutations at each position have not been determined; therefore a base that does not correspond to a severely affected mutant may still be important if another mutant was examined at this very same position.

2- There is no clear-cut limit between a very important base (all mutants are severely affected) and a moderately important base (some of the mutants are severely affected). There is a continuum between excellent substrates and poor substrates for the enzyme.

The expected frequency of natural I-SceI sites in a random DNA sequence is, therefore, equal to $(0.25)^{-18}$ or $(1.5 \times 10^{-11})$. In other words, one should expect one natural site for the equivalent of ca. 20 human genomes, but the frequency of degenerate sites is more difficult to predict.

I-SceI belongs to a "degenerate" subfamily of the two-dodecapeptide family. Conserved amino acids of the dodecapeptide motifs are required for activity. In particular, the aspartic residues at positions 9 of the two dodecapeptides cannot be replaced, even with glutamic residues. It is likely that the dodecapeptides form the catalytic site or part of it.

Consistent with the recognition site being non-symmetrical, it is likely that the endonucleolytic activity of I-SceI requires two successive recognition steps: binding of the enzyme to the downstream half of the site (corresponding to the downstream exon) followed by binding of the enzyme to the upstream half of the site (corresponding to the upstream exon). The first binding is strong, the second is weaker, but the two are necessary for cleavage of DNA. In vitro, the enzyme can bind the downstream exon alone as well as the intron-exon junction sequence, but no cleavage results.

The evolutionarily conserved dodecapeptide motifs of intron-encoded I-SceI are essential for endonuclease activity. It has been proposed that the role of these motifs is to properly position the acidic amino acids with respect to the DNA sequence recognition domains of the enzyme for the catalysis of phosphodiester bond hydrolysis (ref. P3).

The nucleotide sequence of the invention, which encodes the natural I-SceI enzyme is shown in FIG. 2. The nucleotide sequence of the gene of the invention was derived by dideoxynucleotide sequencing. The base sequences of the nucleotides are written in the 5'→3' direction. Each of the letters shown is a conventional designation for the following nucleotides:

| | |
|---|---|
| A | Adenine |
| G | Guanine |
| T | Thymine |
| C | Cytosine. |

It is preferred that the DNA sequence encoding the enzyme I-SceI be in a purified form. For instance, the sequence can be free of human blood-derived proteins, human serum proteins, viral proteins, nucleotide sequences encoding these proteins, human tissue, human tissue components, or combinations of these substances. In addition, it is preferred that the DNA sequence of the invention is free of extraneous proteins and lipids, and adventitious microorganisms, such as bacteria and viruses. The essentially purified and isolated DNA sequence encoding I-SceI is especially useful for preparing expression vectors.

Figure 4B:
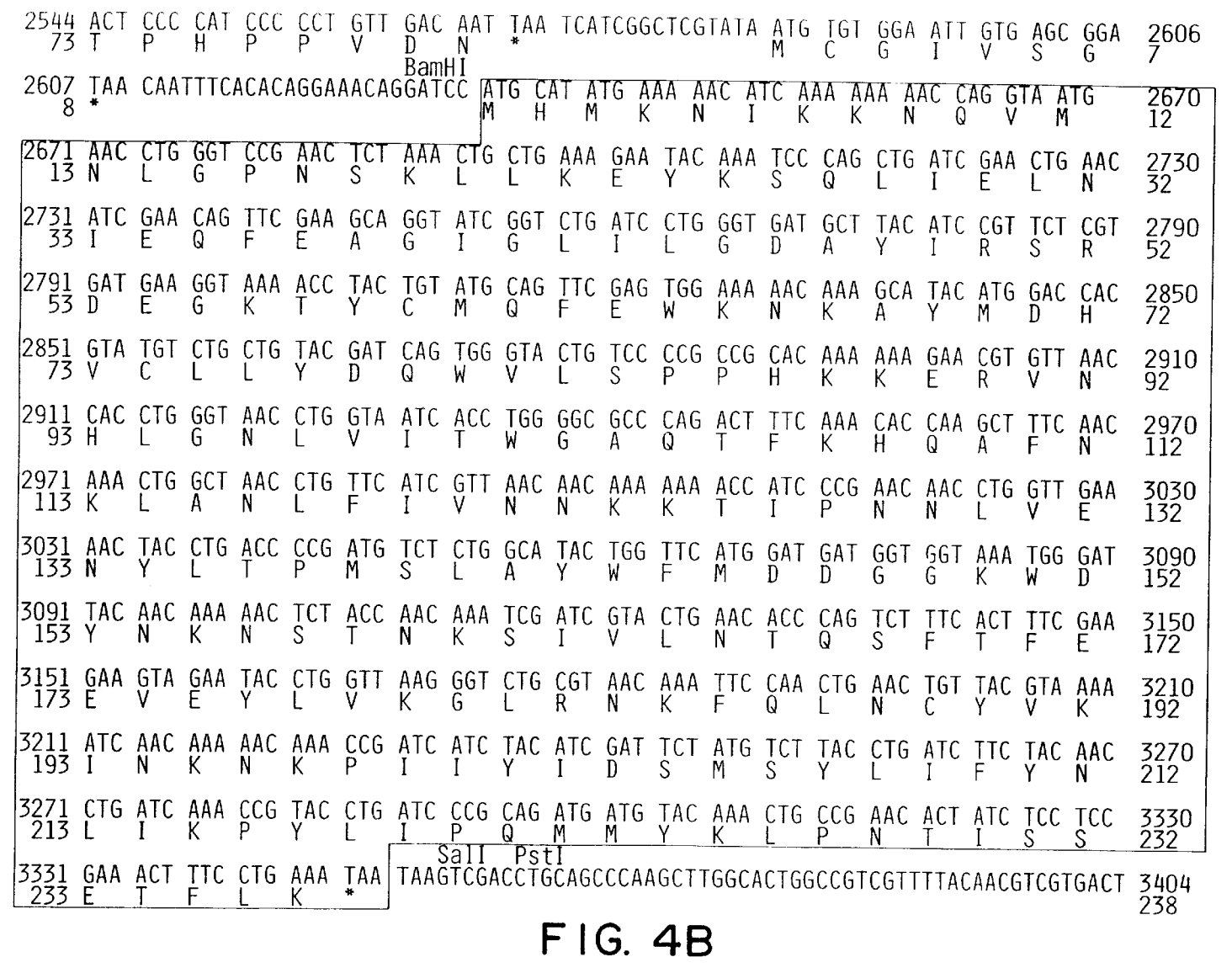

Plasmid pSCM525 is a pUC12 derivative, containing an artificial sequence encoding the DNA sequence of the invention. The nucleotide sequence and deduced amino acid sequence of a region of plasmid pSCM525 is shown in FIG. 4. The nucleotide sequence of the invention encoding I-SceI is enclosed in the box. The artificial gene is a BamHI-SalI piece of DNA sequence of 723 base pairs, chemically synthesized and assembled. It is placed under tac promoter control. The DNA sequence of the artificial gene differs from the natural coding sequence or its universal code equivalent described in Cell (1986), Vol. 44, pages 521–533. However, the translation product of the artificial gene is identical in sequence to the genuine omega-endonuclease except for the addition of a Met-His at the N-terminus. It will be understood that this modified endonuclease is within the scope of this invention.

Plasmid pSCM525 can be used to transform any suitable *E. coli* strain and transformed cells become ampicillin-resistant. Synthesis of the omega-endonuclease is obtained by addition of I.P.T.G. or an equivalent inducer of the lactose operon system.

A plasmid identified as pSCM525 containing the enzyme I-SceI was deposited in *E. coli* strain TG1 with the Collection Nationale de Cultures de Microorganismes (C.N.C.M.) of Institut Pasteur in Paris, France on Nov. 22, 1990, under culture collection deposit Accession No. I-1014. The nucleotide sequence of the invention is thus available from this deposit.

The gene of the invention can also be prepared by the formation of 3'→5' phosphate linkages between nucleoside units using conventional chemical synthesis techniques. For example, the well-known phosphodiester, phosphotriester, and phosphite triester techniques, as well as known modifications of these approaches, can be employed. Deoxyribonucleotides can be prepared with automatic synthesis machines, such as those based on the phosphoramidite approach. Oligo- and polyribonucleotides can also be obtained with the aid of RNA ligase using conventional techniques.

This invention of course includes variants of the DNA sequence of the invention exhibiting substantially the same properties as the sequence of the invention. By this it is meant that DNA sequences need not be identical to the sequence disclosed herein. Variations can be attributable to single or multiple base substitutions, deletions, or insertions or local mutations involving one or more nucleotides not substantially detracting from the properties of the DNA sequence as encoding an enzyme having the cleavage properties of the enzyme I-SceI.

FIG. 5 depicts some of the variations that can be made around the I-SceI amino acid sequence. It has been demonstrated that the following positions can be changed without affecting enzyme activity:

positions −1 and −2 are not natural. The two amino acids are added due to cloning strategies.

positions 1 to 10: can be deleted.

position 36: G is tolerated.

position 40: M or V are tolerated.

position 41: S or N are tolerated.

position 43: A is tolerated.

position 46: V or N are tolerated.

position 91: A is tolerated.

positions 123 and 156: L is tolerated.

position 223: A and S are tolerated.

It will be understood that enzymes containing these modifications are within the scope of this invention.

Changes to the amino acid sequence in FIG. 5 that have been demonstrated to affect enzyme activity are as follows:

position 19: L to S position 38: I to S or N position 39: G to D or R position 40: L to Q position 42: L to R position 44: D to E, G or H position 45: A to E or D position 46: Y to D position 47: I to R or N position 80: L to S position 144: D to E position 145: D to E position 146: G to E position 147: G to S It will also be understood that the present invention is intended to encompass fragments of the DNA sequence of the invention in purified form, where the fragments are capable of encoding enzymatically active I-SceI.

The DNA sequence of the invention coding for the enzyme I-SceI can be amplified in the well known polymerase chain reaction (PCR), which is useful for amplifying all or specific regions of the gene. See e.g., S. Kwok et al., J. Virol., 61:1690–1694 (1987); U.S. Pat. No. 4,683,202; and U.S. Pat. No. 4,683,195. More particularly, DNA primer pairs of known sequence positioned 10–300 base pairs apart that are complementary to the plus and minus strands of the DNA to be amplified can be prepared by well known techniques for the synthesis of oligonucleotides. One end of each primer can be extended and modified to create restriction endonuclease sites when the primer is annealed to the DNA. The PCR reaction mixture can contain the DNA, the DNA primer pairs, four deoxyribonucleoside triphosphates, $MgCl_2$, DNA polymerase, and conventional buffers. The DNA can be amplified for a number of cycles. It is generally possible to increase the sensitivity of detection by using a multiplicity of cycles, each cycle consisting of a short period of denaturation of the DNA at an elevated temperature, cooling of the reaction mixture, and polymerization with the DNA polymerase. Amplified sequences can be detected by the use of a technique termed oligomer restriction (OR). See, R. K. Saiki et al., Bio/Technology 3:1008–1012 (1985).

The enzyme I-SceI is one of a number of endonucleases with similar properties. Following is a listing of related enzymes and their sources.

Group I intron encoded endonucleases and related enzymes are listed below with references. Recognition sites are shown in FIG. 6.

| Enzyme | Encoded by | Ref |
| --- | --- | --- |
| I-SceI | Sc LSU-1 intron | this work |
| I-SceII | Sc cox1–4 intron | Sargueil et al., NAR (1990) 18, 5659–5665 |
| I-SceIII | Sc cox1–3 intron | Sargueil et al., MGG (1991) 225, 340–341 |
| I-SceIV | Sc cox1–5a intron | Seraphin et al. (1992) in press |
| I-ceuI | Ce LSU-5 intron | Marshall, Lemieux Gene (1991) 104, 241–245 |
| I-CreI | Cr LSU-1 intron | Rochaix (unpublished) |
| I-PpoI | Pp LSU-3 intron | Muscarella et al., MCB (1990) 10, 3386–3396 |
| I-TevI | T4 td-1 intron | Chu et al., PNAS (1990) 87, 3574–3578 and Bell-Pedersen et al. NAR (1990) 18, 3763–3770. |
| I-TevII | T4 sunY intron | Bell-Pedersen et al. NAR (1990) 18, 3763–3770. |
| I-TevIII | RB3 nrdB-1 intron | Eddy, Gold, Genes Dev. (1991) 5, 1032–1041 |
| HO | HO yeast gene | Nickoloff et al., MCB (1990) 10, 1174–1179 |
| Endo SceI | RF3 yeast mito. gene | Kawasaki et al., JBC (1991) 266, 5342–5347 |

Putative new enzymes (genetic evidence but no activity as yet) are I-CsmI from cytochrome b intron 1 of *Chlamydomonas smithii* mitochondria (ref. 15), I-PanI from cytochrome b intron 3 of *Podospora anserina* mitochondria (D. J. Cummings et al., "DNA Sequence Analysis of the Apocytochrome b Gene of *Podospora anserina*: A New Family of Intronic Open Reading", Current Genetics 16:407–418 (1989)), and probably enzymes encoded by introns Nc nd1.1 and Nc cob.! from *Neurospora crassa*.

The I-endonucleases can be classified as follows:

Class I: Two dodecapeptide motifs, 4 bp staggered cut with 3' OH overhangs, cut internal to recognition site

| Subclass "I-SceI" | Other subclasses |
|---|---|
| I-SceI | I-SceII |
| I-SceIV | I-SceIII |
| I-CsmI | I-CeuI (only one dodecapeptide motif) |
| I-PanI | I-CreI (only one dodecapeptide motif) |
| | HO |
| | TFP1-408 (HO homolog) |
| | Endo SceI |

Class II: GIY-($N_{10-11}$) YIG motif, 2 bp staggered cut with 3' OH overhangs, cut external to recognition site:
I-TevI Class III: no typical structural motifs, 4 bp staggered cut with 3' OH overhangs, cut internal to recognition site:
I-PpoI Class IV: no typical structural motifs, 2 bp staggered cut with 3' OH overhangs, cut external to recognition site:
I-TevII Class V: no typical structural motifs, 2 bp staggered cut with 5' OH overhangs:
I-TevIII.

2. Nucleotide Probes Containing the I-SceI Gene of The Invention

The DNA sequence of the invention coding for the enzyme I-SceI can also be used as a probe for the detection of a nucleotide sequence in a biological material, such as tissue or body fluids. The probe can be labeled with an atom or inorganic radical, most commonly using a radionuclide, but also perhaps with a heavy metal. Radioactive labels include $^{32}P$, $^{3}H$, $^{14}C$, or the like. Any radioactive label can be employed, which provides for an adequate signal and has sufficient half-life. Other labels include ligands that can serve as a specific binding member to a labeled antibody, fluorescers, chemiluminescers, enzymes, antibodies which can serve as a specific binding pair member for a labeled ligand, and the like. The choice of the label will be governed by the effect of the label on the rate of hybridization and binding of the probe to the DNA or RNA. It will be necessary that the label provide sufficient sensitivity to detect the amount of DNA or RNA available for hybridization.

When the nucleotide sequence of the invention is used as a probe for hybridizing to a gene, the nucleotide sequence is preferably affixed to a water insoluble solid, porous support, such as nitrocellulose paper. Hybridization can be carried out using labeled polynucleotides of the invention and conventional hybridization reagents. The particular hybridization technique is not essential to the invention.

The amount of labeled probe present in the hybridization solution will vary widely, depending upon the nature of the label, the amount of the labeled probe which can reasonably bind to the support, and the stringency of the hybridization. Generally, substantial excesses of the probe over stoichiometric will be employed to enhance the rate of binding of the probe to the fixed DNA.

Various degrees of stringency of hybridization can be employed. The more severe the conditions, the greater the complementarity that is required for hybridization between the probe and the polynucleotide for duplex formation. Severity can be controlled by temperature, probe concentration, probe length, ionic strength, time, and the like. Conveniently, the stringency of hybridization is varied by changing the polarity of the reactant solution. Temperatures to be employed can be empirically determined or determined from well known formulas developed for this purpose.

3. Nucleotide Sequences Containing the Nucleotide Sequence Encoding I-SceI

This invention also relates to the DNA sequence of the invention encoding the enzyme I-SceI, wherein the nucleotide sequence is linked to other nucleic acids. The nucleic acid can be obtained from any source, for example, from plasmids, from cloned DNA or RNA, or from natural DNA or RNA from any source, including prokaryotic and eukaryotic organisms. DNA or RNA can be extracted from a biological material, such as biological fluids or tissue, by a variety of techniques including those described by Maniatis et al., *Molecular Cloning: A Laboratory Manual*, Cold Spring Harbor Laboratory, New York (1982). The nucleic acid will generally be obtained from a bacteria, yeast, virus, or a higher organism, such as a plant or animal. The nucleic acid can be a fraction of a more complex mixture, such as a portion of a gene contained in whole human DNA or a portion of a nucleic acid sequence of a particular microorganism. The nucleic acid can be a fraction of a larger molecule or the nucleic acid can constitute an entire gene or assembly of genes. The DNA can be in a single-stranded or double-stranded form. If the fragment is in single-stranded form, it can be converted to double-stranded form using DNA polymerase according to conventional techniques.

The DNA sequence of the invention can be linked to a structural gene. As used herein, the term "structural gene" refers to a DNA sequence that encodes through its template or messenger mRNA a sequence of amino acids characteristic of a specific protein or polypeptide. The nucleotide sequence of the invention can function with an expression control sequence, that is, a DNA sequence that controls and regulates expression of the gene when operatively linked to the gene.

4. Vectors Containing the Nucleotide Sequence of the Invention

This invention also relates to cloning and expression vectors containing the DNA sequence of the invention coding for the enzyme I-SceI.

More particularly, the DNA sequence encoding the enzyme can be ligated to a vehicle for cloning the sequence. The major steps involved in gene cloning comprise procedures for separating DNA containing the gene of interest from prokaryotes or eukaryotes, cutting the resulting DNA fragment and the DNA from a cloning vehicle at specific sites, mixing the two DNA fragments together, and ligating the fragments to yield a recombinant DNA molecule. The recombinant molecule can then be transferred into a host cell, and the cells allowed to replicate to produce identical cells containing clones of the original DNA sequence.

The vehicle employed in this invention can be any double-stranded DNA molecule capable of transporting the nucleotide sequence of the invention into a host cell and capable of replicating within the cell. More particularly, the vehicle must contain at least one DNA sequence that can act as the origin of replication in the host cell. In addition, the vehicle must contain two or more sites for insertion of the DNA sequence encoding the gene of the invention. These sites will ordinarily correspond to restriction enzyme sites at which cohesive ends can be formed, and which are complementary to the cohesive ends on the promoter sequence to be ligated to the vehicle. In general, this invention can be carried out with plasmid, bacteriophage, or cosmid vehicles having these characteristics.

The nucleotide sequence of the invention can have cohesive ends compatible with any combination of sites in the vehicle. Alternatively, the sequence can have one or more blunt ends that can be ligated to corresponding blunt ends in the cloning sites of the vehicle. The nucleotide sequence to be ligated can be further processed, if desired, by successive exonuclease deletion, such as with the enzyme Bal 31. In the event that the nucleotide sequence of the invention does not contain a desired combination of cohesive ends, the sequence can be modified by adding a linker, an adaptor, or homopolymer tailing.

It is preferred that plasmids used for cloning nucleotide sequences of the invention carry one or more genes responsible for a useful characteristic, such as a selectable marker, displayed by the host cell. In a preferred strategy, plasmids having genes for resistance to two different drugs are chosen. For example, insertion of the DNA sequence into a gene for an antibiotic inactivates the gene and destroys drug resistance. The second drug resistance gene is not affected when cells are transformed with the recombinants, and colonies containing the gene of interest can be selected by resistance to the second drug and susceptibility to the first drug. Preferred antibiotic markers are genes imparting chloramphenicol, ampicillin, or tetracycline resistance to the host cell.

A variety of restriction enzymes can be used to cut the vehicle. The identity of the restriction enzyme will generally depend upon the identity of the ends on the DNA sequence to be ligated and the restriction sites in the vehicle. The restriction enzyme is matched to the restriction sites in the vehicle, which in turn is matched to the ends on the nucleic acid fragment being ligated.

The ligation reaction can be set up using well known techniques and conventional reagents. Ligation is carried out with a DNA ligase that catalyzes the formation of phosphodiester bonds between adjacent 5'-phosphate and the free 3'-hydroxy groups in DNA duplexes. The DNA ligase can be derived from a variety of microorganisms. The preferred DNA ligases are enzymes from *E. coli* and bacteriophage T4. T4 DNA ligase can ligate DNA fragments with blunt or sticky ends, such as those generated by restriction enzyme digestion. *E. coli* DNA ligase can be used to catalyze the formation of phosphodiester bonds between the termini of duplex DNA molecules containing cohesive ends.

Cloning can be carried out in prokaryotic or eukaryotic cells. The host for replicating the cloning vehicle will of course be one that is compatible with the vehicle and in which the vehicle can replicate. When a plasmid is employed, the plasmid can be derived from bacteria or some other organism or the plasmid can be synthetically prepared. The plasmid mid can replicate independently of the host cell chromosome or an integrative plasmid (episome) can be employed. The plasmid can make use of the DNA replicative enzymes of the host cell in order to replicate or the plasmid can carry genes that code for the enzymes required for plasmid replication A number of different plasmids can be employed in practicing this invention.

The DNA sequence of the invention encoding the enzyme I-SceI can also be ligated to a vehicle to form an expression vector. The vehicle employed in this case is one in which it is possible to express the gene operatively linked to a promoter in an appropriate host cell. It is preferable to employ a vehicle known for use in expressing genes in *E. coli* yeast, or mammalian cells. These vehicles include, for example, the following *E. coli* expression vectors:

pSCM525, which is an *E. coli* expression vector derived from pUC12 by insertion of a tac promoter and the synthetic gene for I-SceI. Expression is induced by IPTG.

pGEXω6, which is an *E. coli* expression vector derived from pGEX in which the synthetic gene from pSCM525 for I-SceI is fused with the glutathione S transferase gene, producing a hybrid protein. The hybrid protein possesses the endonuclease activity.

pDIC73, which is an *E. coli* expression vector derived from pET-3C by insertion of the synthetic gene for I-SceI (NdeI-BamHI fragment of pSCM525) under T7 promoter control. This vector is used in strain BL21 (DE3) which expresses the T7 RNA polymerase under IPTG induction.

pSCM351, which is an *E. coli* expression vector derived from pUR291 in which the synthetic gene for I-SceI is fused with the Lac Z gene, producing a hybrid protein.

pSCM353, which is an *E. coli* expression vector derived from pEX1 in which the synthetic gene for I-SceI is fused with the Cro/Lac Z gene, producing a hybrid protein.

Examples of yeast expression vectors are: pPEX7, which is a yeast expression vector derived from pRP51-Bam O (a LEU2d derivative of pLG-SD5) by insertion of the synthetic gene under the control of the galactose promoter. Expression is induced by galactose.

pPEX408, which is a yeast expression vector derived from pLG-SD5 by insertion of the synthetic gene under the control of the galactose promoter. Expression is induced by galactose.

Figure 7:
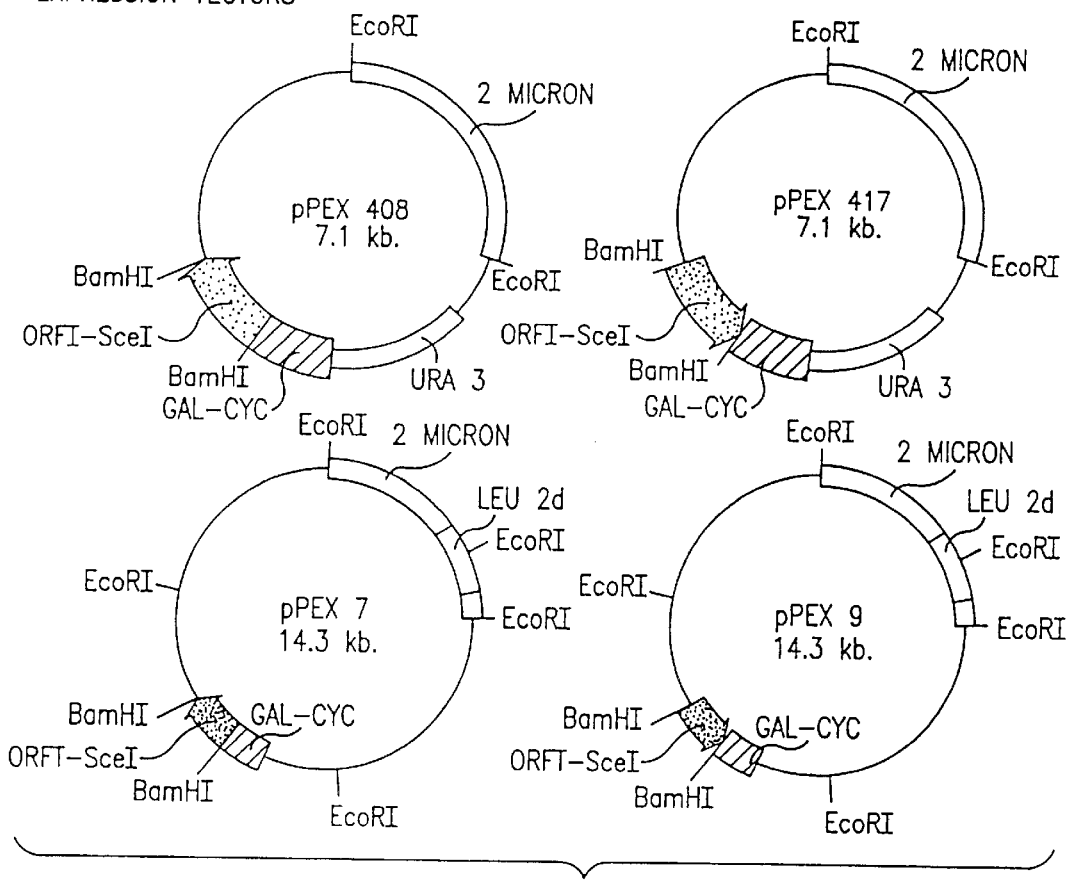
FIG. 7 depicts yeast expression vectors containing the synthetic gene for I-SceI.

Several yeast expression vectors are depicted in FIG. 7.

Figure 8:
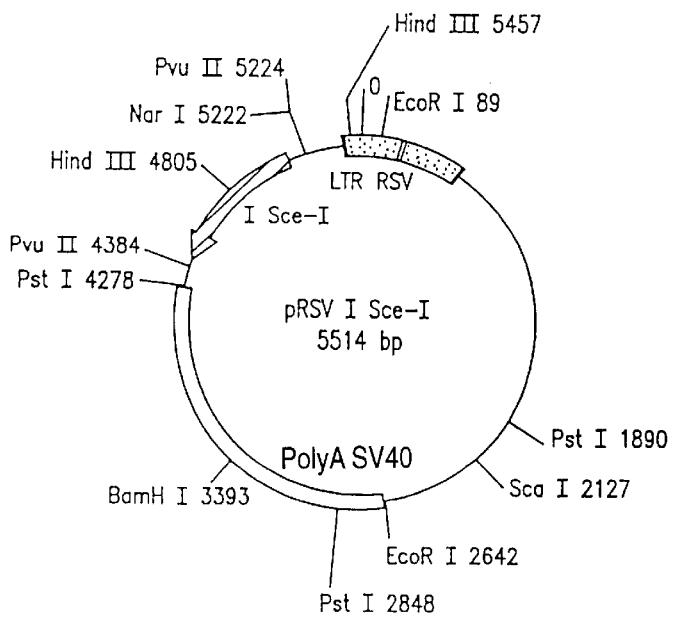
FIG. 8 depicts the mammalian expression vector PRSV I-SceI.

Typical mammalian expression vectors are:

pRSV I-SceI, which is a pRSV derivative in which the synthetic gene (BamHI-PstI fragment from pSCM525) is under the control of the LTR promoter of Rous Sarcoma Virus. This expression vector is depicted in FIG. 8. Vectors for expression in Chinese Hamster Ovary (CHO) cells can also be employed.

5. Cells Transformed with Vectors of the Invention

The vectors of the invention can be inserted into host organisms using conventional techniques. For example, the vectors can be inserted by transformation, transfection, electroporation, microinjection, or by means of liposomes (lipofection).

Cloning can be carried out in prokaryotic or eukaryotic cells. The host for replicating the cloning vehicle will of course be one that is compatible with the vehicle and in which the vehicle can replicate. Cloning is preferable carried out in bacterial or yeast cells, although cells of fungal, animal, and plant origin can also be employed. The preferred host cells for conducting cloning work are bacterial cells, such as *E. coli*. The use of *E. coli* cells is particularly preferred because most cloning vehicles, such as bacterial plasmids and bacteriophages, replicate in these cells.

In a preferred embodiment of this invention, an expression vector containing the DNA sequence encoding the nucleotide sequence of the invention operatively linked to a promoter is inserted into a mammalian cell using conventional techniques.

Application of I-SceI for Large Scale Mapping

1. Occurrence of natural sites in various genomes

Using the purified I-SceI enzyme, the occurrence of natural or degenerate sites has been examined on the complete genomes of several species. No natural site was found in *Saccharomyces cerevisiae, Bacillus anthracis, Borrelia burgdorferi, Leptospira biflexa* and *L. interrogans*. One degenerate site was found on T7 phage DNA.

2. Insertion of artificial sites

Given the absence of natural I-SceI sites, artificial sites can be introduced by transformation or transfection. Two cases need to be distinguished: site-directed integration by homologous recombination and random integration by non-homologous recombination, transposon movement or retroviral infection. The first is easy in the case of yeast and a few bacterial species, more difficult for higher eucaryotes.

3. Insertion vectors

Two types can be distinguished:

I-Site specific cassettes that introduce the I-SceI site together with a selectable marker.

For yeast: all are pAF100 derivatives (Thierry et al. (.1990) YEAST 6:521–534) containing the following marker genes: pAF101: URA3 (inserted in the HindIII site) pAF103: Neo$^R$ (inserted in BglII site) pAF104: HIS3 (inserted in BglII site) pAF105: Kan$^R$ (inserted in BglII site) pAF106: Kan$^R$ (inserted in BglII site) pAF107: LYS2 (inserted between HindIII and EcoR V)

Figure 9:
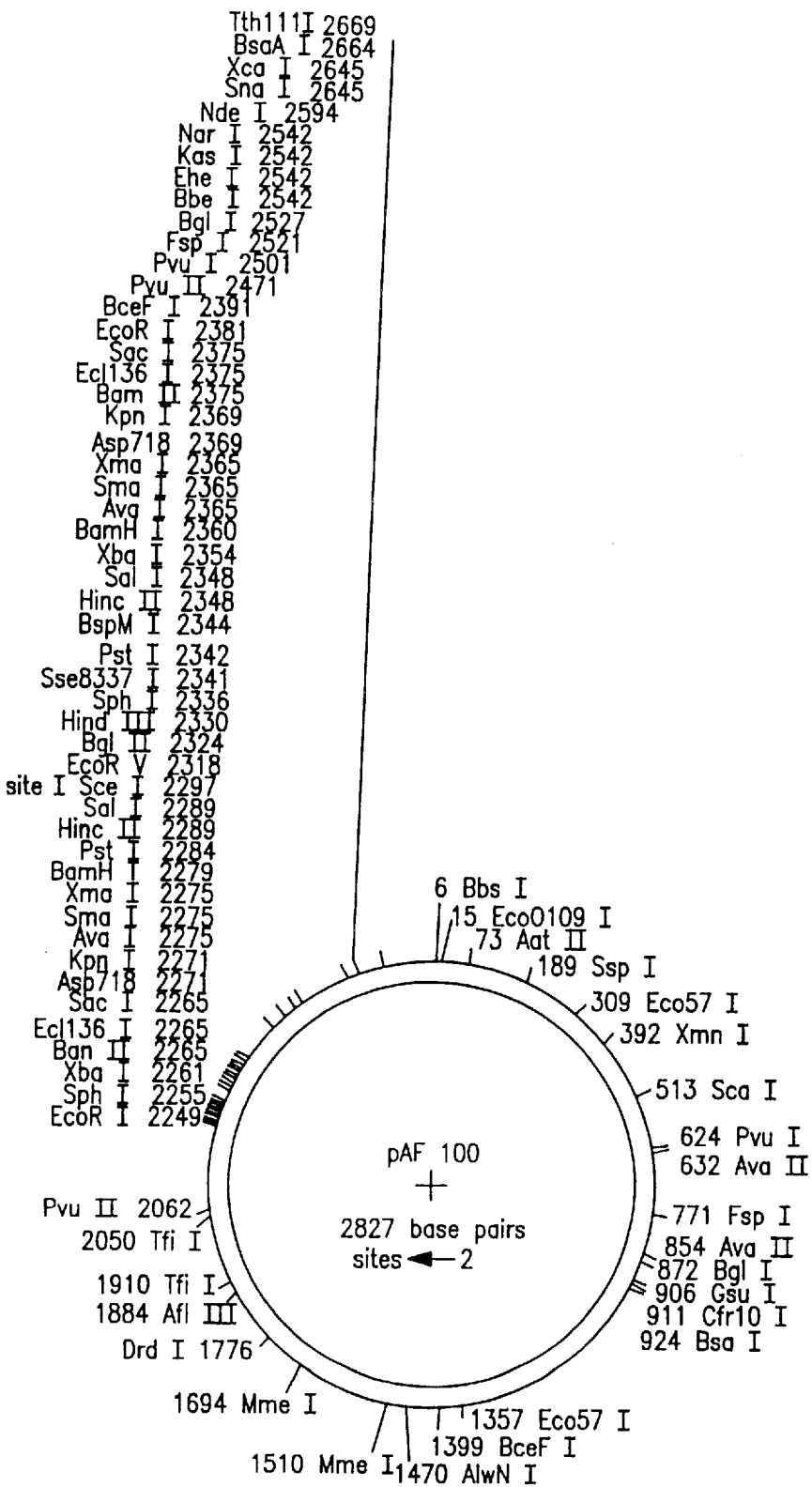
FIG. 9 is a restriction map of the plasmid PAF100. (See also YEAST, 6:521–534, 1990, which is relied upon and incorporated by reference herein).
Figure 10B:
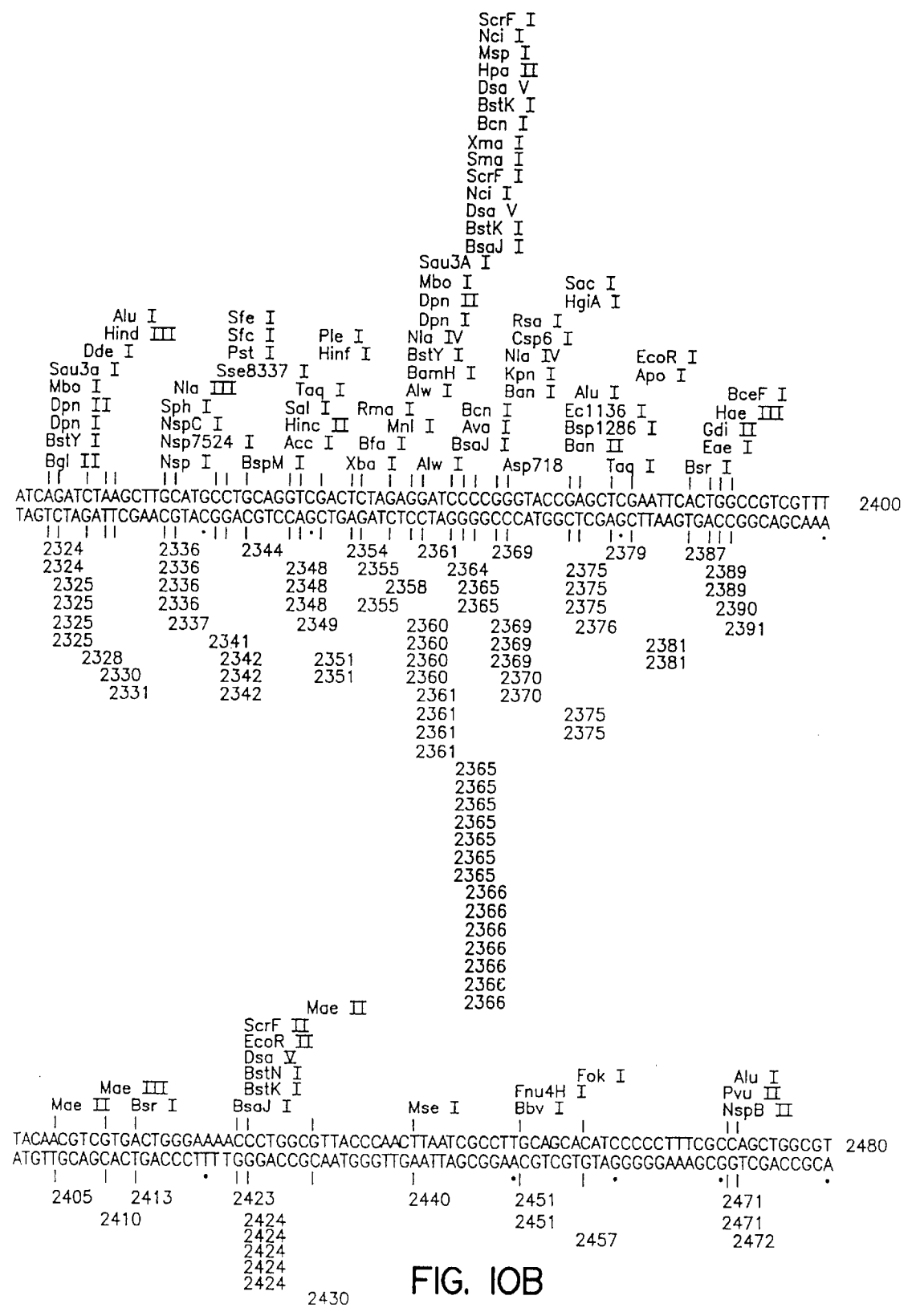

A restriction map of the plasmid pAF100 is shown in FIG. 9. The nucleotide sequence and restriction sites of regions of plasmid pAF100 are shown in FIGS. 10A and 10B. Many transgenic yeast strains with the I-SceI site at various and known places along chromosomes are available.

2- Vectors derived from transposable elements or retroviruses.

Figure 11:
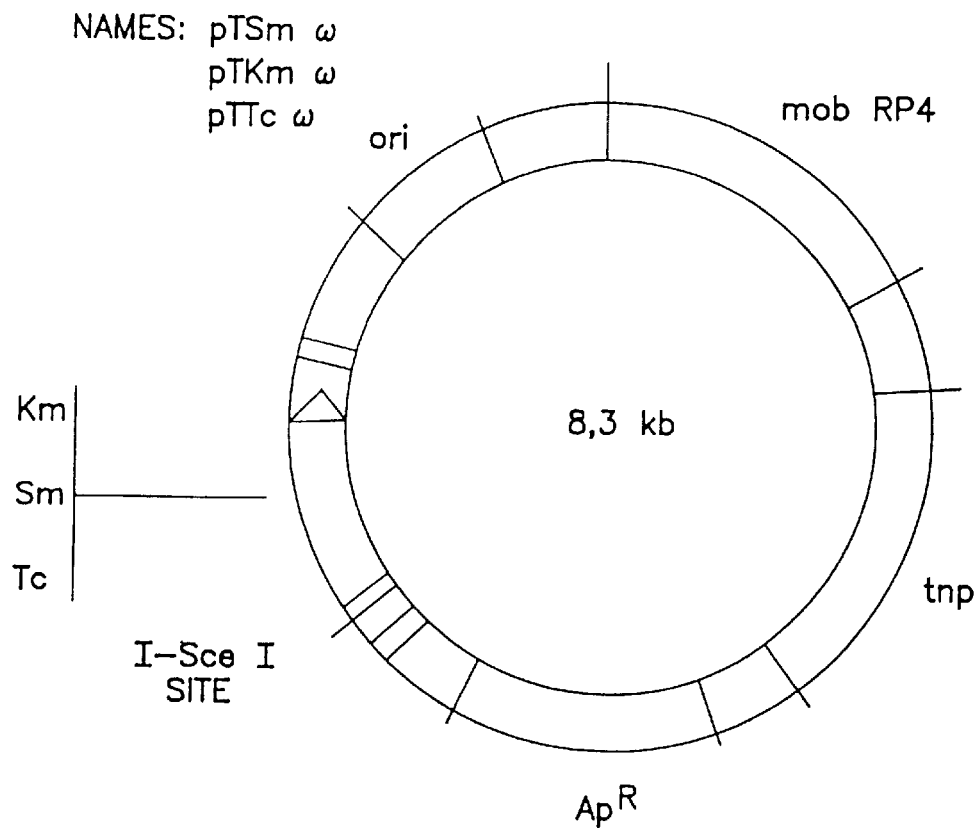
FIG. 11 depicts an insertion vector pTSMω, pTKMω, and pTTcω containing the I-SceI site for E. coli and other bacteria.
Figure 12:
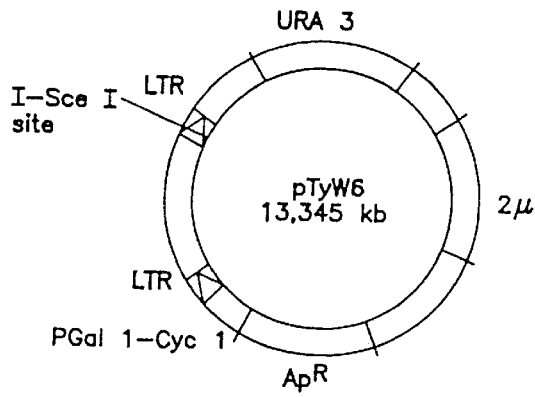
FIG. 12 depicts an insertion vector pTYW6 containing the I-SceI site for yeast.

For E. coli and other bacteria: mini Tn5 derivatives containing the I-SceI site and pTSm ω Str$^R$ pTKm ω Kan$^R$ pTTc ω Tet$^R$ (See FIG. 11)

For yeast: pTyω6 is a pD123 derivative in which the I-SceI site has been inserted in the LTR of the Ty element.

(FIG. 12)

Figure 13A:
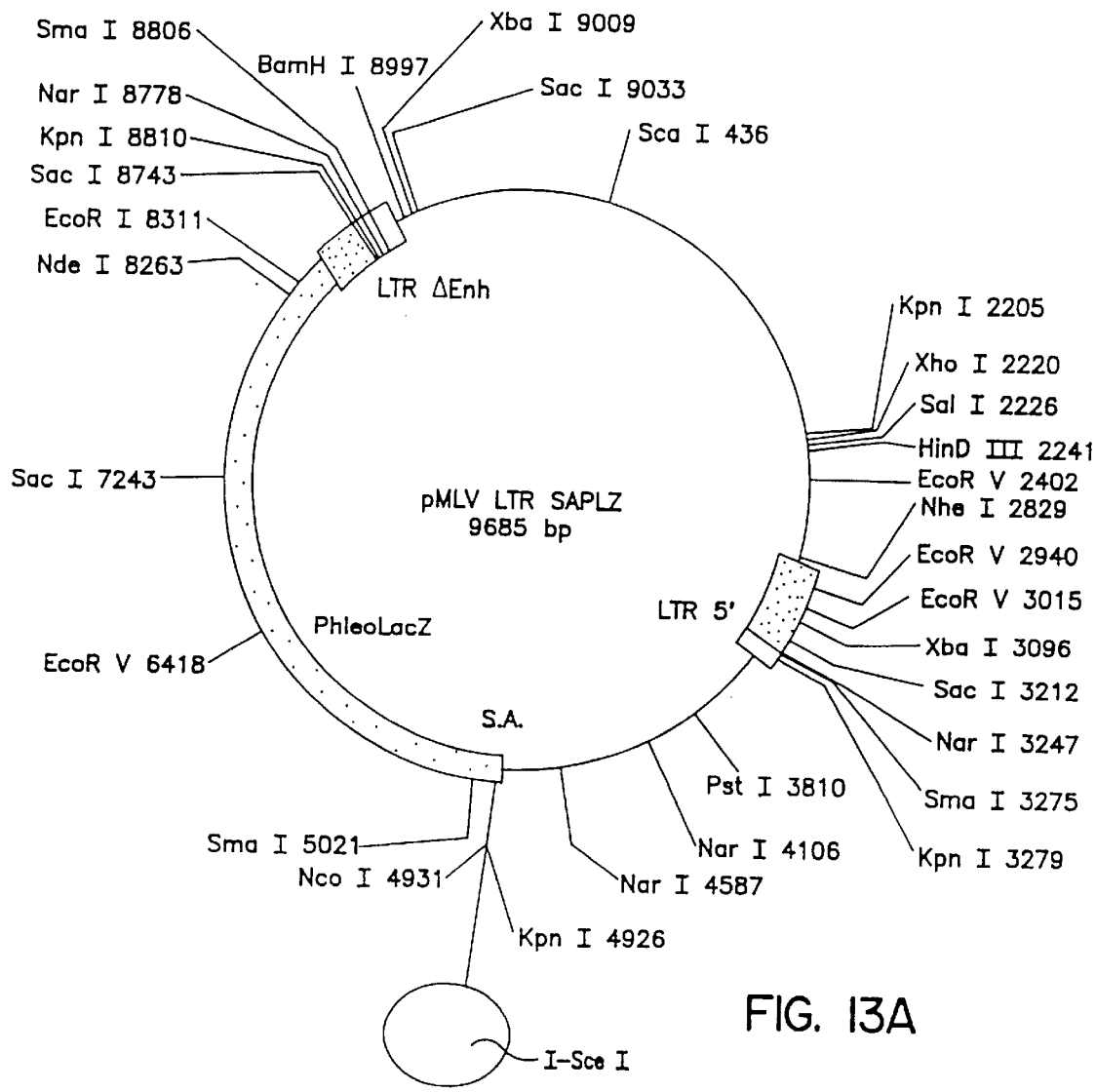
FIG. 13 depicts an insertion vector PMLV LTR SAPLZ containing the I-SceI site for mammalian cells.

For mammalian cells pMLV LTR SAPLZ: containing the I-SceI site in the LTR of MLV and Phleo-LacZ (FIG. 13). This vector is first grown in ψ2 cells (3T3 derivative, from R. Mulligan). Two transgenic cell lines with the I-SceI site at undetermined locations in the genome are available: 1009 (pluripotent nerve cells, J. F. Nicolas) and D3 (ES cells able to generate transgenic animals).

4. The nested chromosomal fragmentation strategy

The nested chromosomal fragmentation strategy for genetically mapping a eukaryotic genome exploits the unique properties of the restriction endonuclease I-SceI, such as an 18 bp long recognition site. The absence of natural I-SceI recognition sites in most eukaryotic genomes is also exploited in this mapping strategy.

First, one or more I-SceI recognition sites are artificially inserted at various positions in a genome, by homologous recombination using specific cassettes containing selectable markers or by random insertion, as discussed supra. The genome of the resulting transgenic strain is then cleaved completely at the artificially inserted I-SceI site(s) upon incubation with the I-SceI restriction enzyme. The cleavage produces nested chromosomal fragments.

The chromosomal fragments are then purified and separated by pulsed field gel (PFG) electrophoresis, allowing one to "map" the position of the inserted site in the chromosome. If total DNA is cleaved with the restriction enzyme, each artificially introduced I-SceI site provides a unique "molecular milestone" in the genome. Thus, a set of transgenic strains, each carrying a single I-SceI site, can be created which defines physical genomic intervals between the milestones. Consequently, an entire genome, a chromosome or any segment of interest can be mapped using artificially introduced I-SceI restriction sites.

The nested chromosomal fragments may be transferred to a solid membrane and hybridized to a labelled probe containing DNA complementary to the DNA of the fragments. Based on the hybridization banding patterns that are observed, the eukaryotic genome may be mapped. The set of transgenic strains with appropriate "milestones" is used as a reference to map any new gene or clone by direct hybridization.

EXAMPLE 1

Figure 14A:
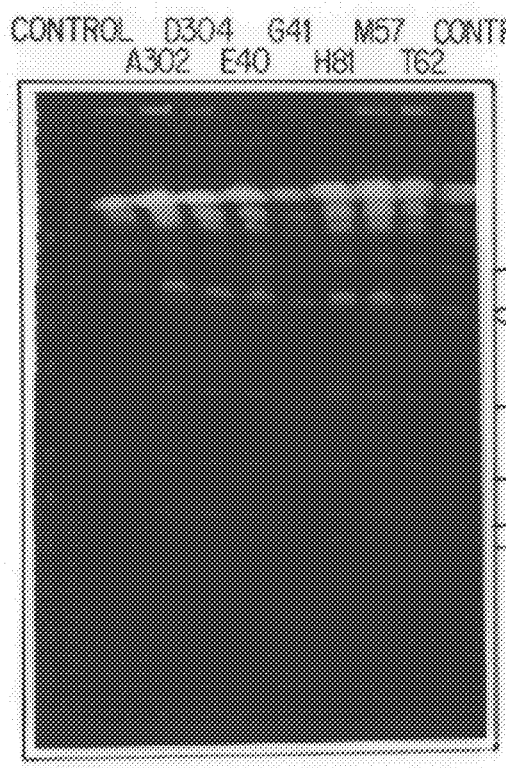
FIG. 14 (Panels A and B) depicts a set of seven transgenic yeast strains cleaved by I-SceI. Chromosomes from FY1679 (control) and from seven transgenic yeast strains with I-SceI sites inserted at various positions along chromosome XI were treated with I-SceI. DNA was electrophoresed on 1% agarose (SeaKem) gel in 0.25×TBE buffer at 130 V and 12° C. on a Rotaphor apparatus (Biometra) for 70 hrs using 100 sec to 40 sec decreasing pulse times. (A) DNA was stained with ethidium bromide (0.2μg/ml) and transferred to a Hybond N (Amersham) membrane for hybridization. (B) $^{32}$P labelled cosmid pUKG040 which hybridizes with the shortest fragment of the set was used as a probe. Positions of chromosome XI and shorter chromosomes are indicated.
Figure 14B:
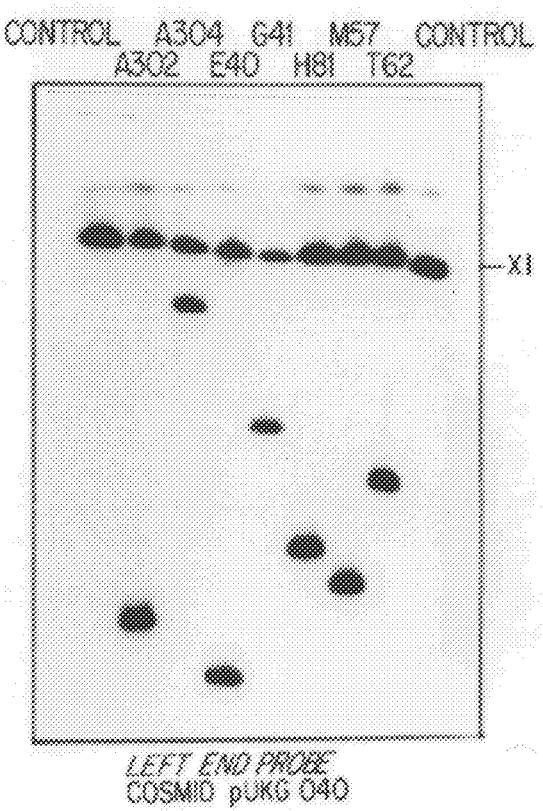
Figure 15A:
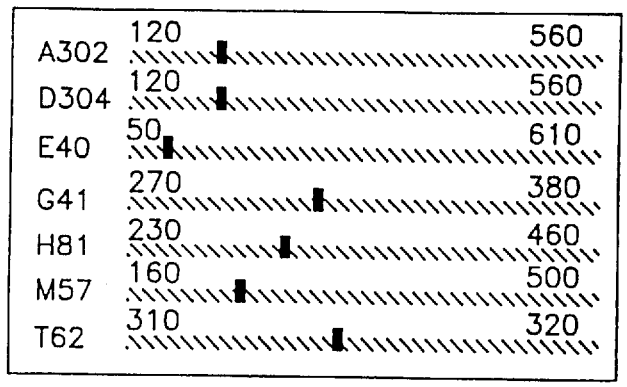
FIG. 15 (Panel A through E) depicts the rationale of the nested chromosomal fragmentation strategy for genetic mapping. (A) Positions of I-SceI sites are placed on the map, irrespective of the left/right orientation (shorter fragments are arbitrarily placed on the left). Fragment sizes as measured from PFGE (FIG. 14A) are indicated in kb (note that the sum of the two fragment sizes varies slightly due to the limit of precision of each measurement). (B) Hybridization with the probe that hybridizes the shortest fragment of the set determines the orientation of each fragment (see FIG. 14B). Fragments that hybridize with the probe (full lines) have been placed arbitrarily to the left. (C) Transgenic yeast strains have been ordered with increasing sizes of hybridizing chromosome fragments. (D) Deduced I-SceI map with minimal and maximal size of intervals indicated in kb (variations in some intervals are due to limitations of PFGE measurements). (E) Chromosome subfragments are used as probes to assign each cosmid clone to a given map interval or across a given I-SceI site.
Figure 15B:
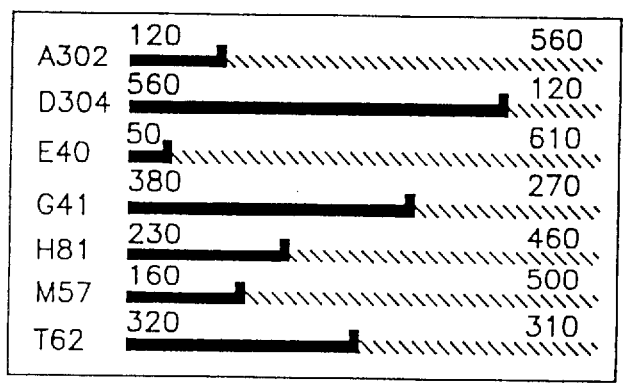
Figure 15C:
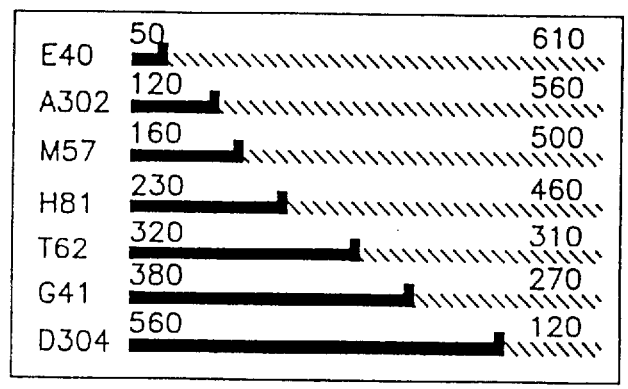
Figures 15D, 15E:
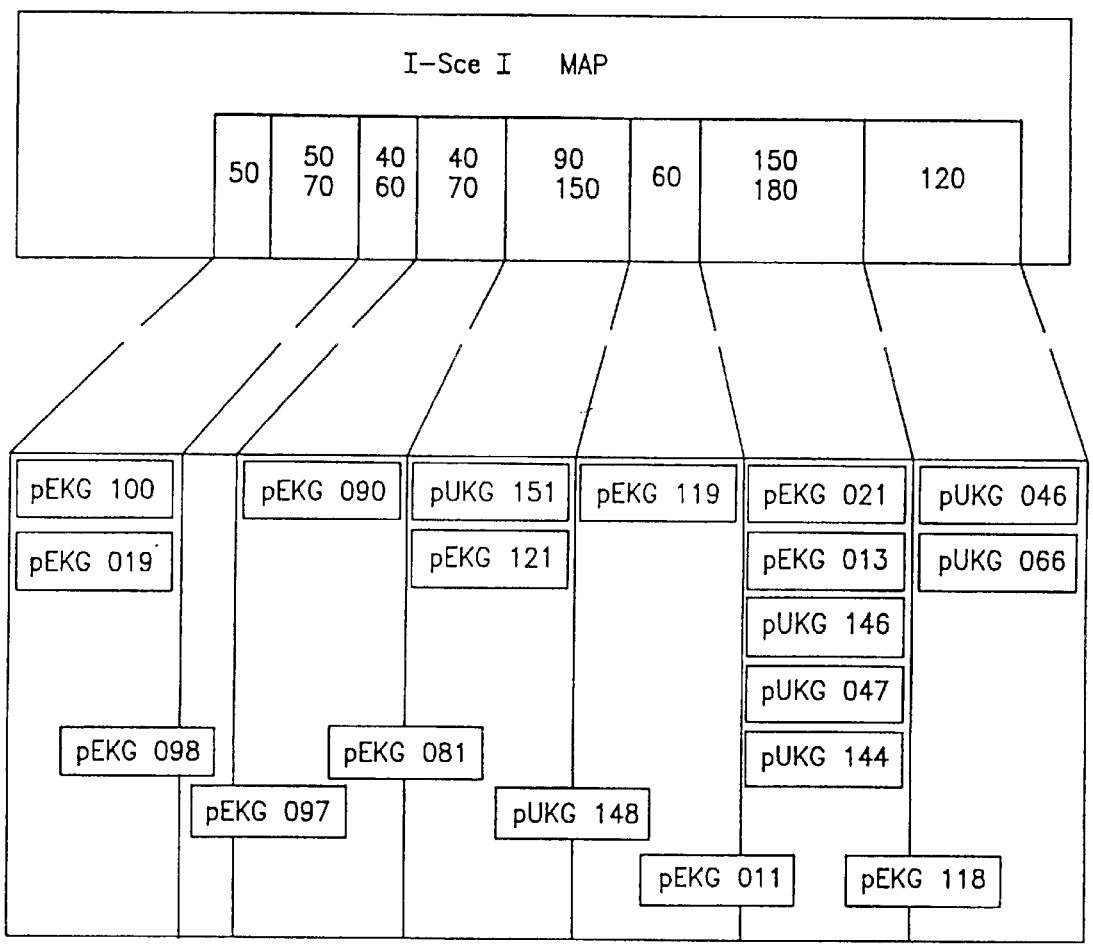

Application of the Nested Chromosomal Fragmentation Strategy to the Mapping of Yeast Chromosome XI This strategy has been applied to the mapping of yeast chromosome XI of *Saccharamyces cerevisiae*. The I-SceI site was inserted at 7 different locations along chromosome XI of the diploid strain FY1679, hence defining eight physical intervals in that chromosome. Sites were inserted from a URA3-1-I-SceI cassette by homologous recombination. Two sites were inserted within genetically defined genes, TIF1 and FAS1, the others were inserted at unknown positions in the chromosome from five non-overlapping cosmids of our library, taken at random. Agarose embedded DNA of each of the seven transgenic strains was then digested with I-SceI and analyzed by pulsed field gel electrophoresis (FIG. 14A). The position of the I-SceI site of each transgenic strain in chromosome XI is first deduced from the fragment sizes without consideration of the left/right orientation of the fragments. Orientation was determined as follows. The most telomere proximal I-SceI site from this set of strains is in the transgenic E40 because the 50 kb fragment is the shortest of all fragments (FIG. 15A). Therefore, the cosmid clone pUKG040, which was used to insert the I-SceI site in the transgenic E40, is now used as a probe against all chromosome fragments (FIG. 14B). As expected, pUKG040 lights up the two fragments from strain E40 (50 kb and 630 kb, respectively). The large fragment is close to the entire chromosome XI and shows a weak hybridization signal due to the fact that the insert of pUKG040, which is 38 kb long, contains less than 4 kb within the large chromosome fragment. Note that the entire chromosome XI remains visible after I-SceI digestion, due to the fact that the transgenic strains are diploids in which the I-SceI site is inserted in only one of the two homologs. Now, the pUKG040 probe hybridizes to only one fragment of all other transgenic strains allowing unambiguous left/right orientation of I-SceI sites (See FIG. 15B). No significant cross hybridization between the cosmid vector and the chromosome subfragment containing the I-SceI site insertion vector is visible. Transgenic strains can now be ordered such that I-SceI sites are located at increasing distances from the hybridizing end of the chromosome (FIG. 15C) and the I-SceI map can be deduced (FIG. 15D). Precision of the mapping depends upon PFGE resolution and optimal calibration. Note that actual left/right orientation of the chromosome with respect to the genetic map is not known at this step. To help visualize our strategy and to obtain more precise measurements of the interval sizes between I-SceI sites between I-SceI, a new pulsed field gel electrophoresis with the same transgenic strains now placed in order was made (FIG. 16). After transfer, the fragments were hybridized successively with cosmids pUKG040 and pUKG066 which light up, respectively, all fragments from the opposite ends of the chromosome (clone pUKG066 defines the right end of the chromosome as defined from the genetic map because it contains the SIR1 gene. A regular stepwise progression of chromosome fragment sizes is observed. Note some cross hybridization between the probe pUKG066 and chromosome III, probably due to some repetitive DNA sequences.

All chromosome fragments, taken together, now define physical intervals as indicated in FIG. 15d. The I-SceI map obtained has an 80 kb average resolution.

EXAMPLE 2

Application of the Nested Chromosomal Fragmentation Strategy to the Mapping of Yeast Artificial Chromosome (YAC) Clones This strategy can be applied to YAC mapping with two possibilities.

1- insertion of the I-SceI site within the gene of interest using homologous recombination in yeast. This permits mapping of that gene in the YAC insert by I-SceI digestion in vitro. This has been done and works.

2- random integration of I-SceI sites along the YAC insert by homologous recombination in yeast using highly repetitive sequences (e.g., B2 in mouse or Alu in human). Transgenic strains are then used as described in ref. P1 to sort libraries or map genes.

The procedure has now been extended to YAC containing 450 kb of Mouse DNA. To this end, a repeated sequence of mouse DNA (called B2) has been inserted in a plasmid containing the I-SceI site and a selectable yeast marker (LYS2). Transformation of the yeast cells containing the recombinant YAC with the plasmid linearized within the B2 sequence resulted in the integration of the I-SceI site at five different locations distributed along the mouse DNA insert. Cleavage at the inserted I-SceI sites using the enzyme has been successful, producing nested fragments that can be purified after electrophoresis. Subsequent steps of the protocol exactly parallels the procedure described in Example 1.

EXAMPLE 3

Application of Nested Chromosomal Fragments to the Direct Sorting of Cosmid Libraries The nested, chromosomal fragments can be purified from preparative PFG and used as probes against clones from a chromosome X1 specific sublibrary. This sublibrary is composed of 138 cosmid clones (corresponding to eight times coverage) which have been previously sorted from our complete yeast genomic libraries by colony hybridization with PFG purified chromosome X1. This collection of unordered clones has been sequentially hybridized with chromosome fragments taken in order of increasing sizes from the left end of the chromosome. Localization of each cosmid clone on the I-SceI map could be unambiguously determined from such hybridizations. To further verify the results and to provide a more precise map, a subset of all cosmid clones, now placed in order, have been digested with EcoRI, electrophoresed and hybridized with the nested series of chromosome fragments in order of increasing sizes from the left end of the chromosome. Results are given in FIG. 17.

Figure 17A:
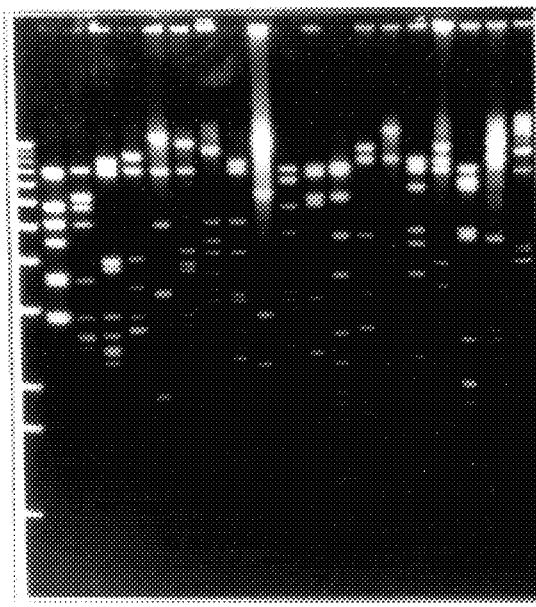
FIG. 17 (Panels A through H) depicts mapping of a cosmid collection using the nested chromosomal fragments as probes. Cosmid DNAs were digested with EcoRI and electrophoresed on 0.9% agarose (SeaKem) gel at 1.5 V/cm for 14 hrs, stained with ethidium bromide and transferred to a Hybond N membrane. Cosmids were placed in order from previous hybridizations to help visualize the strategy. Hybridizations were carried out serially on three identical membranes using left end nested chromosome fragments purified on PFGE (see FIG. 16) as probes. A: ethidium bromide staining (ladder is the BRL "1 kb ladder"), B: membrane #1, probe: Left tel to A302 site, C: membrane #1, probe: Left tel to M57 site, D: membrane #2, probe: Left tel to H81 site, E: membrane #2, probe: Left tel to T62 site, F: membrane #3, probe: Left tel to G41 site, G: membrane #3, probe: Left tel to D304 site, H: membrane #3, probe: entire chromosome XI.
Figure 17B:
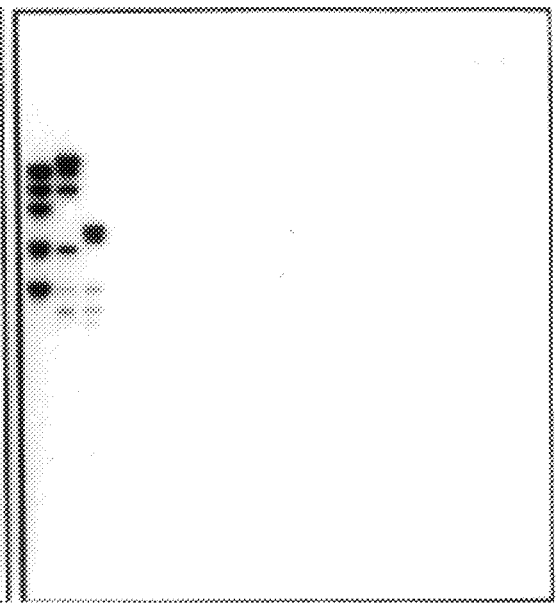
Figures 17C, 17D:
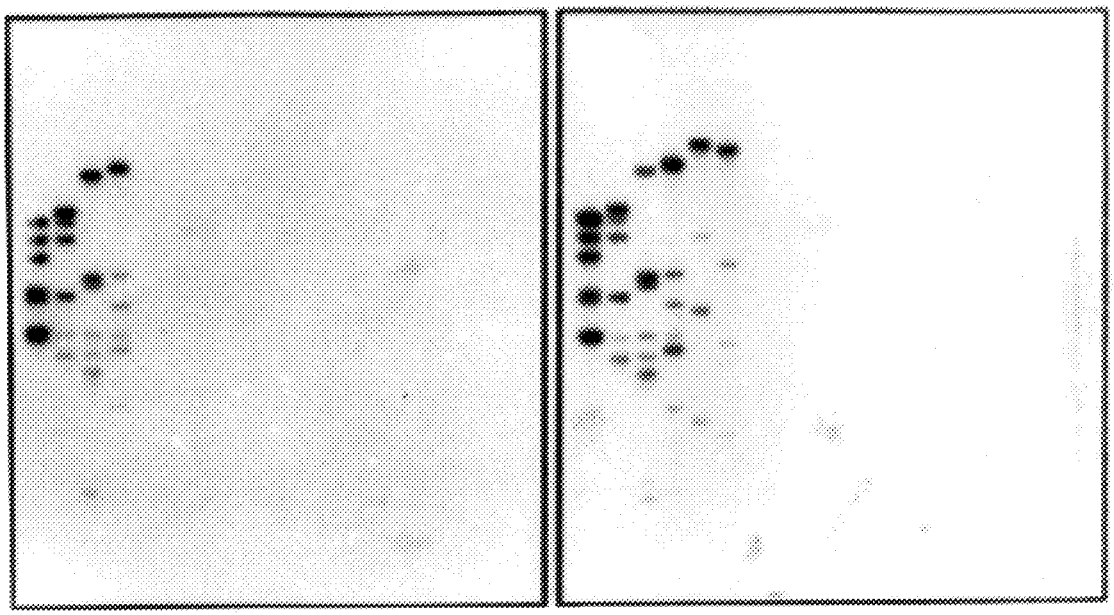
Figures 17E, 17F:
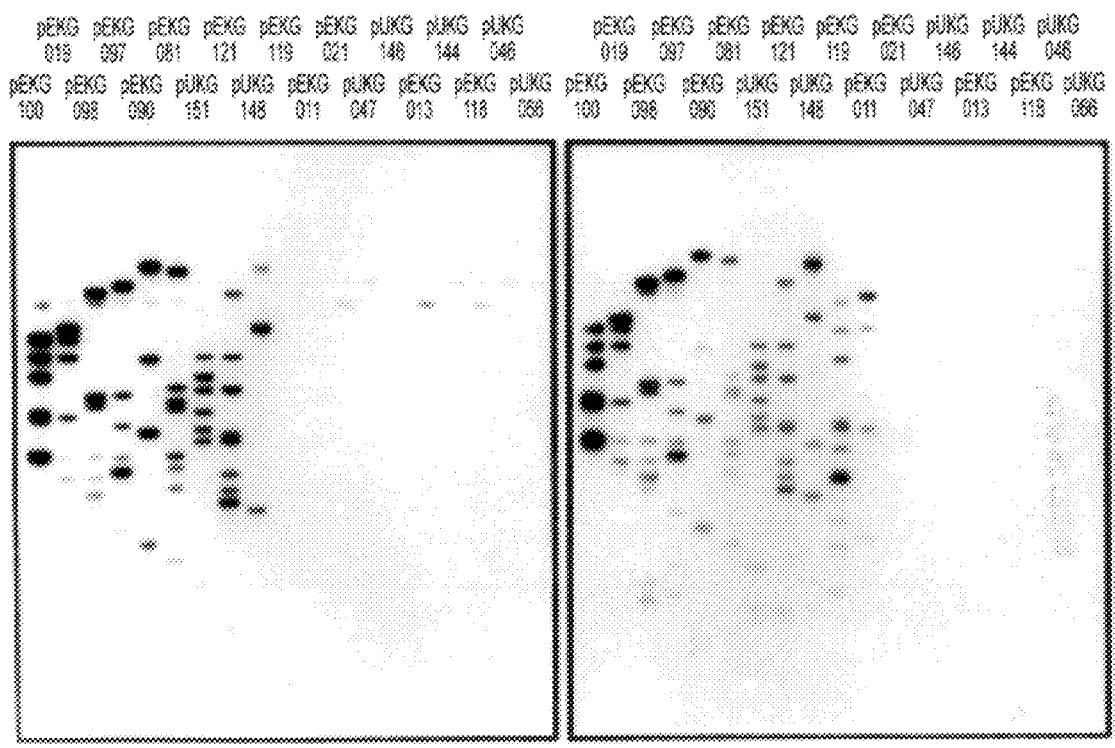
Figures 17G, 17H:
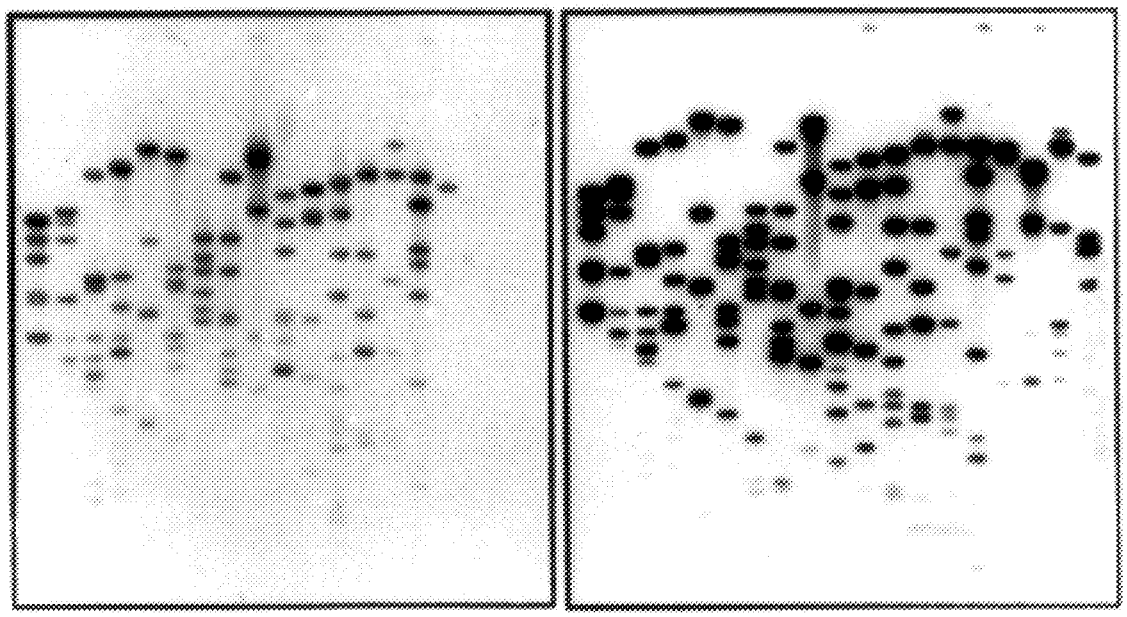

For a given probe, two cases can be distinguished: cosmid clones in which all EcoRI fragments hybridize with the probe and cosmid clones in which only some of the EcoRI fragments hybridize (i.e., compare pEKG100 to pEKG098 in FIG. 17b). The first category corresponds to clones in which the insert is entirely included in one of the two chromosome fragments, the second to clones in which the insert overlaps an I-SceI site. Note that, for clones of the pEKG series, the EcoRI fragment of 8 kb is entirely composed of vector sequences (pWE15) that do not hybridize with the chromosome fragments. In the case where the chromosome fragment possesses the integration vector, a weak cross hybridization with the cosmid is observed (FIG. 17e).

Figure 18:
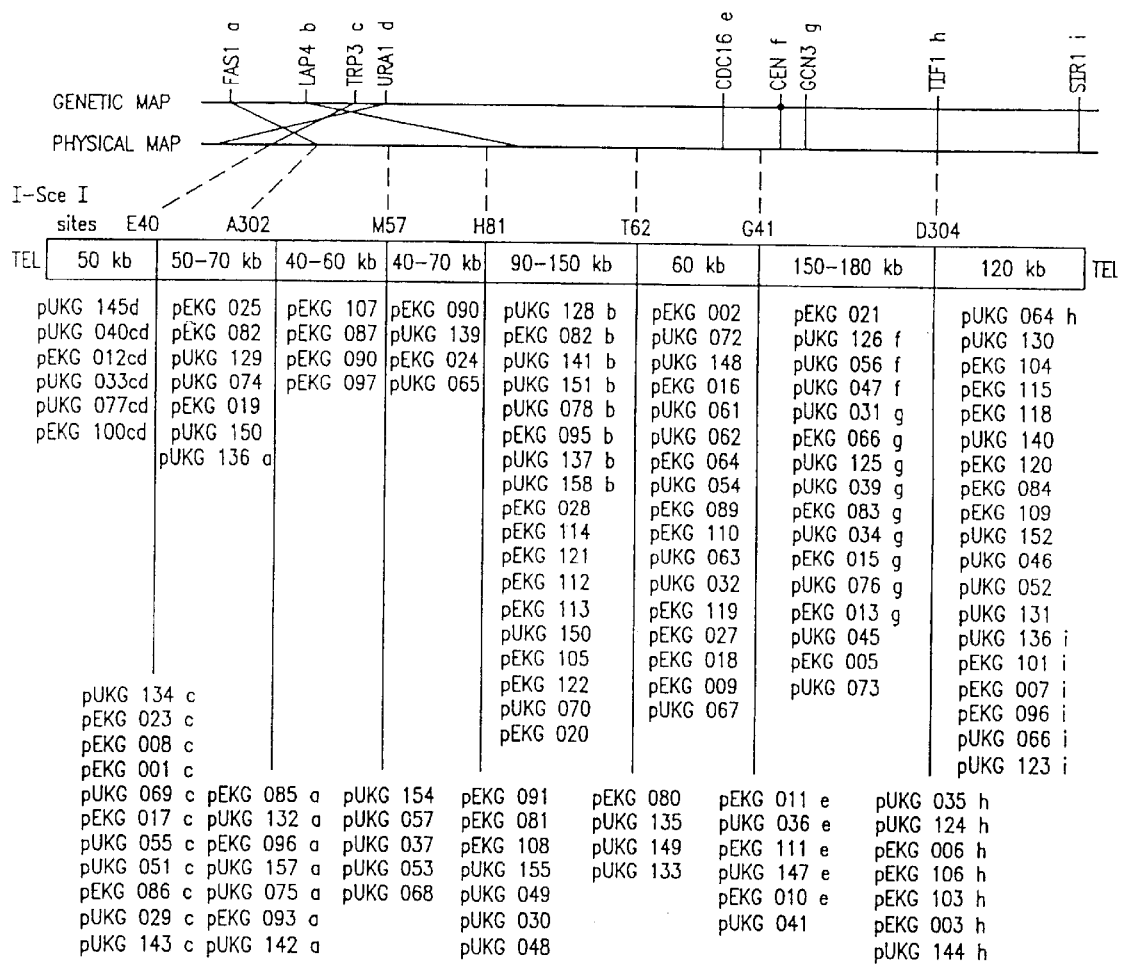
FIG. 18 depicts a map of the yeast chromosome XI as determined from the nested chromosomal fragmentation strategy. The chromosome is divided into eight intervals (with sizes indicated in kb, see FIG. 15D) separated by seven I-SceI sites (E40, A302 . . . ). Cosmid clones falling either within intervals or across a given I-SceI site are listed below intervals or below interval boundaries, respectively. Cosmid clones that hybridize with selected genes used as probes are indicated by letters (a–i). They localize the gene with respect to the I-SceI map and allow comparison with the genetic map (top).

Examination of FIG. 17 shows that the cosmid clones can unambiguously be ordered with respect to the I-SceI map (FIG. 13E), each clone falling either in a defined interval or across an I-SceI site. In addition, clones from the second category allow us to place some EcoRI fragments on the I-SceI maps, while others remain unordered. The complete set of chromosome XI- specific cosmid clones, covering altogether eight times the equivalent of the chromosome, has been sorted with respect to the I-SceI map, as shown in FIG. 18.

5. Partial restriction mapping using I-SceI

In this embodiment, complete digestion of the DNA at the artificially inserted I-SceI site is followed by partial digestion with bacterial restriction endonucleases of choice. The restriction fragments are then separated by electrophoresis and blotted. Indirect end labelling is accomplished using left or right I-Sce half sites. This technique has been successful with yeast chromosomes and should be applicable without difficulty for YAC.

Partial restriction mapping has been done on yeast DNA and on mammalian cell DNA using the commercial enzyme I-SceI. DNA from cells containing an artificially inserted I-SceI site is first cleaved to completion by I-SceI. The DNA is then treated under partial cleavage conditions with bacterial restriction endonucleases of interest (e.g., BamHI) and electrophoresed along with size calibration markers. The DNA is transferred to a membrane and hybridized successively using the short sequences flanking the I-SceI sites on either side (these sequences are known because they are part of the original insertion vector that was used to introduce the I-SceI site). Autoradiography (or other equivalent detection system using non radioactive probes) permit the visualization of ladders, which directly represent the succession of the bacterial restriction endonuclease sites from the I-SceI site. The size of each band of the ladder is used to calculate the physical distance between the successive bacterial restriction endonuclease sites.

Application of I-SceI for In Vivo Site Directed Recombination

1. Expression of I-SceI in yeast

The synthetic I-SceI gene has been placed under the control of a galactose inducible promoter on multicopy plasmids pPEX7 and pPEX408. Expression is correct and induces effects on site as indicated below. A transgenic yeast with the I-SceI synthetic gene inserted in a chromosome under the control of an inducible promoter can be constructed.

2. Effects of site specific double strand breaks in yeast (refs. 18 and P4)

Effects on plasmid-borne I-SceI sites:

Intramolecular effects are described in detail in Ref. 18. Intermolecular (plasmid to chromosome) recombination can be predicted.

Effects on Chromosome Integrated I-SceI Sites

In a haploid cell, a single break within a chromosome at an artificial I-SceI site results in cell division arrest followed by death (only a few % of survival). Presence of an intact sequence homologous to the cut site results in repair and 100% cell survival. In a diploid cell, a single break within a chromosome at an artificial I-SceI site results in repair using the chromosome homolog and 100% cell survival. In both cases, repair of the induced double strand break results in loss of heterozygosity with deletion of the non homologous sequences flanking the cut and insertion of the non homologous sequences from the donor DNA molecule.

3. Application for in vivo recombination YACs in Yeast

Construction of a YAC vector with the I-SceI restriction site next to the cloning site should permit one to induce homologous recombination with another YAC if inserts are partially overlapping. This is useful for the construction of contigs.

4. Prospects for other organisms

Insertion of an I-SceI restriction site has been done for bacteria (*E. coli, Yersinia entorocolitica, Y. pestis, Y. pseudotuberculosis*), and mouse cells. Cleavage at the artificial I-SceI site in vitro has been successful with DNA from the transgenic mouse cells. Expression of I-SceI from the synthetic gene in mammalian or plant cells should be successful.

The I-SceI site has been introduced in mouse cells and bacterial cells as follows:

1- Mouse cells
- a- Mouse cells (ψ2) were transfected with the DNA of the vector pMLV LTR SAPLZ containing the I-SceI site using standard calcium phosphate transfection technique.
- b- Transfected cells were selected in DMEM medium containing phleomycin with 5% fetal calf serum and grown under 12% $CO_2$, 100% humidity at 37° C. until they form colonies.
- c- Phleomycin resistant colonies were subcloned once in the same medium.
- d- Clone MLOP014, which gave a titer of $10^5$ virus particles per ml, was chosen. This clone was deposited at C.N.C.M. on May 5, 1992 under culture collection accession No. I-1207.
- e- The supernatant of this clone was used to infect other mouse cells (1009) by spreading $10^5$ virus particles on $10^5$ cells in DMEM medium with 10% fetal calf serum and 5 mg/ml of polybrene (hexadimethrine bromide). Medium was replaced 6 hours after infection by the same fresh medium.
- f- 24 hours after infection, phleomycin resistant cells were selected in the same medium as above.
- g- phleomycin resistant colonies were subcloned once in the same medium.
- h- one clone was picked and analyzed. DNA was purified with standard procedures and digested with I-SceI under optimal conditions.

2- Bacterial cells

Mini Tn 5 transposons containing the I-SceI recognition site were constructed in *E. coli* by standard recombinant DNA procedures. The mini Tn 5 transposons are carried on a conjugative plasmid. Bacterial conjugation between *E. coli* and Yersinia is used to integrate the mini Tn 5 transposon in Yersinia. Yersinia cells resistant to Kanamycin, Streptomycin or tetracycline are selected (vectors pTKM-ω, pTSM-ω and pTTc-ω, respectively).

Several strategies can be attempted for the site specific insertion of a DNA fragment from a plasmid into a chromosome. This will make it possible to insert transgenes at predetermined sites without laborious screening steps. Strategies are 1- Construction of a transgenic cell in which the I-SceI recognition site is inserted at a unique location in a chromosome. Cotransformation of the transgenic cell with the expression vector and a plasmid containing the gene of interest and a segment homologous to the sequence in which the I-SceI site is inserted.

2- Insertion of the I-SceI recognition site next to or within the gene of interest carried on a plasmid. Cotransformation of a normal cell with the expression vector carrying the synthetic I-SceI gene and the plasmid containing the I-SceI recognition site.

3- Construction of a stable transgenic cell line in which the I-SceI gene has been integrated in the genome under the control of an inducible or constitutive cellular promoter. Transformation of the cell line by a plasmid containing the I-SceI site next to or within the gene of interest.

Figure 19A:
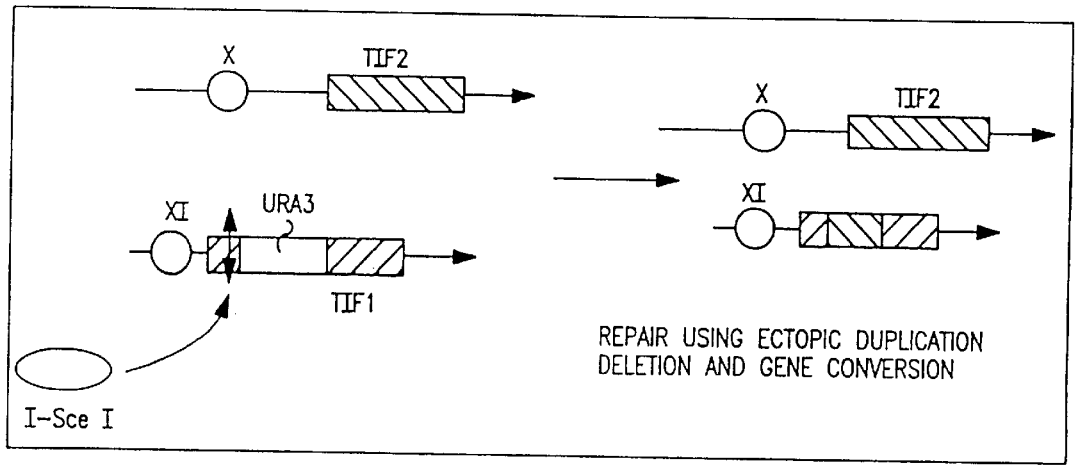
FIG. 19 depicts diagrams of successful site directed homologous recombination experiments performed in yeast.
Figure 19B:
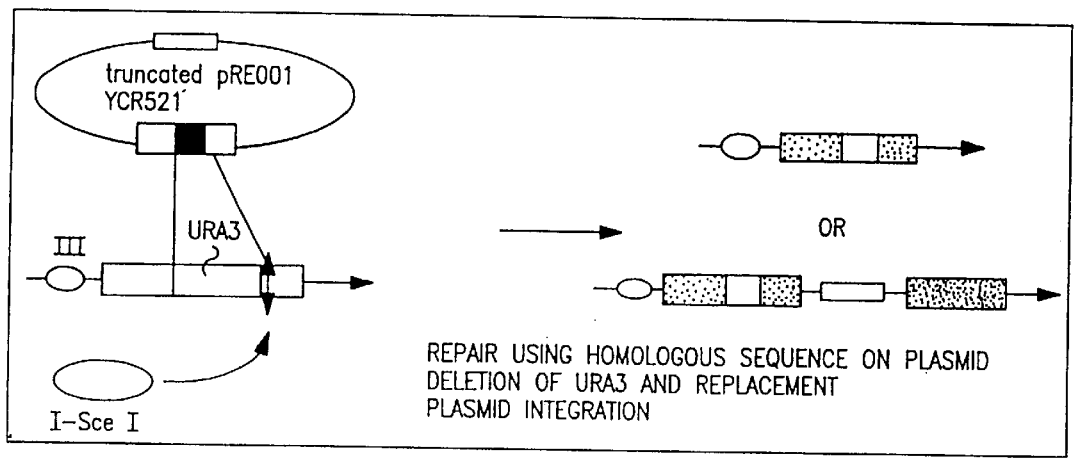

Site directed homologous recombination: diagrams of successful experiments performed in yeast are given in FIG. 19.

Publications Cited In Application

1. B. Dujon, Sequence of the intron and flanking exons of the mitochondrial 21 S rRNA gene of yeast strains having different alleles at the w and RIB 1 loci. Cell (1980) 20, 185–187.
2. F. Michel, A. Jacquier and B. Dujon, Comparison of fungal mitochondrial introns reveals extensive homologies in RNA secondary structure. Biochimie, 1982, 64, 867–881.
3. F. Michel and B. Dujon, Conservation of RNA secondary structures in two intron families including mitochondrial-, chloroplast-, and nuclear-encoded members. The EMBO Journal, 1983, 2, 33–38.
4. A. Jacquier and B. Dujon, The intron of the mitochondrial 21S rRNA gene: distribution in different yeast species and sequence comparison between Kluyveromyces thermotolerans and *Saccharomyces cerevisiae*. Mol. Gen. Gent. (1983) 192, 487–499.
5. B. Dujon and A. Jacquier, Organization of the mitochondrial 21S rRNA gene in *Saccharomyces cerevisiae*: mutants of the peptidyl transferase centre and nature of the omega locus in "Mitochondria 1983", Editors R. J. Schweyen, K. Wolf, F. Kaudewitz, Walter de Gruyter et Co., Berlin, New York (1983), 389–403.
6. A. Jacquier and B. Dujon, An intron encoded protein is active in a gene conversion process that spreads an intron into a mitochondrial gene. Cell (1985) 41, 333–394.
7. B. Dujon, G. Cottarel, L. Colleaux, M. Betermier, A. Jacquier, L. D'Auriol, F. Galibert, Mechanism of integration of an intron within a mitochondrial gene: a double strand break and the transposase function of an intron encoded protein as revealed by in vivo and in vitro assays. "In Achievements and perspectives of Mitochondrial Research". Vol. II, Biogenesis, E. Quagliariello et al. Eds. Elsevier, Amsterdam (1985) pages 215–225.
8. L. Colleaux, L. D'Auriol, M. Betermier, G. Cottarel, A. Jacquier, F. Galibert, and B. Dujon, A universal code equivalent of a yeast mitochondrial intron reading frame is expressed into *Escherichia coli* as a specific double strand endonuclease. Cell (1986) 44, 521–533.
9. B. Dujon, L. Colleaux, A. Jacquier, F. Michel and C. Monteilhet, Mitochondrial introns as mobile genetic elements: the role of intron-encoded proteins. In "Extrachromosomal elements in lower eucaryotes", Reed B et al. Eds. (1986) Plenum Pub. Corp. 5–27.
10. F. Michel and B. Dujon, Genetic Exchanges between Bacteriophage T4 and Filamentous Fungi? Cell (1986) 46, 323.
11. L. Colleaux, L. D'Auriol, F. Galibert and B. Dujon, Recognition and cleavage site of the intron encoded omega transposase. PNAS (1988), 85, 6022–6026.
12. B. Dujon, Group I introns as mobile genetic elements, facts and mechanistic speculations: A Review. Gene (1989), 82, 91–114.

13. B. Dujon, M. Belfort, R. A. Butow, C. Jacq, C. Lemieux, P. S. Perlman, V. M. Vogt, Mobile introns: definition of terms and recommended nomenclature. Gene (1989), 32, 115–118.
14. C. Monteilhet, A. Perrin, A. Thierry, L. Colleaux, B. Dujon, Purification and Characterization of the in vitro activity of I-SceI, a novel and highly specific endonuclease encoded by a group I intron. Nucleic Acid Research (1990), 18, 1407–1413.
15. L. Colleaux, M-R. Michel-Wolwertz, R. F. Matagne, B. Dujon—The apocytochrome b gene of *Chlamydomonas smithii* contains a mobile intron related to both Saccharomyces and Neurospora introns. Mol. Gen. Genet. (1990) 223, 288–296.
16. B. Dujon Des introns autonomes et mobiles. Annales de l'Institut Pasteur/Actualites (1990) 1. 181–194.
17. A. Thierry, A. Perrin, J. Boyer, C. Fairhead, B. Dujon, B. Frey, G. Schmitz. Cleavage of yeast and bacteriophage 17 genomes at a single site using the rare cutter endonuclease I-Sce. I Nuc. Ac. Res. (1991) 19, 189–190.
18. A. Plessis, A. Perrin, J. E. Haber, B. Dujon, Site specific recombination determined by I-SceI, a mitochondrial intron-encoded endonuclease expressed in the yeast nucleus. GENETICS (1992) 130, 451–460.

Abstracts

A1. A. Jacquier, B. Dujon. Intron recombinational insertion at the DNA level: Nature of a specific receptor site and direct role of an intron encoded protein. Cold Spring Harbor Symposium 1984.
A2. I. Colleaux, L. D'Auriol, M. Demariaux, 3. Dujon, F. Galibert, and A. Jacquier, Construction of a universal code equivalent from a mitochondrial intron encoded transposase gene using oligonucleotide directed multiple mutagenesis. Colloque International de DNRS "oligonucleotids et Genetique Moleculaire" Aussois (Savoie) 8–12 Jan. 1985.
A3. L. Colleaux, D'Auriol, M. Demariaux, B. Dujon, F. Galibert, and A. Jacquier, Expression in *E. coli* of a universal code equivalent of a yeast mitochondrial intron reading frame involved in the integration of an intron within a gene. Cold Spring Harbor Meeting on "Molecular Biology of Yeast", Aug. 13–19, 1985.
A4. B. Dujon, G. Cottarel, L. Colleaux, M. Demariaux, A. Jacquier, L. D'Auriol, and F. Galibert, Mechanism of integration of an intron within a mitochondrial gene: a double strand break and the "transposase" function of an intron encoded protein as revealed by in vivo and in vitro assays. International symposium on "Achievements and Perspectives in Mitochondrial Research", Selva de Fasono (Brindisi, Italy) 26 Sep. 1985.
A5. L. Colleaux, G. Cottarel, M. Betermier, A. Jacquier, B. Dujon, L. D'auriol, and F. Galibert, Mise en evidence de l'activite endonuclease double brin d'unc protein codee par un intron mitochondrial de levure. Forum sur la Biologie Moleculaire de la levure, Bonbannes, France 2–4 Oct. 1985.
A6. B. Dujon, L. Colleaux, F. Michel and A. Jacquier, Mitochondrial introns as mobile genetic elements. In "Extrachromosomal elements in lower eucaryotes", Urbana, Ill., 1–5 Jun. 1986.
A7. L. Colleaux and B. Dujon, Activity of a mitochondrial intron encoded transposase. Yeast Genetics and Molecular Biology Meeting, Urbana, Ill. 3–6 Jun. 1986.
A8. L. Colleaux and B. Dujon, The role of a mitochondrial intron encoded protein. XIIIth International Conference on Yeast Genetics and Molecular Biology, Banff, Alberta (Canada) 31 Aug. –5 Sep. 1986.
A9. L. Colleaux, L. D'Aurio, F. Galibert and and B. Dujon, Recognition and cleavage specificity of an intron encoded transposase. 1987 Meeting on Yeast Genetics and Molecular Biology. San Francisco, Calif. 16–21 Jun. 1937.
A10. A. Perrin, C. Monteilhet, L. Colleaux and B. Dujon, Biochemical activity of an intron encoded transposase *Saccharomyces cerevisiae*. Cold Spring Harbor Meeting on "Molecular Biology of Mitochondria and chloroplasts"25–30 Aug. 1987 Cold Spring Harbor, N.Y.
A11. B. Dujon, A. Jacquier, L. Colleaux, C. Monteilhet, A. Perrin, "Les Introns autoepissables et leurs proteins" Colloque "Biologie Moleculaire de la levure": expression genetique chez Saccharomyces "organise par la Societe francaise de Microbiologie" 18 Jan. 1988 Institut Pasteur, Paris.
A12. L. Colleaux, L. D'Auriol, C. Monteilhet, F. Galibert and B. Dujon, Characterization of the biochemical activity of an intron encoded transposase. 14th International Conference on Yeast Genetics and Molecular Biology. Espoo, Finland, 7–13 Aug. 1988.
A13. B. Dujon, A group I intron as a mobile genetic element, Albany Conference sur "RNA: catalysis, splicing, evolution", Albany, N.Y., 22–25 Sep. 1988.
A14. B. Dujon, L. Colleaux, C. Monteilhet, A. Perrin, L. D'Auriol, F. Galibert, Group I introns as mobile genetic elements: the role of intron encoded proteins and the nature of the target site. 14th Annual EMBO Symposium "Organelle genomes and the nucleus" Heidelberg, 26–29 Sep. 1988.
A15. L. Colleaux, R. Matagne, B. Dujon, A new mobile mitochondrial intron provides evidence for genetic exchange between Neurospora and Chlamydomonas species. Cold Spring Harbor, May 1989.
A16. L. Colleaux, M. R. Michel-Wolwertz, R. F. Matagne, B. Dujon, The apoxytochrome b gene of *Chlamydomonas smithii* contains a mobile intron related to both Saccharomyces and Neurospora introns. Fourth International Conference on Cell and Molecular Biology of Chlamydomonas. Madison, Wis., April 1990.
A17. B. Dujon, L. Colleaux, E. Luzi, C. Monteilhet, A. Perrin, A. Plessis, I. Stroke, A. Thierry, Mobile Introns, EMBO Workshop on "Molecular Mechanisms of transposition and its control", Roscoff (France) Jun. 1990.
A18. A. Perrin, C. Monteilhet, A. Thierry, E. Luzi, I. Stroke, L. Colleaux, B. Dujon. I-SceI, a novel double strand site specific endonuclease, encoded by a mobile group I intron in Yeast. Workshop on "RecA and Related Proteins" Sacly, France 17–21 Sep. 1990.
A19. A. Plessis, A. Perrin, B. Dujon, Site specific recombination induced by double strand endonucleases, HO and I-SceI in yeast. Workshop on "RecA and Related Proteins" Saclay, France 17–21 Sep. 1990.
A20. B. Dujon, The genetic propagation of introns 20th FEBS Meeting, Budapest, Hungary, August 1990.
A21. E. Luzi, B. Dujon, Analysis of the intron encoded site specific endonuclease I-SceI by mutagenesis, Third European Congress on Cell Biology, Florence, Italy, Sep. 1990.
A22. B. Dujon, Self splicing introns as contagious genetic elements. Journees Franco-Beiges de Pont a Mousson. October 1990.
A23. B. Frey, H. Dubler, G. Schmitz, A. Thierry, A. Perrin, J. Boyer, C. Fairhead, B. Dujon, Specific cleavage of the yeast genome at a single site using the rare cutter endonuclease I-SceI Human Genome, Frankfurt, Germany, November 1990.

A24. B. Dujon, A. Perrin, I. Stroke, E. Luzi, L. Colleaux, A. Plessis, A. Thierry, The genetic mobility of group I introns at the DNA level. Keystone Symposia Meeting on "Molecular Evolution of Introns and Other RNA elements", Taos, New Mexico, 2–8 Feb. 1991.

A25. B. Dujon, J. Boyer, C. Fairhead, A. Perrin, A Thierry, Cartographie chez la levure. Reunion "Strategies d'etablissement des cartes geniques" Toulouse 30–31 May 1991.

A26. B. Dujon, A. Thierry, Nested chromosomal fragmentation using the meganuclease I-SceI: a new method for the rapid mapping of the yeast genome. Elounda, Crete 15–17 May 1991.

A27. A. Thierry, L. Gaillon, F. Galibert, B. Dujon. The chromosome XI library: what has been accomplished, what is left. Brugge meeting 22–24 Sep. 1991.

A28. B. Dujon, A. Thierry, Nested chromosomal fragmentation using the meganuclease I-SceI: a new method for the rapid physical mapping of the eukaryotic genomes. Cold Spring Harbor 6–10 May 1992.

A29. A. Thierry, L. Gaillon, F. Galibert, B. Dujon. Yeast chromosome XI: construction of a cosmid contig. a high resolution map and sequencing progress. Cold Spring Harbor 6–10 May 1992.

In Preparation

P1. A. Thierry and B. Dujon, Nested Chromosomal Fragmentation Using the Meganuclease I-SceI: Application to the physical mapping of a yeast chromosome and the direct sorting of cosmid libraries. Probably Submission to GENOMICS or EMBO J.

P2. A. Thierry, L. Colleaux and B. Dujon: Construction and Expression of a synthetic gene coding for the meganuclease I-SceI. Possible submission: NAR, EMBO J.

P3. I. Stroke, V. Pelicic and B. Dujon: The evolutionarily conserved dodecapeptide motifs of intron-encoded I-SceI are essential for endonuclease function. Submission to EMBO J.

P4. C. Fairhead and B. Dujon: Consequences of unique double-stranded breaks in yeast chromosomes: death or homozygous. Mol. Gen. Genet. 240:170–180 (1993).

P5. A. Perrin, M. Buckle and B. Dujon: Asymmetrical recognition and activity of the I-SceI endonuclease on its site and on intron-exon junctions. The EMBO Journal, 12(7):2939–2847(1993).

The entire disclosure of all publications and abstracts cited herein is incorporated by reference herein.

Induction of homologous recombination in mammalian chromosomes using the I-SceI system of *Saccharomyces cerevisiae*

EXAMPLE 4

Introduction

Homologous recombination (HR) between chromosomal and exogenous DNA is at the basis of methods for introducing generic changes into the genome (5B, 20B). Parameters of the recombination mechanism have been determined by studying plasmid sequences introduced into cells (1B, 4B, 10B, 12B) and in in Vitro system (8B). HR is inefficient in mammalian cells but is promoted by double-strand breaks in DNA.

So far, it has not been possible to cleave a specific chromosomal target efficiently, thus limiting our understanding or recombination and its exploitation. Among endonucleases, the *Saccharomyces cerevisiae* mitochondrial endonuclease I-SceI (6B) has characteristics which can be exploited as a tool for cleaving a specific chromosomal target and, therefore, manipulating the chromosome in living organisms. I-Sce I protein is an endonuclease responsible for intron homing in mitochondria of yeast, a non-reciprocal mechanism by which a predetermined sequence becomes inserted at a predetermined site. It has been established that endonuclease I-Sce I can catalyze recombination in the nucleus of yeast by initiating a double-strand break (17B). The recognition site of endonuclease I-Sce I is 18 bp long, therefore, the I-Sce I protein is a very rare cutting restriction endonuclease in genomes (22B). In addition, as the I-Sce I protein is not a recombinase, its potential for chromosome engineering is larger than that of systems with target sites requirement on both host and donor molecules (9B).

We demonstrate here that the yeast I-SceI endonuclease can efficiently induce double-strand breaks in chromosomal target in mammalian cells and that the breaks can be repaired using a donor molecule that shares homology with the regions flanking the break. The enzyme catalyzes recombination at a high efficiency. This demonstrates that recombination between chromosomal DNA and exogenous DNA can occur in mammalian cells by the double-strand break repair pathway (21B).

MATERIALS AND METHODS

Plasmid construction pG-MPL was obtained in four steps: (I) insertion of the 0.3 kb Bgl II-Sma I fragment (treated with Klenow enzyme) of the Moloney Murine Leukemia Virus (MoMuLV) env gene (25B) containing SA between the Nhe I and Xba I sites (treated with Klenow enzyme), in the U3 sequence of the 3'LTR of MoMuLV, in an intermediate plasmid. (II) insertion in this modified LTR with linkers adaptors of the 3.5 kb Nco I-Xho I fragment containing the PhleoLacZ fusion gene (15B) (from pUT65 from Cayla laboratory) at the Xba I site next to SA. (III) insertion of this 3'LTR (containing SA and PhleoLacZ), recovered by Sal I-EcoR I double digestion in p5'LTR plasmid (a plasmid containing the 5'LTR to the nucleotide number 563 of MoMuLV (26B) between the Xho I and the EcoR I sites, and (VI) insertion of a synthetic I-Sce I recognition site into the Nco I site in the 3'LTR (between SA and PhleoLacZ).

pG-MtkP1 was obtained by the insertion (antisense to the retroviral genome) of the 1.6 kb tk gene with its promoter with linker adaptators at the Pst I site of pG-MPL. pVRneo was obtained in two steps (I) insertion into pSP65 (from Promega) linearized by Pst I-EcoR I double digestion of the 4.5 kb Pst I to EcoR I fragment of pG-MPL containing the 3'LTR with the SA and PhleoLacZ, (II) insertion of the 2.0 kb Bgl II-BamH I fragment (treated with Klenow enzyme) containing neoPolyA from pRSVneo into the Nco I restriction site (treated with Klenow enzyme) of pSP65 containing part of the 3'LTR of G-MPL (between SA and PhleoLacZ).

pCMV(I-Sce I+) was obtained in two steps: (I) insertion of the 0.73 kb BamH I-Sal I, I-Sce I containing fragment (from pSCM525, A. Thierry, personal gift) into the phCMV1 (F. Meyer, personal gift) plasmid cleaved at the BamH I and the Sal I sites, (II) insertion of a 1.6 kb (nucleotide number 3204 to 1988 in SV40) fragment containing the polyadenylation signal of SV40 into the Pst I site of phCMV1.

pCMV(I-Sce I–) contains the I-Sce I ORF in reverse orientation in the pCMV(I-Sce I+) plasmid. It has been obtained by inserting the BamH I-Pst I I-Sce I ORF fragment (treated with Klenow enzyme) into the phCMV PolyA vector linearized by Nsi I and Sal I double-digestion and treated with Klenow enzyme.

Plasmids pG-MPL, pG-MtkP1 , pG-MtkΔPAPL have been described. In addition to the plasmids described above, any kind of plasmid vector can be constructed containing various promoters, genes, polyA site, I-Sce I site.

Cell culture and selection

3T3, PCC7 S, ψ 2 are referenced in (7B) and (13B). Cell selection medium: gancyclovir (14B, 23B) was added into the tissue culture medium at the concentration of 2 μM. Gancyclovir selection was maintained on cells during 6 days. G418 was added into the appropriate medium at a concentration of 1 mg/ml for PCC7-S and 400 μg/ml for 3T3. The selection was maintained during all the cell culture. Phleomycin was used at a concentration of 10 μg/ml.

Cell lines

ψ cell line was transfected with plasmids containing a proviral recombinant vector that contain I-SceI recognition site: pG-MPL, pG-MtkPL, pG-Mtk$_{APA}$PL NIH 3T3 Fibroblastic cell line is infected with:

G-MPL. Multiple (more than 30) clones were recovered. The presence of 1 to 14 proviral integrations and the multiplicity of the different points of integration were verified by molecular analysis.

G-MtkPL. 4 clones were recovered (3 of them have one normal proviral integration and 1 of them have a recombination between the two LTR so present only one I-Sce I recognition site).

Embryonal carcinoma PCC7-S cell line is infected with

G-MPL. 14 clones were recovered, normal proviral integration.

Embryonic stem cell line D3 is infected with

G-MPL. 4 clones were recovered (3 have normal proviral integration, 1 has 4 proviral integrations).

"Prepared" Mouse Cells

Insertion of the retrovirus (proviral integration) induces duplication of LTR containing the I-Sce I site. The cell is heterozygotic for the site.

Transfection, Infection, Cell Staining and Nucleic Acids Blot Analysis

These procedures were performed as described in (2B, 3B).

Results

To detect I-Sce I HR we have designed the experimental system shown in FIG. 20. Defective recombinant retroviruses (24B) were constructed with the I-SceI recognition site and a PhleoLacZ (15B) fusion gene inserted in their 3'LTR (FIG. 20a). Retroviral integration results in two I-Sce I sites distant of 5.8 kb or 7.2 kb from each other into the cell genome (FIG. 20b). We hypothesized that I-Sce I-induced double-strand breaks (DSB) at these sites (FIG. 20c) could initiate HR with a donor plasmid (pVRneo, FIG. 20d) containing sequences homologous to the flanking regions of the DSBs and that non-homologous sequences, carried by the donor plasmid, could be copied during this recombination (FIG. 20e).

Introduction of duplicated I-Sce I recognition sites into the genome of mammalian cells by retrovirus integration More specifically, two proviral sequences were used in these studies. The G-MtkPL proviral sequences (from G-MtkPL virus) 1 contain the PhleoLacZ fusion gene for positive selection of transduced cells (in phleomycine-containing medium) and the tk gene for negative selection (in gancyclovir-containing medium) The G-MPL proviral sequences (from G-MPL virus) contain only the PhleoLacZ sequences. G-MtkPL and G-MPL are defective recombinant retroviruses (16B) constructed from an enhancerless Moloney murine leukemia provirus. The virus vector functions as a promoter trap and therefore is activated by flanking cellular promoters.

Figure 21A:
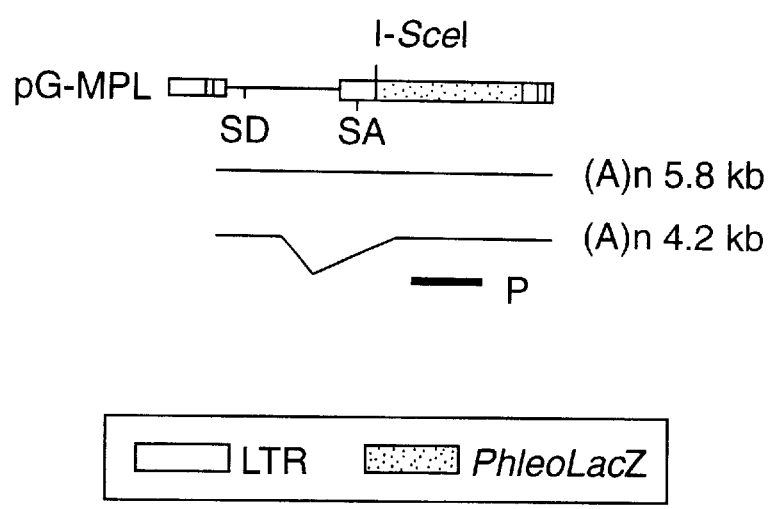
FIGS. 21A and B. A. Scheme of pG-MPL. SD and SA are splice donor and splice acceptor sites. The structure of the unspliced 5.8 kb (genomic) and spliced 4;2 kb transcripts is shown below. Heavy bar is $^{32}$P radiolabelled LacZ probe (P). B. RNA Northern blot analysis of a pG MLP transformed ψ-2 producer clone using polyadenylated RNA. Note that the genomic and the spliced mRNA are produced at the same high level.
Figure 21B:
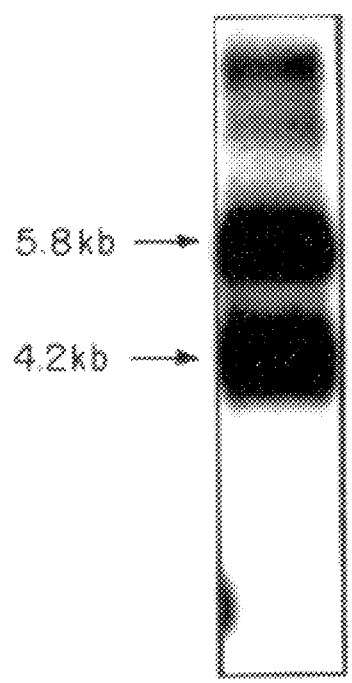

Virus-producing cell lines were generated by transfecting pG-MtkPL or G-MPL into the ψ-2 package cell line (13B). Northern blot analysis of viral transcripts shows (FIG. 21) that the ψ-2-G-MPL line expresses 4.2 and 5.8 kb transcripts that hybridized with LacZ probes. These transcripts probably initiate in the 5'LTR and terminate in the 3'LTR. The 4.5 kb transcript corresponds to the spliced message and the 5.8 kb transcripts to the unspliced genomic message (FIG. 21A). This verified the functionality of the 5'LTR and of the splice donor and acceptor in the virus. Similar results have been obtained with ψ-2G-MtkPL. Virus was prepared from the culture medium of ψ-2 cell lines.

Figure 22A:
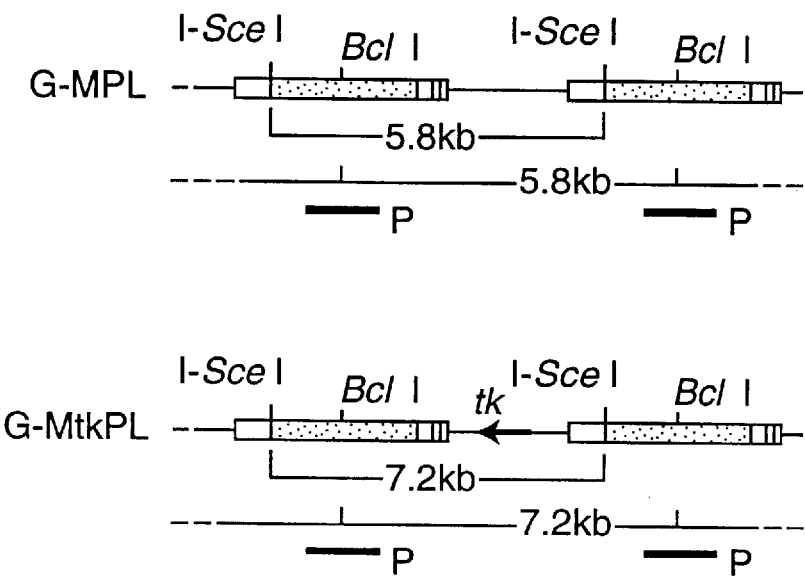
FIGS. 22A and B. A. Introduction of duplicated I-Sce I recognition sites into the genome of mammalian cells by retrovirus integration. Scheme of G-MPL and G-MtkPL proviruses which illustrates positions of the two LTRs and pertinent restriction sites. The size of Bcl I fragments and of I-Sce I fragments are indicated. Heavy bar is $^{32}$P radiolabelled LacZ probe (P). B. Southern blot analysis of cellular DNA from NIH3T3 fibroblasts cells infected by G-MtkPL and PCC7-S multipotent cells infected by G-MPL. Bcl I digests demonstrating LTR mediated PhleoLacZ duplication; I-Sce I digests demonstrating faithful duplication of I-Sce I sites.
Figure 22B:
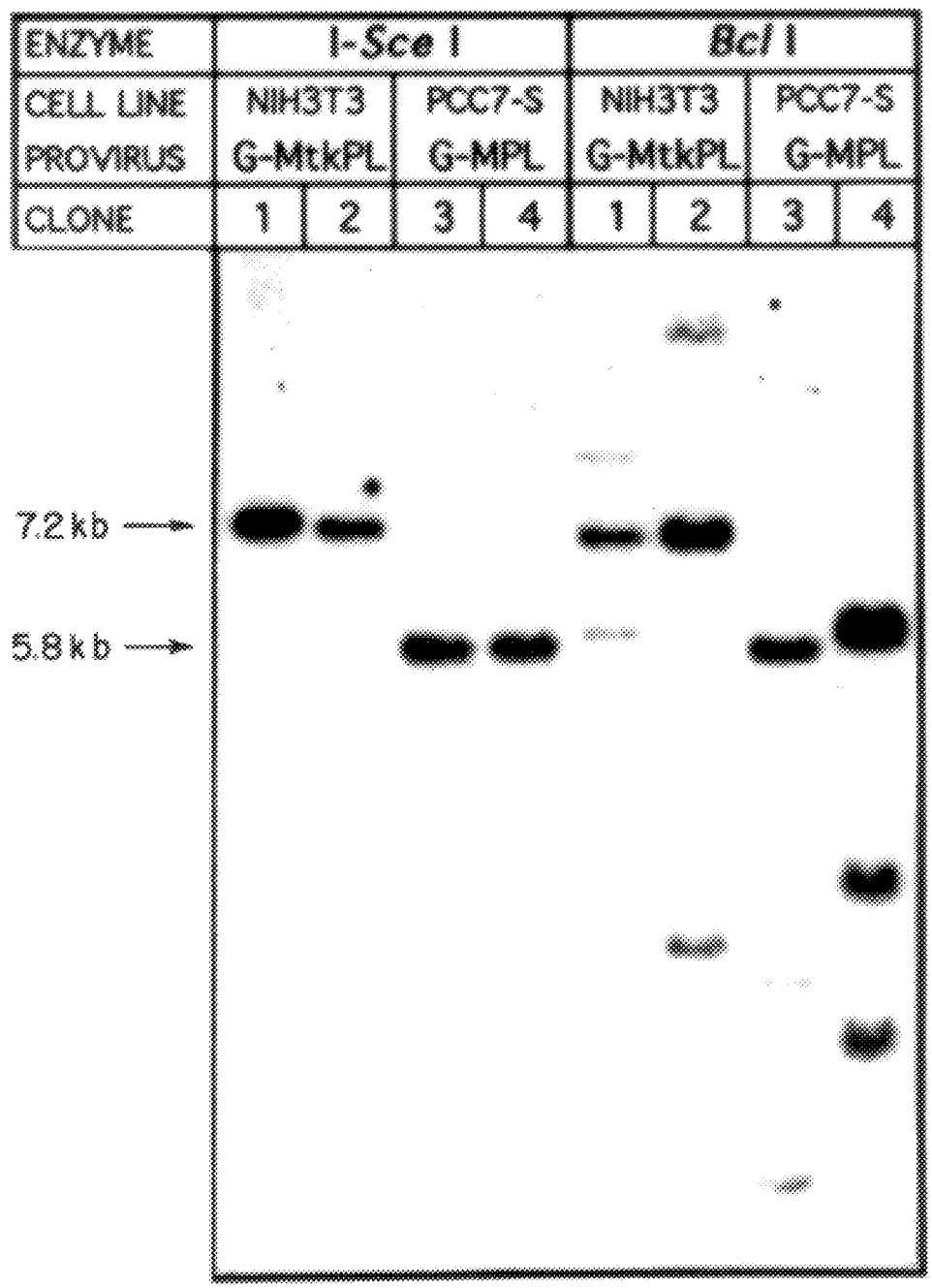

NIH3T3 fibroblasts and PCC7-S multipotent mouse cell lines (7B) were next infected by G-MtkPL and G-MPL respectively, and clones were isolated. Southern blot analysis of the DNA prepared from the clones demonstrated LTR-mediated duplication of I-Sce I PhleoLacZ sequences (FIG. 22a). Bcl I digestion generated the expected 5.8 kb (G-MPL) or 7.2 kb (G-MtkPL) fragments. The presence of two additional fragments corresponding to Bcl I sites in the flanking chromosomal DNA demonstrates a single proviral target in each clone isolated. Their variable size from clone to clone indicates integration of retroviruses at distinct loci. That I-Sce I recognition sites have been faithfully duplicated was shown by I-Sce I digests which generated 5.8 kb (G-MPL) fragments or 7.2 kb (G-MtkPL) (FIG. 22b).

Induction by I-Sce I of recombination leading to DNA exchange

The phenotype conferred to the NIH3T3 cells by G-MtkPL virus is phleo$^R$ β-gal$^+$ gls$^s$ and to PCC7-S by G-MPL is phleo$^R$ β-gal$^+$ (FIG. 20b). To allow for direct selection of recombination events induced by I-Sce I we constructed pVRneo donor plasmid. In pVRneo the neo gene is flanked by 300 bp homologous to sequences 5' to the left chromosomal break and 2.5 kb homologous to sequences 3' to the right break (FIG. 20d). A polyadenylation signal was positioned 3' to the neo gene to interrupt the PhleoLacZ message following recombination. If an induced recombination between the provirus and the plasmid occurs, the resulting phenotype will be neo$^R$ and due to the presence of a polyadenylation signal in the donor plasmid the PhleoLacZ gene should not be expressed, resulting in a phleo$^s$ β-gal$^{31}$ phenotype.

With G-MtkPL and G-MtkDPQPL, it is possible to select simultaneously for the gap by negative selection with the tk gene (with gancyclovir) and for the exchange of the donor plasmid with positive selection with the neo gene (with geneticine). With G-MPL only the positive selection can be applied in medium containing geneticine. Therefore, we expected to select for both the HR and for an integration event of the donor plasmid near an active endogenous promoter. These two events can be distinguished as an induced HR results in a neo$^R$ β-gal$^-$ phenotype and a random integration of the donor plasmid results in a neo$^R$ β-gal$^+$ phenotype.

Two different NIH3T3/G-MtkPL and three different PCC7S/3-MPL clones were then co-transfected with an expression vector for I-Sce I, pCMV(I-Sce I+), and the donor plasmid, pVRneo. Transient expression of I-Sce I may result in DSBs at I-Sce I sites, therefore promoting HR with pVRneo. The control is the co-transfection with a plasmid which does not express I-Sce I, pCMV(I-Sce I-), and pVRneo.

NIH3T3/G-MtkPL clones were selected either for loss of proviral sequences and acquisition of the neo$^R$ phenotype (with gancyclovir and geneticine) or for neo$^R$ phenotype only (Table 1). In the first case, neo$^R$ gls$^R$ colonies were recovered with a frequency of $10^{-4}$ in experimental series, and no colonies were recovered in the control series. In addition, all neo$^R$gls$^R$ colonies were β-gal$^-$, consistent with their resulting from HR at the proviral site. In the second case, neo$^R$ colonies were recovered with a frequency of $10^{-3}$ in experimental series, and with a 10 to 100 fold lower frequency in the control series. In addition, 90% of the neo$^R$ colonies were found to be β-gal$^-$ (in series with pCMV(I-Sce I+)). This shows that expression of I-Sce I induces HR between pVR neo and the proviral site and that site directed HR is ten times more frequent than random integration of pVR neo near a cellular promoter, and at least 500 times more frequent than spontaneous HR.

TABLE 1

Induced homologous recombination with I-Sce I

| Selection | G418 + Gls | | | | G418 | | | |
|---|---|---|---|---|---|---|---|---|
| I-Sce I expression | + | − | | | + | | − | |
| β-gal phenotype | + | − | + | − | + | − | + | − |
| (A) Cell line | | | | | | | | |
| NIH 3T3/G-MtkPL | | | | | | | | |
| Clone 1 | 0 | 66 | 0 | 0 | 69 | 581 | 93 | 0 |
| Clone 2 | 0 | 120 | 0 | 0 | 15 | 742 | 30 | 0 |
| PCC7-S/G-MPL | | | | | | | | |
| Clone 3 | | | | | 54 | 777 | 7 | 0 |
| Clone 4 | | | | | 2 | 91 | 1 | 0 |
| Clone 5 | | | | | 7 | 338 | 3 | 0 |
| (B) Molecular event | | | | | | | | |
| RI | 0 | | | | 8 | 1 | 6 | |
| DsHR | 15 | | | | 0 | 19 | 0 | |
| SsHR | 0 | | | | 0 | 4 | 0 | |
| Del | 0 | | | | 0 | 1 | 0 | |

TABLE 1

Figure 23A:
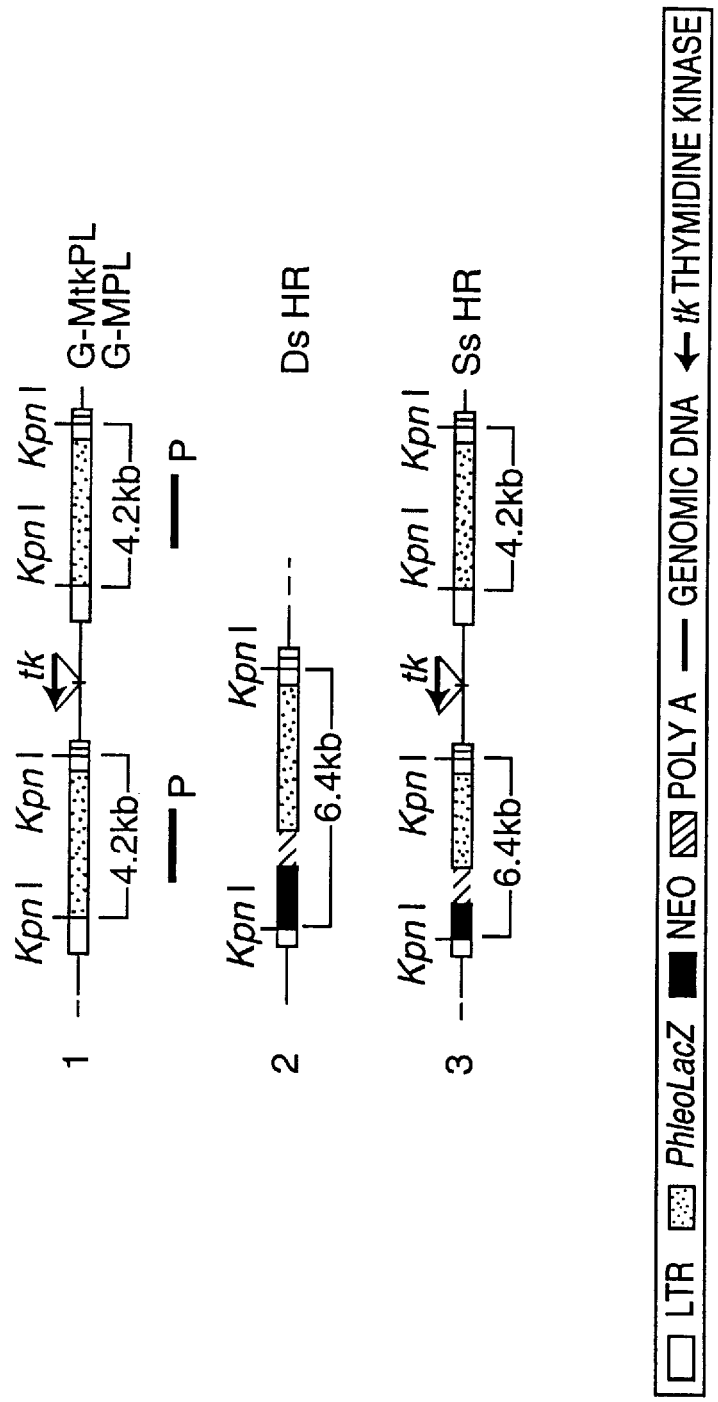
FIGS. 23A and B. Verification of recombination by Southern. A.: Expected fragment sizes in kilobase pairs (kb) of provirus at the recombinant locus. 1) the parental proviral locus. Heavy bar (P) is $^{32}$P radioactively labelled probe used for hybridization. 2) a recombinant derived after cleavage at the two I-Sce I sites followed by gap repair using pVR neo (double-site homologous recombination, DsHR). 3) a recombination event initiated by the cleavage at the I-Sce I sites in the left LTR (single-site homologous recombination, SsHR). B.: Southern analysis of DNA from NIH3T3/G-MtkPL clones 1 and 2, PCC7-S/G-MPL clones 3 and 4 and transformants derived from cotransfection with pCMV(I-Sce I+) and pVRneo (1a, 1b, 2a, 3a, 3b and 4a). Kpn I digestion of the parental DNA generates a 4.2 kb fragment containing LacZ fragment. Recombinants 1a and 3a are examples of DsHR Recombinants 1b, 2a, 3b and 4a are examples of SsHR.
Figure 23B:
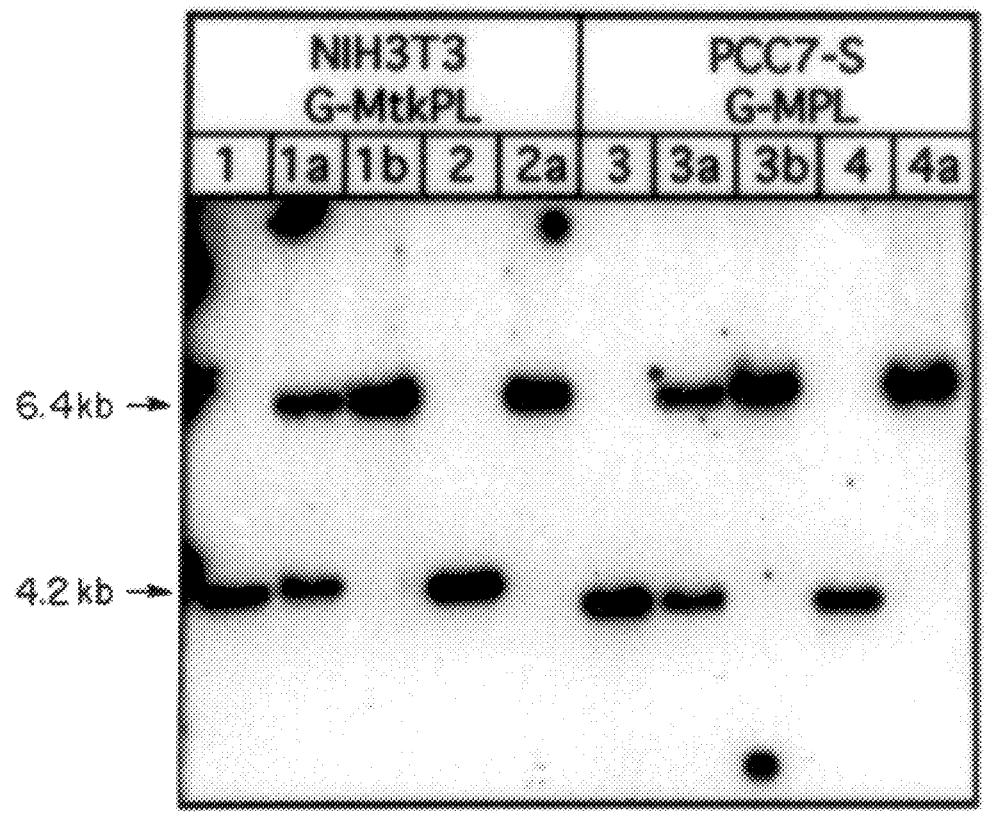

Effect of I-Sce I mediated double-strand cleavage. A. $10^6$ cells of NIH3T3/G-MtkPL clones 1 and 2 and $5.10^6$ cells of PCC7-S/G-MPL clones 3 to 5 were co-transfected with pVRneo and either pCMV(I-Sce I+) or pCMV(I-Sce I−). Cells were selected in the indicated medium: Geneticin (G418) or geneticin+gancyclovir (G418$_{13}$ Gls). The β-gal expression phenotype was determined by X-gal histochemical staining. If an induced recombination between the provirus and pVRneo occurs, the cells acquire a neo$^R$ β-gal$^-$ phenotype. B. Molecular analysis of a sample of recombinant clones. RI: random integration of pVRneo, parental proviral structure. DsHR: double site HR. SsHR: single site HR. Del: deletion of the provirus (see also FIGS. 20 and 23). Verification of recombination by Southern and Northern blot analysis The molecular structure of neo$^R$ recombinants has been examined by Southern blot analysis (FIG. 23 and Table 1). HR at I-Sce I sites predicts that digestion of recombinant DNA generates a 6.4 kb LacZ fragment instead of the 4.2 kb parental fragment. All 15 neo$^R$ gls$^R$ β-gal$^-$ recombinants from NIH3T3 cells exhibited only the 6.4 kb Kpn I fragment. Therefore, the double selection procedure leads to only the expected recombinants created by gene replacement (Double Site Homologous Recombinants, DsHR).

The 25 β-gal$^-$ recombinants generated from the single selection fell into four classes: (a) DsHR induced by I-Sce I as above (19 clones); (b) integration of pVRneo in the left LTR as proven by the presence of a 4.2 Kpn I fragment (corresponding to PhleoLacZ in the remaining LTR), in addition to the 6.4 kb fragment (FIG. 23, Table 1, Single site Homologous Recombinants, SsHR; 3 independent β-gal$^-$ recombinants from clone 3). These clones correspond to I-Sce I-IHR in left DSB only or (less likely) to double crossing over between LTR and pVRneo; (c) random pVRneo integrations (Table 1, Random Integrations, IR) and simultaneous HR (Table 1, Deletion, Del)(1 β-gal$^-$ recombinant); and (d) Random pVRneo integration and simultaneous deletion of provirus (1 β-gal$^-$ recombinant). We suggest that this fourth class corresponds to repair of DSBs with the homologous chromosome. As expected, all β-gal$^+$ recombinants from geneticin selection alone, correspond to random pVRneo integrations, whether they originate from the experimental series (eight clones analyzed) or from the control series (six clones analyzed).

Figure 24B:
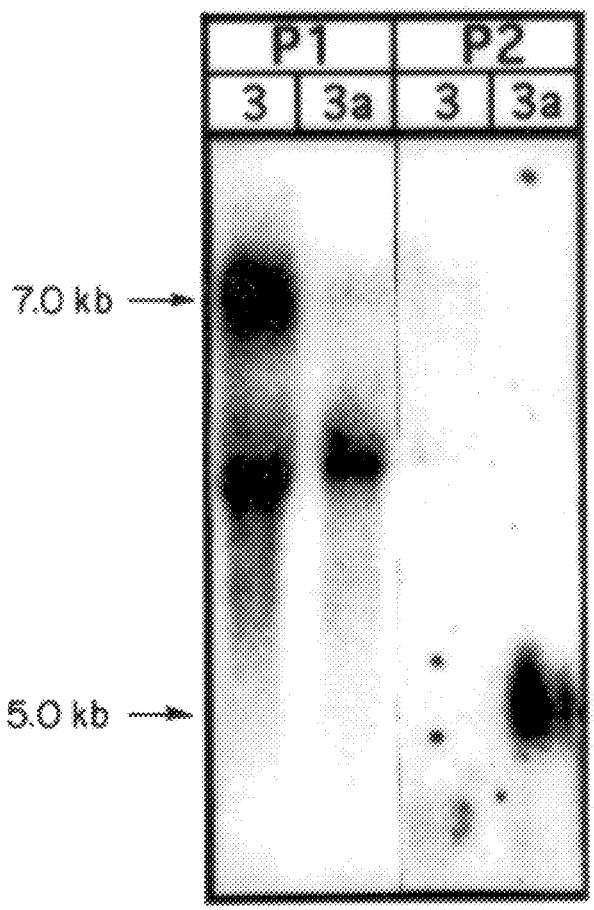
FIGS. 24A and B. Verification of recombination by Northern blot analyses. A.: Expected structure and sizes (in kb) of RNA from PCC7-S/G-MPL clone 3 cells before (top) and after (bottom) I-Sce I induced HR with pVRneo.1 Heavy bars P1 and P2 are $^{32}$P radioactively labelled probes. B.: Northern blot analysis of the PCC7-S/G-MPL clone 3 recombinant (total RNA). Lane 3 is parental cells, lane 3a recombinant cells. Two first lanes were probed with LacZ P1, two last lanes are probed with neo P2. parental PCC7-S/G-MPL clone 3 cells express a 7.0 kb LacZ RNA as expected of trapping of a cellular promoter leading to expression of a cellular-viral fusion RNA. The recombinant clone does not express this Lacz RNA but expresses a neo RNA of 5.0 kb, corresponding to the size expected for an accurate replacement of PhleoLacZ by neo gene.

We obtained additional evidence that recombination had occurred at the I-Sce I site of PCC7-S/G-MPL 1 by analyzing the RNAs produced in the parental cells and in the recombinant (FIG. 24). Parental PCC7-S/G-MPL 1 cells express a 7.0 kb LacZ RNA indicative of trapping of a cellular promoter leading to expression of a cellular-viral fusion RNA. The recombinant clone does not express this LacZ RNA but expresses a neo RNA of 5.0 kb. The size of the neo RNA corresponds to the exact size expected for an accurate exchange of PhleoLacZ by neo gene and uses of the same cellular and viral splice site (viral PhleoLacZ RNA in the LTR is 3.7 kb and neo RNA in pVRneo is 1.7 kb).

Discussion

The results presented here demonstrate that double-strand breaks can be induced by the I-Sce I system of *Saccharomyces cerevisiae* in mammalian cells, and that the breaks in the target chromosomal sequence induce site-specific recombination with input plasmidic donor DNA.

To operate in mammalian cells, the system requires endogenous I-Sce I like activity to be absent from mammalian cells and I-Sce I protein to be neutral for mammalian cells. It is unlikely that endogenous I-Sce I-like actively operates in mammalian cells as the introduction of I-Sce I recognition sites do not appear to lead to rearrangement or mutation in the input DNA sequences. For instance, all NIH3T3 and PCC7-S clones infected with a retroviruses containing the I-Sce I restriction site stably propagated the virus. To test for the toxicity of I-Sce I gene product, an I-Sce I expressing plasmid was introduced into the NIH3T3 cells line (data not shown). A very high percentage of cotransfer of a functional I-SceI gene was found, suggesting no selection against this gene. Functionality of I-Sce I gene was demonstrated by analysis of transcription, by immunofluorescence detection of the gene product and biological function (Choulika et al. in preparation).

We next tested whether the endonuclease would cleave a recognition site placed on a chromosome. This was accomplished by placing two I-Sce I recognition sites separated by 5.8 or 7.2 kb on a chromosome in each LTR of proviral structures and by analyzing the products of a recombination reaction with a targeting vector in the presence of the I-Sce I gene product. Our results indicate that in presence of I-Sce I, the donor vector recombines very efficiently with sequences within the two LTRs to produce a functional neo gene. This suggests that I-Sce I induced very efficiently double strand breaks in both I-Sce I sites. In addition, as double strand breaks were obtained with at least five distinct proviral insertions, the ability of I-Sce I protein to digest an I-Sce I recognition site is not highly dependent on surrounding structures.

The demonstration of the ability of the I-Sce I meganuclease to have biological function on chromosomal sites in mammalian cell paves the route for a number of manipulations of the genome in living organisms. In comparison with site-specific recombinases (9B, 18B), the I-Sce I system is non-reversible. Site specific recombinases locate not only the sites for cutting the DNA, but also for rejoining by bringing together the two partners. In contrast, the only requirement with the I-Sce I system is homology of the donor molecule with the region flanking the break induced by I-Sce I protein.

The results indicate for the first time that double strand DNA breaks in chromosomal targets stimulate HR with introduced DNA in mammalian cells. Because we used a combination of double strand breaks (DSB) in chromosomal recipient DNA and super-coiled donor DNA, we explored the stimulation by I-Sce I endonuclease of recombination by the double strand break repair pathway (21B). Therefore, the induced break is probably repaired by a gene conversion event involving the concerted participation of both broken ends which, after creation of single-stranded region by 5' to 3' exonucleolytic digestion, invade and copy DNA from the donor copy. However, a number of studies of recombination in mammalian cells and in yeast (10B, 11B, 19B) suggest that there is an alternative pathway of recombination termed single-strand annealing (SSA). In the SSA pathway, double-strand breaks are substrates in the action of an exonuclease that exposes homologous complementary single-strand DNA on the recipient and donor DNA. Annealing of the complementary strand is then followed by a repair process that generates recombinants. The I-Sce I system can be used to evaluate the relative importance of the two pathways.

EXAMPLE 5

This example describes the use of the I-Sce I meganuclease (involved in intron homing of mitochondria of the yeast *Saccharomyces cerevisiae*) (6B, 28B) to induce DSB and mediate recombination in mammalian cells. I-Sce I is a very rare-cutting restriction endonuclease, with an 18 bp long recognition site (29B, 22B). In vivo, I-Sce I endonuclease can induce recombination in a modified yeast nucleus by initiating a specific DBS leading to gap repair by the cell (30B, 17B, 21B). Therefore, this approach can potentially be used as a means of introducing specific DSB in chromosomal target DNA with a view to manipulate chromosomes in living cells. The I-Sce I-mediated recombination is superior to recombinase system [11B] for chromosome engineering since the latter requires the presence of target sites on both host and donor DNA molecules, leading to reaction that is reversible.

The I-Sce I endonuclease expression includes recombination events. Thus, I-Sce I activity can provoke site-directed double strand breaks (DSBs) in a mammalian chromosome. At least two types of events occur in the repair of the DSBs, one leading to intra-chromosomal homologous recombination and the other to the deletion of the transgene. These I-SceI-mediated recombinations occur at a frequency significantly higher than background.

MATERIALS AND METHODS

Plasmid construction pG-MtkPL was obtained in five steps: (I) insertion of the 0.3 kbp Bgl II-Sma I fragment (treated with Klenow enzyme) of the Moloney Murine Leukemia Virus (MoMuLV) env gene (25B) containing a splice acceptor (SA) between the Nhe I and Xba I sites (treated with Klenow enzyme), in the U3 sequence of the 3'LTR of MoMuLV, in an intermediate plasmid. (II) Insertion in this modified LTR of a 3.5 kbp Nco I-Xho I fragment containing the PhleoLacZ fusion gene [13B] (from pUT65; Cayla Laboratory, Zone Commerciale du Gros, Toulouse, France) at the Xba I site next to SA. (III) Insertion of this 3'LTR (containing SA and PhleoLacZ), recovered by Sal I-EcoR I double digestion in the p5'LTR plasmid (a plasmid containing the 5'LTR up to the nucleotide n° 563 of MoMuLV [12B] between the Xho I and the EcoR I site. (IV) Insertion of a synthetic I-Sce I recognition site into the Nco I site in the 3'LTR (between SA and PhleoLacZ), and (V) insertion (antisense to the retroviral genome) of the 1.6 kbp tk gene with its promoter with linker adaptators at the Pst I site of pG-MPL.

pCMV(I-Sce I+) was obtained in two steps: (I) insertion of the 0.73 kbp BamH I-Sal I, I-Sce I-containing fragment (from pSCM525, donated by A. Thierry) into the phCMV1 (donated by F. Meyer) plasmid cleaved with BamH I and Sal I, (II) insertion of a 1.6 kbp fragment (nucleotide n° 3204 to 1988 in SV40) containing the polyadenylation signal of SV40 at the Pst I site of phCMV1.

pCMV(I-Sce I−) contains the I-Sce I ORF in reverse orientation in the pCMV(I-Sce I+) plasmid. It was obtained by inserting the BamH I-Pst I I-Sce I ORF fragment (treated with Klenow enzyme) into the phCMV PolyA vector linearized by Nsi I and Sal I double-digestion and treated with Klenow enzyme.

Cell culture and selection

T3 and ψ 2 are referenced in (7B) and (13B). Cell selection medium: gancyclovir (14B, 23B) was added into the tissue culture medium at the concentration of 2 μM. Gancyclovir selection was maintained for 6 days. Phleomycine was used at a concentration of 10 μg/ml. Double selections were performed in the same conditions.

Transfection, infection, cell staining and nucleic acids blot analysis

These protocols were performed as described in (2B, 3B).

Virus-producing cell lines

The virus-producing cell line is generated by transfecting pG-MtkPL into the ψ-2 packaging cell line. Virus was prepared from the filtered culture medium of transfected ψ-2 cell lines. NIH3T3 fibroblasts were infected by G-MtkPL, and clones were isolated in a Phleomycin-containing medium.

Results

To assay for I-Sce I endonuclease activity in mammalian cells, NIH3T3 cells containing the G-MtkPL provirus were used. The G-MtkPL provirus (FIG. 25*a*) contains the tk gene (in place of the gag, pol and env viral genes), for negative selection in gancyclovir-containing medium and, in the two LTRs, an I-Sce I recognition site and the PhleoLacZ fusion gene. The PhleoLacZ gene can be used for positive selection of transduced cells in phleomycine-containing medium.

We hypothesized that the expression of I-Sce I endonuclease in these cells would induce double-strand breaks (DSB) at the I-Sce I recognition sites that would be repaired by one of the following mechanisms (illustrated in FIG. 25): a) if the I-Sce I endonuclease induces a cut in only one of the two LTRs (FIGS. 1-*b* 1 and 2), sequences that are homologous between the two LTRs could pair and recombine leading to an intra-chromosomal homologous recombination (i.e. by single strand annealing (SSA) (12B, 10B) or crossing-over); b) If the I-Sce I endonuclease induces a cut in each of the two LTRs, the two free ends can religate (end joining mechanism (31B) leading to an intra-chromosomal recombination (FIG. 25-b 3); or alternatively c) the gap created by the two DSBs can be repaired by a gap repair mechanism using sequences either on the homologous chromosome or on other chromosomal segments, leading to the loss of the proviral sequences (32B) (FIG. 25c).

The phenotype conferred to the NIH3T3 cells by the G-MtkPL provirus is Phleo$^R$β-Gal$^+$ Gls-$^s$. In a first series of experiments, we searched for recombination by selecting for the loss of the tk gene. NIH3T3/G-MtkPL 1 and 2 (two independent clones with a different proviral integration site) were transfected with the I-SceI expression vector pCMV (I-Sce I+) or with the control plasmid pCMV(I-Sce–) which does not express the I-Sce I endonuclease. The cells were then propagated in Gancyclovir-containing medium to select for the loss of tk activity. The resulting Gls$^R$ clones were also assayed for β-galactosidase activity by histochemical staining (with X-gal) (Table 1).

TABLE 1

Number and nature of Gls resistant clones

| I-Sce I expression | pCMV (I-SceI+) | | pCMV (I > SceI–) | |
|---|---|---|---|---|
| β-Gal activity | + | – | + | – |
| NIH3T3/G-MtkPL 1 | 11 | 154 | 0 | 0 |
| NIH3T3/G-MtkPL 2 | 16 | 196 | 2 | 0 |

TABLE 1

Effect of I-Sce I expression on recombination frequency. $1 \times 10^6$ cells of NIH3T3/G-MtkPL 1 and $2 \times 10^6$ cells of NIH3T3/G-MtkPL 1 were transfected with either pCMV(I-Sce I+) or pCMV(I-Sce I–). Cells were cultivated in medium containing gancyclovir. β-Galactosidase phenotype of the Gls$^R$ clones was determined by X-Gal histochemical staining.

Figure 26A:
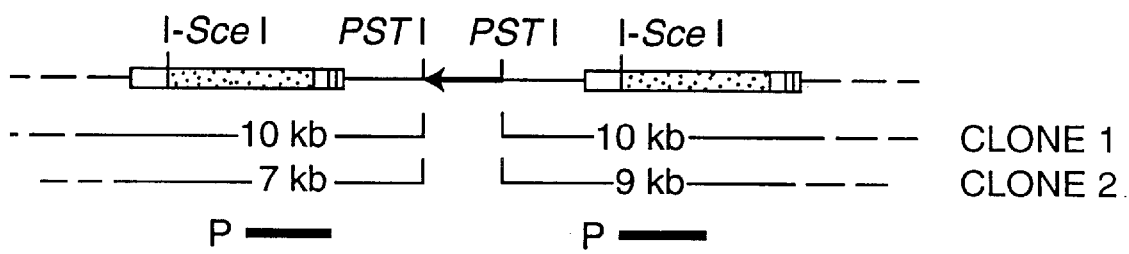
FIG. 26 (parts a and b ). Southern blot analysis of DNA from NIH3T3/G-MtkPL 1 and 2, and PhleoLacZ recombinants derived from transfections with pCMV(I-Sce I+) selected in Gancyclovir containing medium. a) Expected fragment sizes in kilobase pair (kbp) of parental provirus after digestion with Pst I endonuclease. Pst I digestion of the parental DNA NH3T3/G-MtkPL 1 generates two fragments of 10 kbp and on the parental NIH3T3/G-MtkPL 2 two fragments of 7 kbp and 9 kbp. b) Southern blot analysis of DNA digested by Pst I from NIH3T3/G-MtkPL 1, and recombinants derived from transfection with pCMV(I-Sce I+) (1.1 to 1.5). c) Southern blot analysis of DNA digested by Pst I from NIH3T3/G-MtkPL 2, and recombinants derived from transfection with pCMV(I-Sce I+) (2.1 to 2.6). Heavy bar is $^{32}$P radiolabelled LacZ probe (P)
Figure 26B:
Figure 26C:
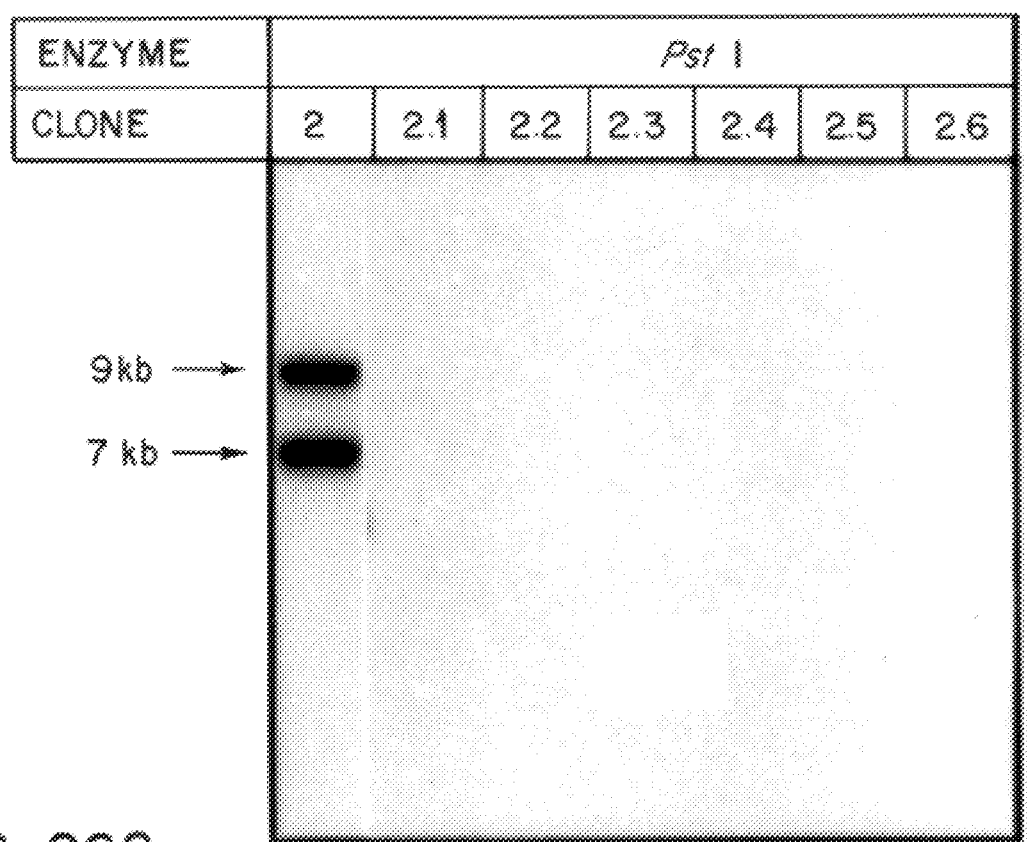

In the control series transfected with pCMV(I-SceI–), Gls$^R$ resistant clones were found at a low frequency (2 clones for $3 \times 10^{-6}$ treated cells) and the two were β-Gal$^+$. In the experimental series transfected with pCMV(I-SceI+), expression of the I-Sce I gene increased the frequency of Gls$^R$ clones 100 fold. These clones were either β-Gal$^-$ (93%) or β-Gal$^+$ (7%). Five β-Gal$^-$ clones from the NIH3T3/G-MtkPL 1 and six from the NIH3T3/G-MtkPL 2 were analyzed by Southern blotting using Pst I (FIG. 26). In the parental DNA, Pst I endonuclease cuts twice in the tk gene of the provirus (FIG. 26a). The sizes of the two PhleoLacZ containing fragments are determined by the position of the Pst I sites in the flanking cellular DNA. In NIH3T3/G-MtkPL 1, these two PhleoLacZ fragments are 10 kbp long and in NIH3T3/G-MtkPL 2 they are 7 and 9 kbp long. The five Gls$^R$ β-Gal$^-$ resistant clones from NIH3T3/G-MtkPL 1 and the six clones from tk NIH3T3/G-MtkPL 2 all showed an absence of tk gene and of the two PhleoLacZ sequences (FIGS. 26b and c).

In the experimental series the number of Gls$^R$ β-Gal$^+$ clones is increased about 10 fold by I-Sce I expression in comparison to the control series. These were not analyzed further.

In order to increase the number of Gls$^R$ β-Gal$^+$ clones recovered, in a second set of experiments, the cells were grown in a medium containing both Gancyclovir and Phleomycin. Gancyclovir selects for cells that have lost tk activity and Phleomycin for cells that maintained the PhleoLacZ gene. We transfected NIH3T3/G-MtkPLs 1 and 2 with pCMV(I-SceI+) or pCMV(I-SceI–) (Table 2).

TABLE 2

Number of Phleo and Gls resistant clones

| I-Sce I expression | pCMV (I-SceI+) | pCMV (I-SceI–) |
|---|---|---|
| NIH3T3/G-MtkPL 1 | 74 | 2 |
| NIH3T3/G-MtkPL 2 | 207 | 9 |

TABLE 2

Effect of I-Sce I expression on the intra-chromosomal recombination frequency. $2 \times 10^6$ cells of NIH3T3/G-MtkPL 1 and $9 \times 10^6$ cells of NIH3T3/G-MtkPL 2 were transfected with either pCMV(I-Sce I+) or pCMV(I-Sce I–). Cells were cultured in Phleomycin and gancyclovir containing medium.

In the control series, the frequency of recovery of Phleo$^R$ Gls$^R$ resistant clones was $1 \times 10^{-6}$. This result reflects cells that have spontaneously lost tk activity, while still maintaining the PhleoLacZ gene active. In the experimental series, this frequency was raised about 20 to 30 fold, in agreement with the first set of experiments (Table 1).

Figure 27B:
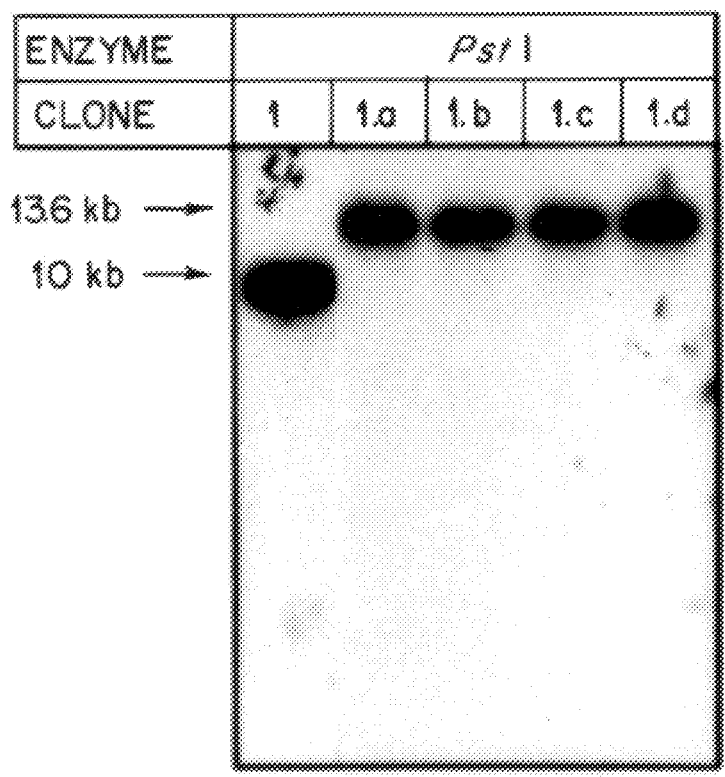
FIG. 27. Southern blot analysis of DNA from NIH3T3/G-MtkPL 1 and 2, and PhleoLacZ$^+$ recombinants derived from transfections with pCMV(I-Sce I+) and pCMV(I-Sce I–) and selection in Phleomycin and Gancyclovir containing medium. a) Expected fragment sizes in kbp of parental provirus after digestion with Pst I or Bcl I endonuclease. Pst I digestion of the parental DNA NIH3T3/G-MtkPL 1 generates two fragments of 10 kbp. Bcl I digestion of the parental DNA NIH3T3/G-MtkPL 2 generates three fragments of 9.2 kbp, 7.2 kbp and 6.0 kbp. a2) Expected fragment sizes in kbp of recombinants after digestion with Pst I or Bcl I endonuclease. Pst I digestion of DNA of the recombinant derived from NIH3T3/G-MtkPL 1 generates one fragment of 13.6 kbp. Bcl I digestion of the DNA of the recombinants derived from NIH3T3/G-MtkPL 2 generates two fragments of 9.2 kbp and 6.0 kbp. b) Southern blot analysis of DNA from NIH3T3/G-MtkPL 1, and recombinants derived from transfection with pCMV(I-Sce I–) and pCMV(I-Sce I+) (1c, 1d). c) Southern analysis of DNA from NIH3T3/G-MtkPL 2, and transformants derived from transfection with pCMV(I-Sce I–) (2a, 2b) and pCMV(I-Sce I+) (2c to 2h).

The molecular structure of the Phleo$^R$β-Gal$^+$Gls$^R$ clones was analyzed by Southern blotting (FIG. 27). Four clones from NIH3T3 G-MtkPL I were analyzed, two from the experimental series and two from the control. Their DNA was digested with Pst I endonuclease. If an intra-chromosomal event had occurred, we expected a single Pst I fragment of 13.6 kbp (that is the sum of the three Pst I fragments of the parental DNA minus the I-Sce I fragment, see FIG. 27a). All four Phleo$^R$Gls$^R$ resistant clones exhibited this 13.6 kbp Pst I fragment, suggesting a faithful intramolecular recombination (FIG. 27b).

Figure 27C:
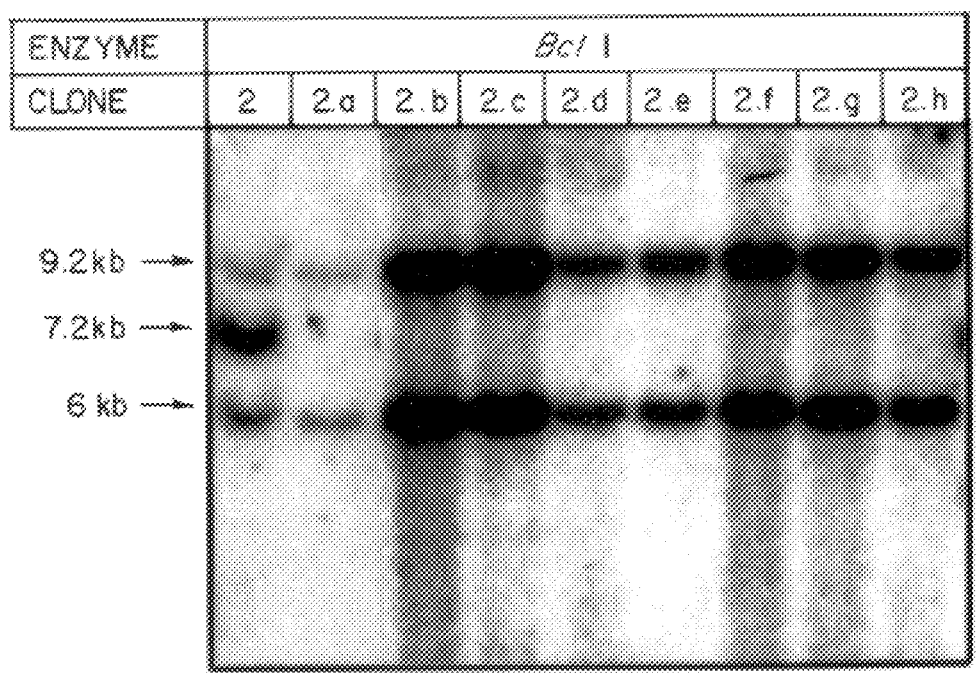

DNA from eight clones from NIH3T3/G-MtkPL 2 cells were analyzed by Southern blotting using Bcl I digestion (six frog the experimental series and two from the control). Bcl I digestion of the parental DNA results in one 7.2 kbp fragment containing the proviral sequences and in two flanking fragments of 6 kbp and 9.2 kbp. An intra-chromosomal recombination should result in the loss of the 7.2 kbp fragment leaving the two other bands of 6 kbp and 9.2 kbp unchanged (FIG. 27a). The eight clones (2.7 to 2.16) showed the disappearance of the tk containing 7.2 kbp fragment indicative of an intra-chromosomal recombination between the two LTRs (FIG. 27c).

Discussion

The results presented here demonstrate that the yeast I-Sce I endonuclease induces chromosomal recombination in mammalian cells. This strongly suggests that I-Sce I is able to cut in vivo a chromosome at a predetermined target.

Double-strand breaks in genomic sequences of various species stimulate recombination (21B, 19B). In the diploid yeast, a chromosomal DSB can lead to the use of the homo-allelic locus as repair matrix. This results in a gene conversion event, the locus then becoming homozygous (30B). The chromosomal DSBs can also be repaired by using homologous sequences of an ectopic locus as matrix (32B). This result is observed at a significant level as a consequence of a DSB gap repair mechanism. If the DSB occurs between two direct-repeated chromosomal sequences, the mechanism of recombination uses the single strand annealing (SSA) pathway (11B, 10B). The SSA pathway involves three steps: 1) an exonucleolysis initiated at the point of the break leaving 3' protruding single-strand DNAs; 2) a pairing of the two single strand DNAs by their homologous sequences, 3) a repair of the DNA by repairs complexes and mutator genes which resolve the nonhomologous sequences (33B). A special case concerns the haploid yeast for which it has been showed that DSBs induced by HO or I-SceI endonucleases in a chromosome leads to the repair of the break by end joining (34B). This occurs, but at a low efficiency (30B, 35B).

Our results show that the presence of two I-Sce I sites in a proviral target and the expression of the I-Sce I endonuclease lead to an increase in the deletion of a thymidine kinase gene at a frequency at least 100 fold greater than that occurring spontaneously. Two types of tk deleted clones arise from I-Sce I mediated recombination: clones that have kept (7%) and clones that have lost (93%) the PhleoLacZ sequences.

The generation of tk$^-$PhleoLacZ$^+$ cells is probably the consequence of intra-chromosomal recombination. Studies have shown that in a recombinant provirus with an I-Sce I recognition site in the LTRs, the I-Sce I endonuclease leads in 20% of the cases to the cleavage of only one proviral I-Sce I site and in 80% to the cleavage of the two proviral I-Sce I sites. If only one of the two I-Sce I sites is cut by the endonuclease, an intra-chromosomal recombination can occur by the SSA pathway. If the two I-Sce I sites are cut, the tk$^-$PhleoLacC$^+$ cells can be generated by end joining, allowing intra-chromosomal recombination (see FIG. 1). Although, in the diploid yeast, this pathway is not favorable (the break is repaired using homologous chromosomal sequences) (2B), it remains possible that this pathway is used in mammalian cells.

The generation of tk$^-$/PhleoLacZ$^-$cells is probably a consequence of either a homo-allelic and/or an ectopic gene conversion event (36B). Isolation and detailed molecular analysis of the proviral integration sites will provide information on the relative frequency of each of these events for the resolution of chromosomal DSBs by the cell. This quantitative information is important as, in mammalian cells, the high redundancy of genomic sequences raises the possibility of a repair of DSBs by ectopic homologous sequences. Ectopic recombination for repair of DSBs may be involved in genome shaping and diversity in evolution [29].

The ability to digest specifically a chromosome at a predetermined genomic location has several potential applications for genome manipulation.

The protocol of gene replacement described herein can be varied as follows:

Variety of donor vectors

Size and sequence of flanking regions of I-Sce-I site in the donor plasmid (done with 300 pb left and 2.5 kb right): Different constructions exist with various size of flanking regions up to a total of 11 kb left and right from I-Sce I site. The sequences depend from the construction (LTR, gene). Any sequence comprising between 300 bp to 11 kb can be used.

Inserts (neo, phleo, phleo-LacZ and Pytk-neo have been constructed). Antibiotic resistance: neomycin, phleomycin; reporter gene (LacZ); HSV1 thymidine kinase gene: sensitivity to gancyclovir. It is impossible to insert any kind of gene sequence up to 10 kb or to replace it. The gene can be expressed under an inducible or constitutive promoter of the retrovirus, or by gene trap and homologous recombination (i.e. Insulin, Hbs, ILs and various proteins).

Various methods can be used to express the enzyme I-Sce I: transient transfection (plasmid) or direct injection of protein (in embryo nucleus); stable transfection (various promoters like: CMV, RSV and MoMuLV); defective recombinant retroviruses (integration of ORF in chromosome under MoMuLV promoter); and episomes.

Variation of host range to integrate I-Sce I site:

Recombinant retroviruses carrying I-Sce I site (i.e. pG-MPL, pG-MtkPL, pG-Mtk$_A$PAPL) may be produced in various packaging cell lines (amphotropic or xenotropic).

Construction of stable cell lines expressing I-Sce I and cell Protection against retroviral infection Stable cell line expressing I-Sce I are protected against infection by a retroviral vector containing I-Sce I site (i.e. NI 3T3 cell line producing I-Sce I endonuclease under the control of the CMV promoter is resistant to infection by a pG-MPL or pGMtkPL or I-Sce I under MoMuLV promoter in $\psi$ 2 cells).

Construction of cell lines and transgenic animals containing the I-Sce I site

Insertion of the I-Sce I site is carried out by a classical gene replacement at the desired locus and at the appropriate position. It is then possible to screen the expression of different genes at the same location in the cell (insertion of the donor gene at the artificially inserted I-Sce I site) or in a transgenic animal. The effect of multiple drugs, ligands, medical protein, etc., can be tested in a tissue specific manner. The gene will consistently be inserted at the same location in the chromosome.

For "Unprepared" mouse cells, and all eucaryotic cells, a one step gene replacement/integration procedure is carried out as follows:

Vectors (various donor plasmids) with I-Sce I site: one site within the gene (or flanking) or two sites flanking the donor gene.

Method to express the enzyme

Transient expression: ORF on the same plasmid or another (cotransfection).

Specific details regarding the methods used are described above. The following additional details allow the construction of the following:

a cell line able to produce high titer of a variety of infective retroviral particles;

plasmid containing a defective retrovirus with I-Sce I sites reporter-selector gene, active LTRs and other essential retroviral sequence; a plasmid containing sequences homologous to flanking regions of I-Sce I sites in above engineered retrovirus and containing a multiple cloning site; and a vector allowing expression of I-Sce I endonuclease and adapted to the specific applications.

Mouse fibroblast $\psi$2 cell line was used to produce ectopic defective recombinant retroviral vectors containing I-Sce I sites. Cell lines producing plasmids as pG-MPL, pG-MtkPL, PG-Mtk$_{66\ PA}$PL are also available. In addition, any cells, like mouse amphotropic cells lines (such as PA12) or xenotropic cells lines, that produce high titer infectious particles can be used for the production of recombinant retroviruses carrying I-Sce I site (i.e., pG-MPL, pG-MtkPL, pG-Mtk$_{APA}$PL) in various packaging cell lines (amphotropic, ectropic or xenotropic).

A variety of plasmids containing I-Sce I can be used in retroviral construction, including pG-MPL, pG-MtkPL, and pG-MtkΔPAPL. Others kind of plasmid vector can be constructed containing various promoters, genes, polyA site, and I-Sce I site. A variety of plasmid containing sequences homologs to flanking regions of I-Sce I can be constructed. The size and sequence of flanking regions of I-Sce I site in the donor plasmid are prepared such that 300 kb are to the left and 2.5 kb are to the right). Other constructions can be used with various sizes of flanking regions of up to about 11 kb to the left and right of the I-Sce I recognition site.

Inserts containing neomycin, phleomycin and phleo-LacZ have been constructed. Other sequences can be inserted such as drug resistance or reporter genes, including LacZ, HSV1 or thymidine kinase gene (sensibility to gancyclovir), insulin, CFTR, IL2 and various proteins. It is normally possible to insert any kind of sequence up to 12 kb, wherein the size depends on the virus capacity of encapsidation). The gene can be expressed under inducible or constitutive promoter of the retrovirus, or by gene trap after homologous recombination.

A variety of plasmids containing I-Sce I producing the endonuclease can be constructed. Expression vectors such as pCMVI-SceI(+) or similar constructs containing the ORF, can be introduced in cells by transient transfection, electroporation or lipofection. The protein can also be introduced directly into the cell by injection of liposomes.

Variety of cells lines with integrated I-Sce I sites can be produced. Preferably, insertion of the retrovirus (proviral integration) induce duplication of LTR containing the I-Sce I site. The cell will be hemizygote for the site. Appropriate cell lines include:

1. Mouse Fibroblastic cell line, NIH 3T3 with 1 to 4 proviral integration of G-MPL. Multiple (more than 30) clones were recovered. The presence of and the multiplicity of the different genomic integrations (uncharacterized) were verified by molecular analysis.
2. Mouse Fibroblastic cell line, NIH 3T3 with 1 copy of G-MtkPL integrated in the genome. 4 clones were covered.
3. Mouse Embryonal Carcinoma cell line, PCC7-S with 1 to 4 copies of G-MPL proviral integration in the genome. 14 clones were covered.
4. Mouse Embryonal Carcinoma cell line, PCC4 with 1 copy of G-MtkPL integrated in the genome.
5. Mouse Embryonic Stem cell line D3 with 1 to 4 copies of G-MPL at a variety of genomic localisation (uncharacterized). 4 clones were recovered.

Construction of other cell lines and transgenic animals containing the I-Sce I site can be done by insertion of the I-Sce I site by a classical gene replacement at the desired locus and at the appropriate position. Any kind of animal or plant cell lines could a priori be used to integrate I-Sce I sites at a variety of genomic localisation with cell lines adapted. The invention can be used as follows:

1. Site specific gene insertion

The methods allow the production of an unlimited number of cell lines in which various genes or mutants of a given gene can be inserted at the predetermined location defined by the previous integration of the I-Sce I site. Such cell lines are thus useful for screening procedures, for phenotypes, ligands, drugs and for reproducible expression at a very high level of recombinant retroviral vectors if the cell line is a transcomplementing cell line for retrovirus production.

Above mouse cells or equivalents from other vertebrates, including man, can be used. Any plant cells that can be maintained in culture can also be used independently of whether they have ability to regenerate or not, or whether or not they have given rise to fertile plants. The methods can also be used with transgenic animals.

2. Site specific gene expression

Similar cell lines can also be used to produce proteins, metabolites or other compounds of biological or biotechnological interest using a transgene, a variety of promoters, regulators and/or structural genes. The gene will be always inserted at the same localisation in the chromosome. In transgenic animals, it makes possible to test the effect of multiple drugs, ligands, or medical proteins in a tissue-specific manner.

3. Insertion of the I-Sce I recognition site in the CFTR locus using homologous sequences flanking the CFTR gene in the genomic DNA. The I-Sce I site can be inserted by spontaneous gene replacement by double-crossing over (Le Mouellic et al. PNAS, 1990, Vol. 87, 4712–4716).

4. Biomedical applications

A. In gene therapy, cells from a patient can be infected with a I-Sce I containing retrovirus, screened for integration of the defective retrovirus and then co-transformed with the I-Sce I producing vector and the donor sequence.

Examples of appropriate cells include hematopoeitic tissue, hepatocytes, skin cells, endothelial cells of blood vessels or any stem cells.

I-Sce I containing retroviruses include pG-MPL, pG-MtkPL or any kind of retroviral vector containing at least one I-Sce I site.

I-Sce I producing vectors include pCMVI-Sce I(+) or any plasmid allowing transient expression of I-Sce I endonuclease.

Donor sequences include (a) Genomic sequences containing the complete IL2 gene; (b) Genomic sequences containing the pre-ProInsulin gene; (c) A large fragment of vertebrate, including human, genomic sequence containing cis-acting elements for gene expression. Modified cells are then reintroduced into the patient according to established protocols for gene therapy.

B. Insertion of a promoter (i.e., CMV) with the I-Sce I site, in a stem cell (i.e., lymphoid). A gap repair molecule containing a linker (multicloning site) can be inserted between the CMV promoter and the downstream sequence. The insertion of a gene (i.e., IL-2 gene), present in the donor plasmids, can be done efficiently by expression of the I-Sce I meganuclease (i.e., co-transfection with a I-Sce I meganuclease expression vector). The direct insertion of IL-2 gene under the CMV promoter lead to the direct selection of a stem cell over-expressing IL-2.

For constructing transgenic cell lines, a retroviral infection is used in presently available systems. Other method to introduce I-Sce I sites within genomes can be used, including micro-injection of DNA, Ca-Phosphate induced transfection, electroporation, lipofection, protoplast or cell fusion, and bacterial-cell conjugation.

Loss of heterozygosity is demonstrated as follows: The I-Sce I site is introduced in a locus (with or without foreign sequences), creating a heterozygous insertion in the cell. In the absence of repair DNA, the induced double-strand break will be extend by non-specific exonucleases, and the gap repaired by the intact sequence of the sister chromatide, thus the cell become homozygotic at this locus.

Specific examples of gene therapy include immunomodulation (i.e. changing range or expression of IL genes); replacement of defective genes; and excretion of proteins (i.e. expression of various secretory protein in organelles).

It is possible to activate a specific gene in vivo by I-Sce I induced recombination. The I-Sce I cleavage site is introduced between a duplication of a gene in tandem repeats, creating a loss of function. Expression of the endonuclease I-Sce I induces the cleavage between the two copies. The reparation by recombination is stimulated and results in a functional gene.

Site-directed genetic macro-rearrangements of chromosomes in cell lines or in organisms Specific translocation of chromosomes or deletion can be induced by I-Sce I cleavage. Locus insertion can be obtained by integration of one at specific location in the chromosome by "classical gene replacement." The cleavage of recognition sequence by I-Sce I endonuclease can be repaired by non-lethal translocations or by deletion followed by end-joining. A deletion of a fragment of chromosome could also be obtained by insertion of two or more I-Sce I sites in flanking regions of a locus (see FIG. 32). The cleavage can be repaired by recombination and results in deletion of the complete region between the two sites (see FIG. 32).

References

1B. Bernstein, N., Pennell, N., Ottaway, C. A. and Shulman, M. J. 1992. Gene replacement with one-sided homologous recombination. Mol. Cell Biol. 12:360–367.

2B. Bonnerot, C., Legouy, E., Choulika, A. and Nicolas, J.-F. 1992. Capture of a cellular transcriptional unit by retrovirus: mode of provirus activation in embryonal carcinoma cells. J. Virol. 66:4982–4991.

3B. Bonnerot, C., and Nicolas, J.-F. 1993. Application or LacZ gene fusions to post-implantation development. In "Methods in Enzymology: Guide to techniques in mouse development". 45–469. Wassarman, P. M., DePamphilis, M. L.

4B. Brenner, D. A., Smogocki, A. and Camerini-Otero, R. D. 1986. Double-strand gap repair results in homologous recombination in mouse L cells. Proc. Natl. Acad. Sci. USA. 83:1762–1766.

5B. Capecchi, M. R. 1989. Altering the genome by homologous recombination. Science. 244:1288–1292.

6B. Jacquier, A. and Dujon, B. 1985. An intron encoded protein is active in a gene conversion process that spreads an intron into a mitochondrial gene. Cell. 41:383–394.

7B. Jakob, H. and Nicolas, J. F. 1987. Mouse Tertocarcinoma Cells. In "Methods in Enzymology: Cell lines for genetic analysis". 66–81. Gottesman, M. H., ed., Academic Press.

8. Jessberger, R. and Berg, P. 1991. Repair of deletions and double-strand gaps by homologous recombination in a mammalian in vitro system. Mol. Cell Biol. 11:445–457.

9B. Kilby, N. J., Snaith, M. R. and Murray, J. A. H. 1993. Site-specific recombinases: tools for genome engineering. Reviews. 9:413–421.

10B. Lin, F. L. M., Sperle, K. and Sternberg N. 1990. Repair of double-stranded DNA breaks by homologous DNA fragments during transfer of DNA into mouse L cells. Mol. Cell Biol. 10:113–119.

11B. Lin, F. L. M., Sperle, K. and Sternberg N. 1990. Intermolecular recombination between DNAs introduced into mouse L cells is mediated by a nonconservative pathway that leads to crossover products. Mol. Cell Biol. 10:103–112.

12B. Lin, F. L. M., Sperle, K. and Sternberg N. 1990. Intermolecular recombination between DNAs introduced into mouse L cells is mediated by a nonconservative pathway that leads to crossover products. Mol. Cell. Biol. 10:103–112.

13B. Mann, R., Mulligan, R. C. and Baltimore, D. 1983. Construction of a retrovirus packaging mutant and its use to produce helper-free defective retrovirus. Cell. 33:153–163.

14B. Mansour, S. L., Thomas K. R. and Capecchi, M. R. 1988. Disruption of the proto-oncogene int-2 in mouse embryo-derived stem cells: a general strategy for targeting mutations to non-selectable gene. Nature. 336:348–352.

15B. Mulsant, P., Gatignol, A., Dolens, M. and Tiraby, G. 1988. Somat. Cell. Mol. Genet. 14:243–252.

16B. Nicolas, J. F. and Rubenstein, J. 1987. Retroviral vectors. Boston London Durban Singapore Sydney Toronto Wellington, Butterworths.

17B. Plessis, A., Perrin, A., Haber, J. E. and Dujon, B. 1992. Site specific recombination determined by I-Sce I, a mitochondrial group I intron-encoded endonuclease expressed in the yeast nucleus. Genetics 130:451–460.

18B. Sauer, B. and Henderson, N. 1988. Site-specific DNA recombination in mammalian cells by the Cre recombinase of bacteriophage P1. Prac. Natl. Acad. Sci. USA. 85:5166–517.

19B. Seidman, M. M. 1987. Intermolecular homologous recombination between transfected sequences in mammalian cells is primarily nonconservative. Mol. Cell. Biol. 7:3561–3565.

20B. Smithies, O., Gregg, R. G., Boggs, S. S., Koralewski, M. A. and Kucherlapati, R. S. 1985. Insertion of DNA sequences into the human chromosomal B-globin locus by homologous recombination. Nature. 317:230–234.

21B. Szostak, J. W., Orr-Weaver, T. L. and Rothstein, R. J. 1983. The double-strand break repair model for recombination. Cell. 33:25–35.

22B. Thierry, A., Perrin, A., Boyer, J., Fairhead, C., Dujon, B., Frey, B. and Schmitz, G. 1991. Cleavage of yeast and bacteriophage T7 genomes at a single site using the rare cutter endonuclease I-Sce I. Nucleic Acids Res. 19:189–90.

23B. Tybulewicz, V. L. J., Crawford, C. E., Jackson, P. K., Bronson, R. T. and Mulligan, R. C. 1991. Neonatal Lethality and Lymphopenia in Mice with a Homozygous Disruption of the c-abl Proto-Oncogene. Cell 65:1153–1163.

24B. Varmus, H. and Brown, P., Retroviruses in Mobile DNA, 58–108 (Douglas E. Berg and Martha H. Howe eds., 1989).

25B. Weiss, R., Teich, N., Varmus, H. and Coffin, J. 1985. RNA tumor viruses. Molecular Biology of tumor viruses. Second Edition. 2) Supplements and appendixes. Cold Spring Harbor Laboratory. 1–1222.

26B. Weiss, R., Teich, N., Varmus, H. and Coffin, J. 1985. RNA tumor viruses. Molecular Biology of tumor viruses. Second Edition. 2) Supplements and appendixes. Cold Spring Harbor Laboratory. 1–1222.

27B. Phillips J. and Morgan W. 1994. Illegitimate recombination induced by DNA double-strand breaks in mammalian chromosomes. Molecular and Cellular Biology 14:5794–5803.

28B. Dujon B. 1989. Group I introns are mobile genetic elements: facts and mechanistic speculations-a review. Gene 82:91–114.

29B. Colleaux L., D'Aurio L., Galibert F. and Dujon B. 1988. Recognition and cleavage site of the intron-encoded omega transposase. Proc Natl Acad Sci USA 85:6022–6.

30B. Fairchild C. and Dujon B. Consequences of unique double-stranded breaks in yeast chromosomes: death or homozygosis. Molecular general genetics 240:170–180.

31B. Pfeiffer P., Thode S., Hancke J. and Vielmetter W. 1994. Mechanism of overlap information in nonhomologous DNA end joining. Molecular and Cellular Biology 14:888–895.

32B. Mezard C. and Nicholas A. 1994. Homologous, homeologous, and illegitimate repair of double-strand breaks during transformation of a wild-type strain and a rad52 Mutant strain of *Saccharomyces cerevisiae*. Molecular and Cellular Biology 14:1278–1292.

33B. Feaver W. J., Svejstrup J. Q., Bradwell L., Bradwell A. J., Buratowski S., Gulyas K., Donahue T. F., Friedberg E. C. and Kornberg R. D. 1993. Dual Roles of a Multiprotein Complex from *S. cerevisiae* in transcription and DNA Repair. Cell 75:1379–1387.

34B. Kramer K., Brock J., Bloom K., Moore K. and Haber J. 1994. Two different types of double-strand breaks in *Saccharomyces cerevisiae* are repaired by similar RAD52 independent, nonhomologous recombination events. Molecular and Cellular Biology 14:1293–1301.

35B. Weiffenbach B. and Haber J. 1981. Homothallelic mating type switching generates lethal chromosomes breaks in rad52 strains of *Saccharomyces cerevisiae*. Molecular and Cellular Biology 1:522–534.

36. Nassif N., Penney J., Pal S., Engels W. and Gloor G. 1994. Efficient copying of nonhomologous sequences from ectopic sites via P-element-induced gap repair. Molecular and cellular biology 14:1643–1625.

37B. Charlesworth B., Sniegowski P. and Stephan W. 1994. The evolutionary dynamics of repetitive DNA in eucaryotes. Nature 371:215–220.

We claim:

1. A host cell transformed with a vector comprising the DNA sequence encoding the enzyme I-SceI, wherein said DNA sequence corresponds to SEQ ID NO: 1.

2. The host cell of claim 1, wherein said vector is a plasmid.

3. The host cell of claim 2, wherein said plasmid is pSCM525.

4. The host cell of claim 1, wherein said host cell is *E. coli*.

5. The host cell of claim 4, wherein said host cell is *E. coli* strain TG1 having the accession number C.N.C.M. I-1014.

6. A method of producing an I-Sce I enzyme, comprising the steps of
   (a) culturing the transformed host of claim 1 in a medium and under conditions that allow expression of the DNA encoding the I-Sce I enzyme; and
   (b) harvesting the I-Sce I enzyme.

7. A purified I-Sce I enzyme produced by the method of claim 6.

8. A purified I-Sce I enzyme encoded by the nucleotide sequence of Seq. I.D. No. 1.

* * * * *

SEQUENCE LISTING ( 1 ) GENERAL INFORMATION:

( i i i ) NUMBER OF SEQUENCES: 52

( 2 ) INFORMATION FOR SEQ ID NO:1:

( i ) SEQUENCE CHARACTERISTICS:
( A ) LENGTH: 714 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
ATGCATATGA  AAAACATCAA  AAAAAACCAG  GTAATGAACC  TCGGTCGAA   CTCTAAACTG    60
CTGAAAGAAT  ACAAATCCCA  GCTGATCGAA  CTGAACATCG  AACAGTTCGA  AGCAGGTATC   120
GGTCTGATCC  TGGGTGATGC  TTACATCCGT  TCTCGTGATG  AAGGTAAAAC  CTACTGTATG   180
CAGTTCGAGT  GGAAAAACAA  AGCATACATG  GACCACGTAT  GTCTGCTGTA  CGATCAGTGG   240
GTACTGTCCC  CGCCGCACAA  AAAAGAACGT  GTTAACCACC  TGGGTAACCT  GGTAATCACC   300
TGGGGCGCCC  AGACTTTCAA  ACACCAAGCT  TTCAACAAAC  TGGCTAACCT  GTTCATCGTT   360
AACAACAAAA  AAACCATCCC  GAACAACCTG  GTTGAAAACT  ACCTGACCCC  GATGTCTCTG   420
GCATACTGGT  TCATGGATGA  TGGTGGTAAA  TGGGATTACA  ACAAAAACTC  TACCAACAAA   480
TCGATCGTAC  TGAACACCCA  GTCTTTCACT  TTCGAAGAAG  TAGAATACCT  GGTTAAGGGT   540
CTGCGTAACA  AATTCCAACT  GAACTGTTAC  GTAAAAATCA  ACAAAAACAA  ACCGATCATC   600
TACATCGATT  CTATGTCTTA  CCTGATCTTC  TACAACCTGA  TCAAACCGTA  CCTGATCCCG   660
CAGATGATGT  ACAAACTGCC  GAACACTATC  TCCTCCGAAA  CTTTCCTGAA  ATAA         714
```

( 2 ) INFORMATION FOR SEQ ID NO:2:

( i ) SEQUENCE CHARACTERISTICS:
( A ) LENGTH: 237 amino acids
( B ) TYPE: amino acid
( D ) TOPOLOGY: linear ( i i ) MOLECULE TYPE: peptide ( x i ) SEQUENCE DESCRIPTION: SEQ ID NO:2:

```
Met His Met Lys Asn Ile Lys Lys Asn Gln Val Met Asn Leu Gly Pro
 1               5                  10                  15
Asn Ser Lys Leu Leu Lys Glu Tyr Lys Ser Gln Leu Ile Glu Leu Asn
             20                  25                  30
Ile Glu Gln Phe Glu Ala Gly Ile Gly Leu Ile Leu Gly Asp Ala Tyr
         35                  40                  45
Ile Arg Ser Arg Asp Glu Gly Lys Thr Tyr Cys Met Gln Phe Glu Trp
     50                  55                  60
```

```
Lys  Asn  Lys  Ala  Tyr  Met  Asp  His  Val  Cys  Leu  Leu  Tyr  Asp  Gln  Trp
 65                  70                  75                       80

Val  Leu  Ser  Pro  Pro  His  Lys  Lys  Glu  Arg  Val  Asn  His  Leu  Gly  Asn
                85                  90                       95

Leu  Val  Ile  Thr  Trp  Gly  Ala  Gln  Thr  Phe  Lys  His  Gln  Ala  Phe  Asn
               100                 105                      110

Lys  Leu  Ala  Asn  Leu  Phe  Ile  Val  Asn  Asn  Lys  Lys  Thr  Ile  Pro  Asn
          115                     120                      125

Asn  Leu  Val  Glu  Asn  Tyr  Leu  Thr  Pro  Met  Ser  Leu  Ala  Tyr  Trp  Phe
     130                     135                 140

Met  Asp  Asp  Gly  Gly  Lys  Trp  Asp  Tyr  Asn  Lys  Asn  Ser  Thr  Asn  Lys
145                      150                 155                           160

Ser  Ile  Val  Leu  Asn  Thr  Gln  Ser  Phe  Thr  Phe  Glu  Glu  Val  Glu  Tyr
               165                      170                           175

Leu  Val  Lys  Gly  Leu  Arg  Asn  Lys  Phe  Gln  Leu  Asn  Cys  Tyr  Val  Lys
               180                 185                      190

Ile  Asn  Lys  Asn  Lys  Pro  Ile  Ile  Tyr  Ile  Asp  Ser  Met  Ser  Tyr  Leu
          195                     200                 205

Ile  Phe  Tyr  Asn  Leu  Ile  Lys  Pro  Tyr  Leu  Ile  Pro  Gln  Met  Met  Tyr
     210                     215                 220

Lys  Leu  Pro  Asn  Thr  Ile  Ser  Ser  Glu  Thr  Phe  Leu  Lys
225                      230                 235
```

( 2 ) INFORMATION FOR SEQ ID NO:3:

( i ) SEQUENCE CHARACTERISTICS:
        ( A ) LENGTH: 722 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
AAAAATAAAA  TCATATGAAA  AATATTAAAA  AAAATCAAGT  AATCAATCTC  GGTCCTATTT      60
CTAAATTATT  AAAAGAATAT  AAATCACAAT  TAATTGAATT  AAATATTGAA  CAATTTGAAG     120
CAGGTATTGG  TTTAATTTTA  GGAGATGCTT  ATATTCGTAG  TCGTGATGAA  GGTAAAACTT     180
ATTGTATGCA  ATTTGAGTGG  AAAAATAAGG  CATACATGGA  TCATGTATGT  TTATTATATG     240
ATCAATGGGT  ATTATCACCT  CCTCATAAAA  AGAAAGAGT   TAATCATTTA  GGTAATTTAG     300
TAATTACCTG  GGGAGCTCAA  ACTTTTAAAC  ATCAAGCTTT  TAATAAATTA  GCTAACTTAT     360
TTATTGTAAA  TAATAAAAAA  CTTATTCCTA  ATAATTTAGT  TGAAAATTAT  TTAACACCTA     420
TGAGTCTGGC  ATATTGGTTT  ATGGATGATG  GAGGTAAATG  GGATTATAAT  AAAAATTCTC     480
TTAATAAAG   TATTGTATTA  AATACACAAA  GTTTTACTTT  TGAAGAAGTA  GAATATTTAC     540
TTAAAGGTTT  AAGAAATAAA  TTTCAATTAA  ATTGTTATGT  TAAAATTAAT  AAAAATAAAC     600
CAATTATTTA  TATTGATTCT  ATGAGTTATC  TGATTTTTTA  TAATTTAATT  AAACCTTATT     660
TAATTCCTCA  AATGATGTAT  AAACTGCCTA  ATACTATTTC  ATCCGAAACT  TTTTTAAAAT     720
AA                                                                        722
```

( 2 ) INFORMATION FOR SEQ ID NO:4:

( i ) SEQUENCE CHARACTERISTICS:
        ( A ) LENGTH: 235 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Met Lys Asn Ile Lys Lys Asn Gln Val Met Asn Leu Gly Pro Asn Ser
1               5                   10                  15
Lys Leu Leu Lys Glu Tyr Lys Ser Gln Leu Ile Glu Leu Asn Ile Glu
            20              25                  30
Gln Phe Glu Ala Gly Ile Gly Leu Ile Leu Gly Asp Ala Tyr Ile Arg
        35                  40                  45
Ser Arg Asp Glu Gly Lys Thr Tyr Cys Met Gln Phe Glu Trp Lys Asn
    50              55                  60
Lys Ala Tyr Met Asp His Val Cys Leu Leu Tyr Asp Gln Trp Val Leu
65              70                  75                  80
Ser Pro Pro His Lys Lys Glu Arg Val Asn His Leu Gly Asn Leu Val
                85                  90                  95
Ile Thr Trp Gly Ala Gln Thr Phe Lys His Gln Ala Phe Asn Lys Leu
            100                 105                 110
Ala Asn Leu Phe Ile Val Asn Asn Lys Lys Leu Ile Pro Asn Asn Leu
        115                 120                 125
Val Glu Asn Tyr Leu Thr Pro Met Ser Leu Ala Tyr Trp Phe Met Asp
    130                 135                 140
Asp Gly Gly Lys Trp Asp Tyr Asn Lys Asn Ser Leu Asn Lys Ser Ile
145                 150                 155                 160
Val Leu Asn Thr Gln Ser Phe Thr Phe Glu Glu Val Cys Tyr Leu Val
                165                 170                 175
Lys Gly Leu Arg Asn Lys Phe Gln Leu Asn Cys Tyr Val Lys Ile Asn
            180                 185                 190
Lys Asn Lys Pro Ile Ile Tyr Ile Asp Ser Met Ser Tyr Leu Ile Phe
        195                 200                 205
Tyr Asn Ile Ile Lys Pro Tyr Leu Ile Pro Gln Met Met Tyr Lys Leu
    210                 215                 220
Pro Asn Thr Ile Ser Ser Glu Thr Phe Leu Lys
225                 230                 235
```

( 2 ) INFORMATION FOR SEQ ID NO:5:

( i ) SEQUENCE CHARACTERISTICS:
    ( A ) LENGTH: 754 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:5:

```
CCGGATCCAT GCATATGAAA ACATCAAAA  AAAACCAGGT AATGAACCTG GGTCCGAACT      60
CTAAACTGCT GAAAGAATAC AAATCCCAGC TGATCGAACT GAACATCGAA CAGTTCGAAG     120
CAGGTATCGG TCTGATCCTG GGTGATGCTT ACATCCGTTC TCGTGATGAA GGTAAAACCT     180
ACTGTATGCA GTTCGAGTGG AAAAACAAAG CATACATGGA CCACGTATGT CTGCTGTACG     240
ATCAGTGGGT ACTGTCCCCG CCGCACAAAA AACAACGTGT TAACCACCTG GGTAACCTGG     300
TAATCACCTG GGGCGCCCAG ACTTTCAAAC ACCAAGCTTT CAACAAACTG GCTAACCTGT     360
TCATCGTTAA CAACAAAAAA ACCATCCCGA ACAACCTGGT TGAAAACTAC CTGACCCCGA     420
TGTCTCTGGC ATACTGGTTC ATGGATGATG GTGGTAAATG GGATTACAAC AAAAACTCTA     480
CCAACAAATC GATCGTACTG AACACCCAGT CTTTCACTTT CGAAGAAGTA GAATACCTGG     540
```

| | | | | | |
|---|---|---|---|---|---|
| TTAAGGGTCT | GCGTAACAAA | TTCCAACTGA | ACTGTTACGT | AAAAATCAAC | AAAAACAAAC | 600
| CGATCATCTA | CATCGATTCT | ATGTCTTACC | TGATCTTCTA | CAACCTGATC | AAACCGTACC | 660
| TGATCCCGCA | GATGATGTAC | AAACTGCCGA | ACACTATCTC | CTCCGAAACT | TTCCTGAAAT | 720
| AATAAGTCGA | CTGCAGGATC | CGGTAAGTAA | GTAA | | | 754

(2) INFORMATION FOR SEQ ID NO:6:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

AATGCTTTCC A           11

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GTTACGCTAG GGATAACAGG GTAAT     25

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CAATGCGATC CCTATTGTCC CATTA     25

(2) INFORMATION FOR SEQ ID NO:9:

(i) SEQUENCE CHARACTERISTICS:
        (A) LENGTH: 1738 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

| | | | | | |
|---|---|---|---|---|---|
| GCGGACAGGT | ATCCGGTAAG | CGGCAGGGTC | GGAACAGGAG | AGCGCACGAG | GGAGCTTCCA | 60
| GGGGGAAACG | CCTGGTATCT | TTATAGTCCT | GTCGGGTTTC | GCCACCTCTG | ACTTGAGCGT | 120
| CGATTTTTGT | GATGCTCGTC | AGGGGGGCGG | AGCCTATGGA | AAAACGCCAG | CAACGCGGCC | 180
| TTTTTACGGT | TCCTGGCCTT | TTGCTGGCCT | TTTGCTCACA | TGTTCTTTCC | TGCGTTATCC | 240
| CCTGATTCTG | TGGATAACCG | TATTACCGCC | TTTGAGTGAG | CTGATACCGC | TCGCCGCAGC | 300
| CGAACGACCG | AGCGCAGCGA | GTCAGTGAGC | GAGGAAGCGG | AAGAGCGCCC | AATACGCAAA | 360
| CCGCCTCTCC | CCGCGCGTTG | GCCGATTCAT | TAATGCAGCT | GGCACGACAG | GTTTCCCGAC | 420

-continued

| | | | | | |
|---|---|---|---|---|---|
| TGGAAAGCGG | GCAGTGAGCG | CAACGCAATT | AATGTGAGTT | AGCTCACTCA | TTAGGCACCC | 480 |
| CAGGCTTTAC | ACTTTATGCT | TCCGGCTCGT | ATGTTGTGTG | GAATTGTGAG | CGGATAACAA | 540 |
| TTTCACACAG | GAAACAGCTA | TGACCATGAT | TACGAATTCT | CATGTTTGAC | AGCTTATCAT | 600 |
| CGATAAGCTT | TAATGCGGTA | GTTTATCACA | GTTAAATTGC | TAACGCAGTC | AGGCACCGTG | 660 |
| TATGAAATCT | AACAATGCGC | TCATCGTCAT | CCTCGGCACC | GTCACCCTGG | ATGCTGTAGG | 720 |
| CATAGGCTTG | GTTATGCCGG | TACTGCCGGG | CCTCTTGCGG | GATATCCGCC | TGATGCGTGA | 780 |
| ACGTGACGGA | CGTAACCACC | GCGACATGTG | TGTGCTGTTC | CGCTGGGCAT | GCCAGGACAA | 840 |
| CTTCTGGTCC | GGTAACGTGC | TGAGCCCGGC | CAAGCTTACT | CCCCATCCCC | CTGTTGACAA | 900 |
| TTAATCATCG | GCTCGTATAA | TGTGTGGAAT | TGTGAGCGGA | TAACAATTTC | ACACAGGAAA | 960 |
| CAGGATCCAT | GCATATGAAA | AACATCAAAA | AAAACCAGGT | AATGAACCTG | GGTCCGAACT | 1020 |
| CTAAACTGCT | GAAAGAATAC | AAATCCCAGC | TGATCGAACT | GAACATCGAA | CAGTTCGAAG | 1080 |
| CAGGTATCGG | TCTGATCCTG | GGTGATGCTT | ACATCCGTTC | TCGTGATGAA | GGTAAAACCT | 1140 |
| ACTGTATGCA | GTTCGAGTGG | AAAAACAAAG | CATACATGGA | CCACGTATGT | CTGCTGTACG | 1200 |
| ATCAGTGGGT | ACTGTCCCCG | CCGCACAAAA | AGAACGTGT | TAACCACCTG | GGTAACCTGG | 1260 |
| TAATCACCTG | GGGCGCCCAG | ACTTTCAAAC | ACCAAGCTTT | CAACAAACTG | GCTAACCTGT | 1320 |
| TCATCGTTAA | CAACAAAAAA | ACCATCCCGA | ACAACCTGGT | TGAAAACTAC | CTGACCCCGA | 1380 |
| TGTCTCTGGC | ATACTGGTTC | ATGGATGATG | GTGGTAAATG | GGATTACAAC | AAAAACTCTA | 1440 |
| CCAACAAATC | GATCGTACTG | AACACCCAGT | CTTTCACTTT | CGAAGAAGTA | GAATACCTGG | 1500 |
| TTAAGGGTCT | GCGTAACAAA | TTCCAACTGA | ACTGTTACGT | AAAAATCAAC | AAAAACAAAC | 1560 |
| CGATCATCTA | CATCGATTCT | ATGTCTTACC | TGATCTTCTA | CAACCTGATC | AAACCGTACC | 1620 |
| TCATCCCCCA | GATGATGTAC | AAACTGCCGA | ACACTATCTC | CTCCGAAACT | TTCCTGAAAT | 1680 |
| AATAAGTCGA | CCTGCAGCCC | AAGCTTGGCA | CTGGCCGTCG | TTTTACAACG | TCGTGACT | 1738 |

(2) INFORMATION FOR SEQ ID NO:10:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (xi) SEQUENCE DESCRIPTION: SEQ ID NO:10:

```
Met Leu Val Arg Gly Ala Glu Pro Met Glu Lys Arg Gln Gln Arg Gly
 1               5                  10                  15
Leu Phe Thr Val Pro Gly Leu Leu Leu Ala Phe Cys Ser His Val Leu
            20                  25                  30
Ser Cys Val Ile Pro
            35
```

(2) INFORMATION FOR SEQ ID NO:11:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:11:

```
Met Gln Leu Ala Arg Gln Val Ser Arg Leu Glu Ser Gly Gln
 1               5                  10
```

( 2 ) INFORMATION FOR SEQ ID NO:12:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

```
Met Leu Pro Ala Arg Met Leu Cys Gly Ile Val Ser Gly
 1               5                   10
```

( 2 ) INFORMATION FOR SEQ ID NO:13:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

```
Met Thr Met Ile Thr Asn Ser His Val
 1               5
```

( 2 ) INFORMATION FOR SEQ ID NO:14:

( i ) SEQUENCE CHARACTERISTICS:
        ( A ) LENGTH: 80 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

```
Met Lys Ser Asn Asn Ala Leu Ile Val Ile Leu Gly Thr Val Thr Leu
 1               5                   10                  15
Asp Ala Val Gly Ile Gly Leu Val Met Pro Val Leu Pro Gly Leu Leu
                 20                  25                  30
Arg Asp Ile Arg Leu Met Arg Glu Arg Asp Gly Arg Asn His Arg Asp
             35                  40                  45
Met Cys Val Leu Phe Arg Trp Ala Cys Gln Asp Asn Phe Trp Ser Gly
         50                  55                  60
Asn Val Leu Ser Pro Ala Lys Leu Thr Pro His Pro Pro Val Asp Asn
 65                  70                  75                  80
```

( 2 ) INFORMATION FOR SEQ ID NO:15:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

```
Met Cys Gly Ile Val Ser Gly
 1               5
```

( 2 ) INFORMATION FOR SEQ ID NO:16:

( i ) SEQUENCE CHARACTERISTICS:
        ( A ) LENGTH: 237 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

| Met<br>1 | His | Met | Lys | Asn<br>5 | Ile | Lys | Lys | Asn | Gln<br>10 | Val | Met | Asn | Leu | Gly<br>15 | Pro |
| --- | --- | --- | --- | --- | --- | --- | --- | --- | --- | --- | --- | --- | --- | --- | --- |
| Asn | Ser | Lys | Leu<br>20 | Leu | Lys | Glu | Tyr | Lys<br>25 | Ser | Gln | Leu | Ile | Glu<br>30 | Leu | Asn |
| Ile | Glu | Gln<br>35 | Phe | Glu | Ala | Gly | Ile<br>40 | Gly | Leu | Ile | Leu | Gly<br>45 | Asp | Ala | Tyr |
| Ile | Arg<br>50 | Ser | Arg | Asp | Glu | Gly<br>55 | Lys | Thr | Tyr | Cys | Met<br>60 | Gln | Phe | Glu | Trp |
| Lys<br>65 | Asn | Lys | Ala | Tyr | Met<br>70 | Asp | His | Val | Cys | Leu<br>75 | Leu | Tyr | Asp | Gln | Trp<br>80 |
| Val | Leu | Ser | Pro | Pro<br>85 | His | Lys | Lys | Glu | Arg<br>90 | Val | Asn | His | Leu | Gly<br>95 | Asn |
| Leu | Val | Ile | Thr<br>100 | Trp | Gly | Ala | Gln | Thr<br>105 | Phe | Lys | His | Gln | Ala<br>110 | Phe | Asn |
| Lys | Leu | Ala<br>115 | Asn | Leu | Phe | Ile | Val<br>120 | Asn | Asn | Lys | Lys | Thr<br>125 | Ile | Pro | Asn |
| Asn | Leu<br>130 | Val | Glu | Asn | Tyr | Leu<br>135 | Thr | Pro | Met | Ser | Leu<br>140 | Ala | Tyr | Trp | Phe |
| Met<br>145 | Asp | Asp | Gly | Gly | Lys<br>150 | Trp | Asp | Tyr | Asn | Lys<br>155 | Asn | Ser | Thr | Asn | Lys<br>160 |
| Ser | Ile | Val | Leu | Asn<br>165 | Thr | Gln | Ser | Phe | Thr<br>170 | Phe | Glu | Glu | Val | Glu<br>175 | Tyr |
| Leu | Val | Lys | Gly<br>180 | Leu | Arg | Asn | Lys | Phe<br>185 | Gln | Leu | Asn | Cys | Tyr<br>190 | Val | Lys |
| Ile | Asn | Lys<br>195 | Asn | Lys | Pro | Ile | Ile<br>200 | Tyr | Ile | Asp | Ser | Met<br>205 | Ser | Tyr | Leu |
| Ile | Phe | Tyr<br>210 | Asn | Leu | Ile | Lys<br>215 | Pro | Tyr | Leu | Ile | Pro<br>220 | Gln | Met | Met | Tyr |
| Lys<br>225 | Leu | Pro | Asn | Thr | Ile<br>230 | Ser | Ser | Glu | Thr | Phe<br>235 | Leu | Lys | | | |

( 2 ) INFORMATION FOR SEQ ID NO:17:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

CGCTAGGGAT AACAGGGTAA TATAGC 26

( 2 ) INFORMATION FOR SEQ ID NO:18:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

GCGATCCCTA TTGTCCCATT ATATCG 26

( 2 ) INFORMATION FOR SEQ ID NO:19:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

TTCTCATGAT TAGCTCTAAT CCATGG      26

( 2 ) INFORMATION FOR SEQ ID NO:20:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

AAGAGTACTA ATCGAGATTA GGTACC      26

( 2 ) INFORMATION FOR SEQ ID NO:21:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

CTTTGGTCAT CCAGAAGTAT ATATTT      26

( 2 ) INFORMATION FOR SEQ ID NO:22:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

GAAACCAGTA GGTCTTCATA TATAAA      26

( 2 ) INFORMATION FOR SEQ ID NO:23:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

TAACGGTCCT AAGGTAGCGA AATTCA      26

( 2 ) INFORMATION FOR SEQ ID NO:24:

( i ) SEQUENCE CHARACTERISTICS:
        ( A ) LENGTH: 26 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:24:

ATTGCCAGGA TTCCATCGCT TTAAGT 26

( 2 ) INFORMATION FOR SEQ ID NO:25:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:25:

TGACTCTCTT AAGGTAGCCA AATGCC 26

( 2 ) INFORMATION FOR SEQ ID NO:26:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:26:

ACTGAGAGAA TTCCATCGGT TTACGG 26

( 2 ) INFORMATION FOR SEQ ID NO:27:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:27:

CGAGGTTTTG GTAACTATTT ATTACC 26

( 2 ) INFORMATION FOR SEQ ID NO:28:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:28:

CCTCCAAAAC CATTGATAAA TAATGG 26

( 2 ) INFORMATION FOR SEQ ID NO:29:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:29:

GGGTTCAAAA CGTCGTGAGA CAGTTT                                                                26

( 2 ) INFORMATION FOR SEQ ID NO:30:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

CCCAAGTTTT GCAGCACTCT GTCAAA                                                                26

( 2 ) INFORMATION FOR SEQ ID NO:31:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

GATGCTGTAG GCATAGGCTT GGTTAT                                                                26

( 2 ) INFORMATION FOR SEQ ID NO:32:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

CTACGACATC CGTATCCGAA CCAATA                                                                26

( 2 ) INFORMATION FOR SEQ ID NO:33:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

CTTTCCGCAA CAGTATAATT TTATAA                                                                26

( 2 ) INFORMATION FOR SEQ ID NO:34:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

GAAAGGCGTT GTCATATTAA AATATT                                                                26

( 2 ) INFORMATION FOR SEQ ID NO:35:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

ACCATGGGGT CAAATGTCTT TCTGGG        26

( 2 ) INFORMATION FOR SEQ ID NO:36:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:36:

TGGTACCCCA GTTTACAGAA AGACCC        26

( 2 ) INFORMATION FOR SEQ ID NO:37:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

GTGCCTGAAT GATATTTATT ACCTTT        26

( 2 ) INFORMATION FOR SEQ ID NO:38:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:38:

GTGCCTGAAT GATATTTATT ACCTTT        26

( 2 ) INFORMATION FOR SEQ ID NO:39:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

CAACGCTCAG TAGATGTTTT CTTGGGTCTA CCGTTTAAT        39

( 2 ) INFORMATION FOR SEQ ID NO:40:

( i ) SEQUENCE CHARACTERISTICS:
        ( A ) LENGTH: 39 base pairs
        ( B ) TYPE: nucleic acid

```
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:40:
```

GTTGCGAGTC ATCTACAAAA GAACCCAGAT GGCAAATTA    39

( 2 ) INFORMATION FOR SEQ ID NO:41:

```
    ( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:41:
```

CAAGCTTATG AGTATGAAGT GAACACGTTA TT    32

( 2 ) INFORMATION FOR SEQ ID NO:42:

```
    ( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:42:
```

GTTCGAATAC TCATACTTCA CTTGTGCAAT AA    32

( 2 ) INFORMATION FOR SEQ ID NO:43:

```
    ( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:
```

GCTATTCGTT TTTATGTATC TTTTGCGTGT AGCTTTAA    38

( 2 ) INFORMATION FOR SEQ ID NO:44:

```
    ( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:
```

CGATAAGCAA AAATACATAG AAAACGCACA TGGAAATT    38

( 2 ) INFORMATION FOR SEQ ID NO:45:

```
    ( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA (genomic)
```

( x i ) SEQUENCE DESCRIPTION: SEQ ID NO:45:

CCAAGCTCGA ATTCGCATGC TCTAGAGCTC GGTACCCGGG ATCCTGCAGT CGACGCTAGG        60

GATAACAGGG TAATACAGAT        80

( 2 ) INFORMATION FOR SEQ ID NO:46:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

GGTTCGAGCT TAAGCGTACG AGATCTCGAG CCATGGGCCC TAGGACGTCA GCTGCGATCC        60

CTATTGTCCC ATTATGTCTA        80

( 2 ) INFORMATION FOR SEQ ID NO:47:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

ATCAGATCTA AGCTTGCATG CCTGCAGGTC GACTCTAGAG GATCCCCGGG TACCGAGCTC        60

GAATTCACTG GCCGTCGTTT        80

( 2 ) INFORMATION FOR SEQ ID NO:48:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

TAGTCTAGAT TCGAACGTAC GGACGTCCAG CTGAGATCTC CTAGGGCCC ATGGCTCGAG        60

CTTAAGTGAC CGGCAGCAAA        80

( 2 ) INFORMATION FOR SEQ ID NO:49:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

TACAACGTCG TGACTGGGAA AACCCTGGCG TTACCCAACT TAATCGCCTT GCAGCACATC        60

CCCCTTTCGC CAGCTGGCGT        80

( 2 ) INFORMATION FOR SEQ ID NO:50:

( i ) SEQUENCE CHARACTERISTICS:
        ( A ) LENGTH: 80 base pairs
        ( B ) TYPE: nucleic acid (C) STRANDEDNESS: single
(D) TOPOLOGY: linear (i i) MOLECULE TYPE: DNA (genomic)

(x i) SEQUENCE DESCRIPTION: SEQ ID NO:50:

ATGTTGCAGC ACTGACCCTT TTGGGACCGC AATGGGTTGA ATTAGCGGAA CGTCGTGTAG    60

GGGGAAAGCG GTCGACCGCA    80

(2) INFORMATION FOR SEQ ID NO:51:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:51:

TAGGGATAAC AGGGTAAT    18

(2) INFORMATION FOR SEQ ID NO:52:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:52:

ATCCCTATTG TCCCATTA    18